United States Patent
Lee et al.

(10) Patent No.: US 10,256,416 B2
(45) Date of Patent: Apr. 9, 2019

(54) COMPOUND AND ORGANIC LIGHT-EMITTING DEVICE INCLUDING THE SAME

(71) Applicant: SAMSUNG DISPLAY CO., LTD., Yongin, Gyeonggi-Do (KR)

(72) Inventors: Eun-Young Lee, Yongin (KR); Seok-Hwan Hwang, Yongin (KR); Young-Kook Kim, Yongin (KR); Hye-Jin Jung, Yongin (KR); Jun-Ha Park, Yongin (KR); Jong-Woo Kim, Yongin (KR); Jin-O Lim, Yongin (KR); Sang-Hyun Han, Yongin (KR); Eun-Jae Jeong, Yongin (KR); Soo-Yon Kim, Yongin (KR); Jong-Hyuk Lee, Yongin (KR)

(73) Assignee: Samsung Display Co., Ltd., Yongin-si (KR)

( * ) Notice: Subject to any disclaimer, the term of this patent is extended or adjusted under 35 U.S.C. 154(b) by 317 days.

(21) Appl. No.: 14/072,478

(22) Filed: Nov. 5, 2013

(65) Prior Publication Data
US 2015/0001479 A1    Jan. 1, 2015

(30) Foreign Application Priority Data

Jul. 1, 2013 (KR) .................. 10-2013-0076597

(51) Int. Cl.
*H01L 51/00* (2006.01)
*C07D 311/78* (2006.01)
(Continued)

(52) U.S. Cl.
CPC ........ *H01L 51/0073* (2013.01); *C07B 59/001* (2013.01); *C07C 13/567* (2013.01);
(Continued)

(58) Field of Classification Search
None
See application file for complete search history.

(56) References Cited

U.S. PATENT DOCUMENTS

| | | |
|---|---|---|
| 3,968,051 A | 7/1976 | Stamm et al. |
| 5,635,308 A | 6/1997 | Inoue et al. |

(Continued)

FOREIGN PATENT DOCUMENTS

| | | |
|---|---|---|
| CN | 102925139 A | 2/2013 |
| JP | 8-12600 A | 1/1996 |

(Continued)

OTHER PUBLICATIONS

Ding et al., "A Succinct Synthesis of the Vaulted Biaryl Ligand Vanol via a Dienone-Phenol Rearrangement", Full Papers, 2011 Wiley-VCH Verlag GmbH & Co., KGaA, Weinheim, Chem. Asian J. 2011, 6, 2130-2146, 17 pages.

(Continued)

*Primary Examiner* — Jay Yang
(74) *Attorney, Agent, or Firm* — Lewis Roca Rothgerber Christie LLP

(57) ABSTRACT

A compound is represented by Formula 1, 2, or 3, and an organic light-emitting device includes the compound. The organic light-emitting device includes a first electrode, a second electrode, and an organic layer. The organic layer includes the compound represented by Formula 1, 2 or 3. A (Continued)

flat display apparatus includes the organic light-emitting device.

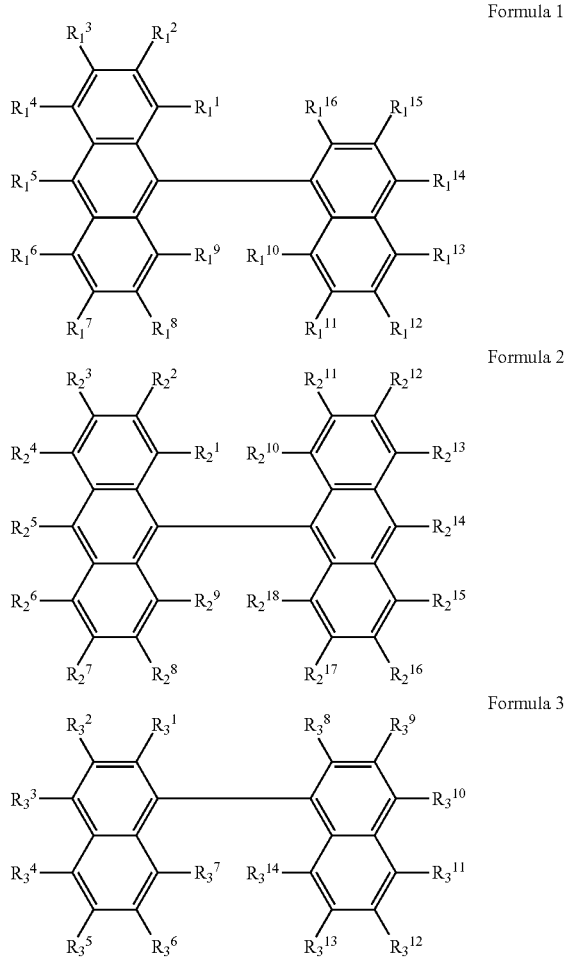

20 Claims, 1 Drawing Sheet

(51) Int. Cl.
C07D 405/04 (2006.01)
C07D 405/10 (2006.01)
C07F 7/08 (2006.01)
C07C 13/567 (2006.01)
C07C 13/62 (2006.01)
C07C 15/28 (2006.01)
C07C 15/30 (2006.01)
C07C 15/38 (2006.01)
C09K 11/06 (2006.01)
C07B 59/00 (2006.01)
C09B 11/28 (2006.01)
C09B 1/00 (2006.01)
H01L 51/50 (2006.01)

(52) U.S. Cl.
CPC .......... C07C 13/62 (2013.01); C07C 15/28 (2013.01); C07C 15/30 (2013.01); C07C 15/38 (2013.01); C07D 311/78 (2013.01); C07D 405/04 (2013.01); C07D 405/10 (2013.01); C07F 7/0814 (2013.01); C09B 1/00 (2013.01); C09B 1/005 (2013.01); C09B 11/28 (2013.01); C09K 11/06 (2013.01); H01L 51/0058 (2013.01); C07B 2200/05 (2013.01); C07C 2603/18 (2017.05); C07C 2603/24 (2017.05); C07C 2603/26 (2017.05); C07C 2603/50 (2017.05); C09K 2211/1011 (2013.01); C09K 2211/1014 (2013.01); C09K 2211/1029 (2013.01); C09K 2211/1044 (2013.01); C09K 2211/1059 (2013.01); C09K 2211/1088 (2013.01); H01L 51/006 (2013.01); H01L 51/0059 (2013.01); H01L 51/0081 (2013.01); H01L 51/5012 (2013.01); H01L 51/5072 (2013.01)

(56) References Cited

U.S. PATENT DOCUMENTS

| | | | |
|---|---|---|---|
| 5,972,247 | A | 10/1999 | Shi et al. |
| 6,465,115 | B2 | 10/2002 | Shi et al. |
| 6,582,837 | B1 | 6/2003 | Toguchi et al. |
| 6,596,415 | B2 | 7/2003 | Shi et al. |
| 7,053,255 | B2 | 5/2006 | Ikeda et al. |
| 7,233,019 | B2 | 6/2007 | Ionkin et al. |
| 7,732,063 | B2 | 6/2010 | Matsuura et al. |
| 7,839,074 | B2 | 11/2010 | Ikeda et al. |
| 8,221,905 | B2 | 7/2012 | Lin et al. |
| 8,324,802 | B2 | 12/2012 | Matsuura et al. |
| 8,334,648 | B2 | 12/2012 | Matsuura et al. |
| 9,680,108 | B2 | 6/2017 | Ito et al. |
| 9,711,736 | B2 | 7/2017 | Han et al. |
| 9,893,289 | B2 | 2/2018 | Ito et al. |
| 10,062,850 | B2 | 8/2018 | Jung et al. |
| 2004/0076853 | A1 | 4/2004 | Jarikov |
| 2004/0137270 | A1 | 7/2004 | Seo et al. |
| 2004/0214036 | A1 | 10/2004 | Bentsen et al. |
| 2005/0664283 | | 3/2005 | Matsuura et al. |
| 2005/0089717 | A1 | 4/2005 | Cosimbescu et al. |
| 2005/0156164 | A1 | 7/2005 | Sotoyama |
| 2005/0214565 | A1 | 9/2005 | Ikeda et al. |
| 2005/0245752 | A1 | 11/2005 | Conley et al. |
| 2005/0249972 | A1* | 11/2005 | Hatwar ............... H01L 51/5265 428/690 |
| 2006/0052641 | A1 | 3/2006 | Funahashi |
| 2006/0083945 | A1 | 4/2006 | Morishita et al. |
| 2006/0113905 | A1* | 6/2006 | Nakamura .......... H01L 27/3244 313/511 |
| 2006/0152146 | A1 | 7/2006 | Funahashi |
| 2006/0159952 | A1 | 7/2006 | Ricks et al. |
| 2007/0114917 | A1 | 5/2007 | Funahashi et al. |
| 2007/0152565 | A1 | 7/2007 | Kubota et al. |
| 2007/0155991 | A1 | 7/2007 | Funahashi |
| 2007/0170419 | A1 | 7/2007 | Gerhard et al. |
| 2007/0237984 | A1 | 10/2007 | Matsuura et al. |
| 2008/0160342 | A1 | 7/2008 | Meng et al. |
| 2008/0193796 | A1 | 8/2008 | Arakane et al. |
| 2009/0004458 | A1 | 1/2009 | Falster et al. |
| 2009/0004485 | A1* | 1/2009 | Zheng ................ C07C 255/09 428/446 |
| 2009/0026930 | A1 | 1/2009 | Shin et al. |
| 2010/0013381 | A1 | 1/2010 | Stoessel et al. |
| 2010/0032658 | A1 | 2/2010 | Lee et al. |
| 2010/0052526 | A1 | 3/2010 | Je et al. |
| 2010/0127618 | A1 | 5/2010 | Ohrui et al. |
| 2010/0187521 | A1 | 7/2010 | Park et al. |
| 2010/0244012 | A1 | 9/2010 | Mazur et al. |
| 2010/0270913 | A1 | 10/2010 | Matsuura et al. |
| 2010/0277061 | A1 | 11/2010 | Matsuura et al. |
| 2010/0295445 | A1 | 11/2010 | Kuma et al. |
| 2010/0314615 | A1 | 12/2010 | Mizuki et al. |
| 2011/0001130 | A1 | 1/2011 | Nishimura et al. |
| 2011/0006289 | A1 | 1/2011 | Mizuki et al. |
| 2011/0057116 | A1 | 3/2011 | Trogler et al. |
| 2011/0156016 | A1 | 6/2011 | Kawamura et al. |
| 2011/0210320 | A1 | 9/2011 | Shin et al. |

(56) References Cited

U.S. PATENT DOCUMENTS

| | | | |
|---|---|---|---|
| 2011/0284832 A1 | 11/2011 | In et al. | |
| 2012/0001158 A1 | 1/2012 | Asari et al. | |
| 2012/0032152 A1 | 2/2012 | Kim et al. | |
| 2012/0056165 A1 | 3/2012 | Kawamura et al. | |
| 2012/0091885 A1 | 4/2012 | Kim et al. | |
| 2012/0138915 A1 | 6/2012 | Nishimura et al. | |
| 2012/0181518 A1 | 7/2012 | Ogiwara et al. | |
| 2012/0181922 A1 | 7/2012 | Kawamura et al. | |
| 2012/0235561 A1 | 9/2012 | Ikeda et al. | |
| 2012/0305904 A1 | 12/2012 | Kai et al. | |
| 2012/0313511 A1 | 12/2012 | Tsurutani et al. | |
| 2013/0001526 A1 | 1/2013 | Kwak et al. | |
| 2013/0049581 A1 | 2/2013 | Nishide et al. | |
| 2013/0090446 A1 | 4/2013 | Zhou et al. | |
| 2013/0105786 A1 | 5/2013 | Watanabe et al. | |
| 2013/0112949 A1 | 5/2013 | Sim et al. | |
| 2013/0119355 A1 | 5/2013 | Han et al. | |
| 2013/0221332 A1 | 8/2013 | Xia et al. | |
| 2013/0228752 A1 | 9/2013 | Shin et al. | |
| 2013/0295706 A1 | 11/2013 | Goto et al. | |
| 2013/0306958 A1 | 11/2013 | Ito et al. | |
| 2014/0008641 A1 | 1/2014 | Kubota et al. | |
| 2014/0048792 A1 | 2/2014 | Chun et al. | |
| 2014/0124763 A1 | 5/2014 | Funahashi | |
| 2014/0175395 A1 | 6/2014 | Kim et al. | |
| 2014/0264301 A1 | 9/2014 | Takaku et al. | |
| 2014/0332772 A1 | 11/2014 | Han et al. | |
| 2014/0346406 A1 | 11/2014 | Lee et al. | |
| 2014/0346464 A1 | 11/2014 | Kim et al. | |
| 2014/0346482 A1 | 11/2014 | Mizuki et al. | |
| 2015/0001479 A1 | 1/2015 | Lee et al. | |
| 2015/0053946 A1 | 2/2015 | Kim et al. | |
| 2015/0069344 A1* | 3/2015 | Kim | H01L 51/0054 257/40 |
| 2015/0090964 A1 | 4/2015 | Hwang et al. | |
| 2015/0090965 A1 | 4/2015 | Park et al. | |
| 2015/0108448 A1 | 4/2015 | Dai et al. | |
| 2015/0171337 A1 | 6/2015 | Jung et al. | |
| 2015/0236273 A1 | 8/2015 | Jang et al. | |
| 2015/0255736 A1 | 9/2015 | Kim et al. | |
| 2015/0318508 A1 | 11/2015 | Kim et al. | |
| 2015/0333266 A1 | 11/2015 | Ito et al. | |
| 2015/0333268 A1 | 11/2015 | Han et al. | |
| 2015/0349265 A1 | 12/2015 | Hwang et al. | |
| 2015/0357574 A1 | 12/2015 | Ito et al. | |
| 2015/0364693 A1 | 12/2015 | Ito et al. | |
| 2016/0005980 A1 | 1/2016 | Ito et al. | |
| 2016/0020404 A1 | 1/2016 | Ito et al. | |
| 2016/0133845 A1 | 5/2016 | Jung et al. | |

FOREIGN PATENT DOCUMENTS

| | | |
|---|---|---|
| JP | 11-003782 A | 1/1999 |
| JP | 2002-63989 | 2/2002 |
| JP | 2003-306454 | 10/2003 |
| JP | 2005-041843 A | 2/2005 |
| JP | 2006-273737 A | 10/2006 |
| JP | 2008-291263 | 12/2008 |
| JP | 2009-212238 | 9/2009 |
| JP | 2011-176267 A | 9/2011 |
| JP | 2012-82209 | 4/2012 |
| JP | 2012-119592 A | 6/2012 |
| JP | 2012-156499 A | 8/2012 |
| JP | 2013-063930 | 4/2013 |
| JP | 2013-063931 | 4/2013 |
| JP | 52-08271 B2 | 6/2013 |
| JP | 5281304 | 9/2013 |
| KR | 10-2005-0058465 | 6/2005 |
| KR | 10-2005-0086518 | 8/2005 |
| KR | 10-2005-0107809 | 11/2005 |
| KR | 10-2006-0006760 | 1/2006 |
| KR | 10-2006-0109524 | 10/2006 |
| KR | 10-2006-0113954 | 11/2006 |
| KR | 10-2006-0127138 | 12/2006 |
| KR | 10-2007-0009074 | 1/2007 |
| KR | 10-2007-0015195 | 2/2007 |
| KR | 10-2007-0050393 A | 5/2007 |
| KR | 10-2008-0068720 A | 7/2008 |
| KR | 10-2009-0010763 A | 1/2009 |
| KR | 10-2009-0033493 | 4/2009 |
| KR | 10-2009-0122922 A | 12/2009 |
| KR | 10-2010-0007552 | 1/2010 |
| KR | 10-2010-0007780 | 1/2010 |
| KR | 10-2010-0024894 | 3/2010 |
| KR | 10-2010-0048203 | 5/2010 |
| KR | 10-2010-0057465 | 5/2010 |
| KR | 10-2010-0070979 | 6/2010 |
| KR | 10-2010-0070992 | 6/2010 |
| KR | 10-2010-0093085 | 8/2010 |
| KR | 10-2010-0097182 | 9/2010 |
| KR | 10-2010-0099327 | 9/2010 |
| KR | 10-2010-0105099 | 9/2010 |
| KR | 10-2011-0015213 | 2/2011 |
| KR | 10-2011-0041728 | 4/2011 |
| KR | 10-2011-0043625 A | 4/2011 |
| KR | 10-2011-0047278 A | 5/2011 |
| KR | 10-2011-0094271 | 8/2011 |
| KR | 10-2011-0107679 | 10/2011 |
| KR | 10-2011-0134885 | 12/2011 |
| KR | 10-2012-0002865 | 1/2012 |
| KR | 10-2012-0026513 | 3/2012 |
| KR | 10-2012-0039470 | 4/2012 |
| KR | 10-2012-0041110 | 4/2012 |
| KR | 10-1132635 B1 | 4/2012 |
| KR | 10-2012-0057611 | 6/2012 |
| KR | 10-2012-0066390 | 6/2012 |
| KR | 10-2012-0093354 | 8/2012 |
| KR | 10-2012-0117622 | 10/2012 |
| KR | 10-2012-0117675 | 10/2012 |
| KR | 10-2013-0007495 | 1/2013 |
| KR | 10-2013-0009765 | 1/2013 |
| KR | 10-1233377 | 2/2013 |
| KR | 10-1262420 | 5/2013 |
| KR | 10-2013-0100948 | 9/2013 |
| WO | WO 2010/050781 A1 | 5/2010 |
| WO | WO 2010/058995 A1 | 5/2010 |
| WO | WO 2010/107244 A2 | 9/2010 |
| WO | WO 2010/137678 A1 | 12/2010 |
| WO | WO 2012/070226 A1 | 5/2012 |
| WO | WO 2012/070234 A1 | 5/2012 |
| WO | WO 2013/051875 A2 | 4/2013 |

OTHER PUBLICATIONS

Katritzky, A., et al., "Polycyclic Fused Phenanthridines: An Alternative Approach from Benzotriazoles", Center for Heterocyclic Compounds., Department of Chemistry, Univ. of Florida, pp. 1-27.
Notice of Allowance dated Jul. 15, 2016, for cross reference U.S. Appl. No. 14/533,004.
STIC Search Report for cross reference U.S. Appl. No. 14/533,004, dated Dec. 1, 2015 (15 pages).
U.S. Office action dated Dec. 8, 2015, for cross referenced U.S. Appl. No. 14/533,004, (12 pages).
U.S. Office action dated May 5, 2016, for cross referenced U.S. Appl. No. 14/195,836, (18 pages).
U.S. Office action dated Oct. 6, 2016, for cross referenced U.S. Appl. No. 14/550,801, (9 pages).
Leem et al., "Highly efficient tandem p-i-n organic light-emitting diodes adopting a low temperature evaporated rhenium oxide interconnecting later," Applied Physics Letters, 93, 103304-1-3, 2008.
Kaminaga, et al., Machine Translation of JP 2011-176267A, dated Sep. 2011, Retrieved from Google Patents on Feb. 3, 2017, pp. 1-44.
U.S. Office Action dated Apr. 20, 2016, issued in cross-reference U.S. Appl. No. 14/075,573 (10 pages).
U.S. Notice of Allowance dated Feb. 10, 2017, issued in cross-reference U.S. Appl. No. 14/533,004 (12 pages).
U.S. Office Action dated Feb. 16, 2017, issued in cross-reference U.S. Appl. No. 14/075,573 (14 pages).
Yumiko et al., Machine English translation of KR 10-2010-0097182. Mar. 10, 2017.

(56) References Cited

OTHER PUBLICATIONS

U.S. Notice of Allowance dated Mar. 27, 2017, issued in cross-reference U.S. Appl. No. 14/550,801 (9 pages).
U.S. Office Action dated May 18, 2017, issued in cross-reference U.S. Appl. No. 14/789,672 (18 pages).
Machine English translation of Shin et al. (KR 10-2009-0010763), 27 pages.
U.S. Notice of Allowance dated Mar. 15, 2017, issued in U.S. Appl. No. 14/513,144 (9 pages).
U.S. Office Action dated Aug. 23, 2017, issued in U.S. Appl. No. 14/702,970 (9 pages).
U.S. Office Action dated Sep. 7, 2017, issued in U.S. Appl. No. 14/789,672 (16 pages).
Machine translation for JP 2012-119592 A, dated Jun. 21, 2012, 27 pages.
Machine Translation for KR 10-2011-0041728, dated Apr. 22, 2011, 19 pages.
U.S. Office Action dated Jul. 13, 2017, issued in cross-reference U.S. Appl. No. 14/508,677 (10 pages).
Machine translation for JP 2012-119592 A (dated Jun. 2012), 52 pages.
U.S. Office Action dated Dec. 18, 2017, issued in U.S. Appl. No. 14/550,801 (9 pages).
U.S. Office Action dated Dec. 20, 2017, issued in U.S. Appl. No. 14/195,836 (9 pages).
U.S. Notice of Allowance dated Jan. 25, 2018, issued in U.S. Appl. No. 14/075,573 (8 pages).
U.S. Notice of Allowance dated Mar. 13, 2018, issued in U.S. Appl. No. 14/789,672 (10 pages).
U.S. Office Action dated Sep. 19, 2018, issued in U.S. Appl. No. 14/195,836 (17 pages).

\* cited by examiner

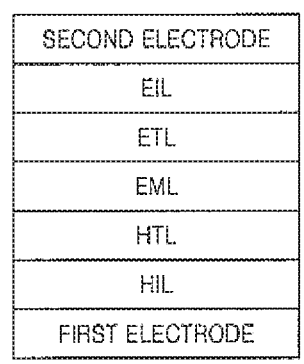

COMPOUND AND ORGANIC LIGHT-EMITTING DEVICE INCLUDING THE SAME

CROSS-REFERENCE TO RELATED APPLICATION

This application claims priority to and the benefit of Korean Patent Application No. 10-2013-0076597, filed on Jul. 1, 2013 in the Korean Intellectual Property Office, the entire content of which is incorporated herein by reference.

BACKGROUND

1. Technical Field

One or more embodiments of the present invention relate to a compound and an organic light-emitting device including the same.

2. Description of the Related Art

Organic light-emitting devices (OLEDs) are self-emitting devices having advantages such as wide viewing angles, good contrast, quick response speeds, high brightness, and good driving voltage characteristics. Also, OLEDs can provide full color images.

A typical OLED has a structure including a substrate, and an anode, a hole transport layer, an emission layer, an electron transport layer, and a cathode sequentially stacked on the substrate. The hole transport layer, the emission layer, and the electron transport layer are organic thin films formed of organic compounds.

A driving principle of an organic light-emitting device having such a structure is as follows. When a voltage is applied between the anode and the cathode, holes injected from the anode pass through the hole transport layer and migrate toward the emission layer, and electrons injected from the cathode pass through the electron transport layer and migrate toward the emission layer. The holes and electrons are recombined with each other in the emission layer to generate excitons. Then, the excitons transition from an excited state to a ground state, thereby generating light.

SUMMARY

One or more embodiments of the present invention include a material that has good electric characteristics, high charge transporting capabilities, high light-emitting capabilities, a high glass transition temperature, and crystallization-preventing capabilities. The material is suitable for use as a material for a full color (such as red, green, blue, or white) fluorescent or phosphorescent devices. An organic light-emitting device that includes the material has high efficiency, low voltage, high brightness, and a long lifespan.

Additional aspects will be set forth in part in the description that follows and, in part, will be apparent from the description, or may be learned by practice of the presented embodiments.

According to one or more embodiments of the present invention, a compound is represented by Formula 1, Formula 2, or Formula 3 below.

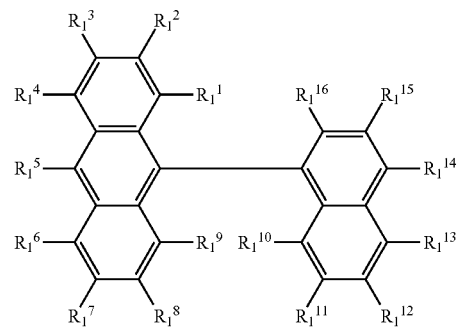

Formula 1

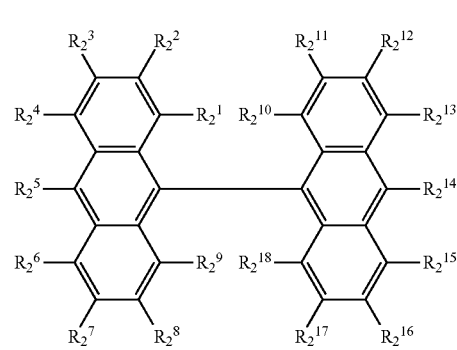

Formula 2

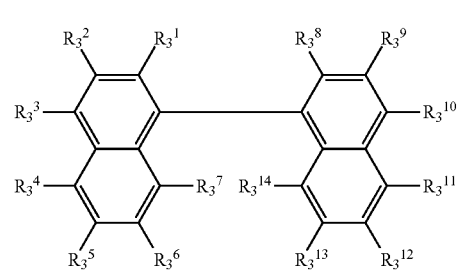

Formula 3

In Formulae 1, 2, and 3:

$R_1^1$ to $R_1^{16}$, $R_2^1$ to $R_2^{18}$, and $R_3^1$ to $R_3^{14}$ are each independently a hydrogen atom, a deuterium atom, a halogen atom, a nitro group, a cyano group, a substituted or unsubstituted $C_1$ to $C_{60}$ alkyl group, a substituted or unsubstituted $C_2$ to $C_{60}$ alkenyl group, a substituted or unsubstituted $C_3$ to $C_{60}$ cycloalkyl group, a substituted or unsubstituted $C_6$ to $C_{60}$ aryl group, a substituted or unsubstituted $C_2$ to $C_{60}$ hetero aryl group, or a substituted or unsubstituted $C_6$ to $C_{60}$ condensed polycyclic group; and

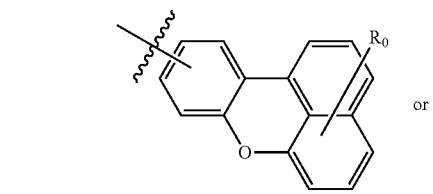

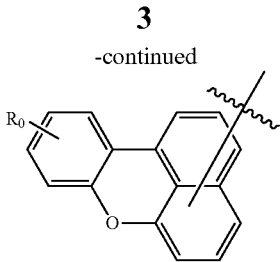

at least one of $R_1^1$ to $R_1^{16}$, at least one of $R_2^1$ to $R_2^{16}$, and at least one of $R_3^1$ to $R_3^{14}$ may include one or more L. L is, where the definition of $R_0$ is the same as the definition (above) of $R_1^1$ to $R_1^{16}$, $R_2^1$ to $R_2^{18}$, and $R_3^1$ to $R_3^{14}$.

According to another aspect of the present invention, an organic light-emitting device includes a first electrode, a second electrode, and an organic layer between the first electrode and the second electrode. The organic layer includes the compound of Formula 1, 2 or 3.

According to another aspect of the present invention, a flat panel display apparatus includes the organic light-emitting device, and the first electrode of the organic light-emitting device is electrically connected to a source electrode or a drain electrode of a thin film transistor.

BRIEF DESCRIPTION OF THE DRAWINGS

These and/or other aspects will become apparent and more readily appreciated from the following description of certain embodiments when taken in conjunction with the FIGURE, which is a schematic view of an organic light-emitting device according to an embodiment of the present invention.

DETAILED DESCRIPTION

Reference will now be made to certain embodiments, examples of which are illustrated in the accompanying drawings. Like reference numerals refer to like elements throughout. It is understood, however, that the disclosed embodiments may be modified in different ways, and therefore should not be construed as limiting the present invention to the described embodiments. Accordingly, the presented embodiments are merely described below, by reference to the FIGURE, to explain certain aspects of the present invention. As used herein, the term "and/or" includes any and all combinations of one or more of the associated listed items. Expressions such as "at least one of," when preceding a list of elements, modify the entire list of elements and do not modify the individual elements of the list.

According to an aspect of the present invention, a compound is represented by Formula 1, Formula 2, or Formula 3.

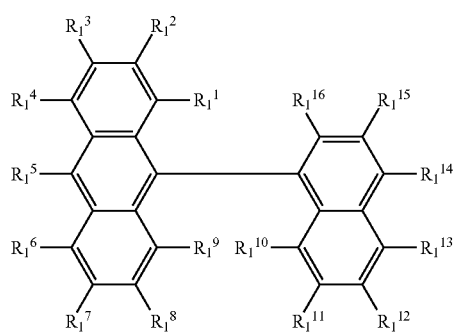

Formula 1

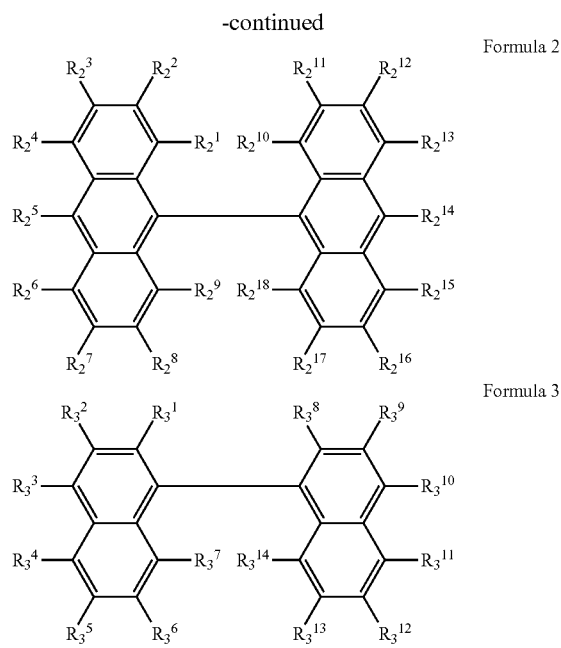

Formula 2

Formula 3

In Formulae 1, 2, and 3:
$R_1^1$-$R_1^{16}$, $R_2^1$-$R_2^{18}$, and $R_3^1$-$R_3^{14}$ are each independently a hydrogen atom, a deuterium atom, a halogen atom, a nitro group, a cyano group, a substituted or unsubstituted $C_1$ to $C_{60}$ alkyl group, a substituted or unsubstituted $C_2$ to $C_{60}$ alkenyl group, a substituted or unsubstituted $C_3$ to $C_{60}$ cycloalkyl group, a substituted or unsubstituted $C_6$ to $C_{60}$ aryl group, a substituted or unsubstituted $C_1$ to $C_{60}$ hetero aryl group, or a substituted or unsubstituted $C_6$ to $C_{60}$ condensed polycyclic group; and at least one of $R_1^1$-$R_1^{16}$, at least one of $R_2^1$-$R_2^{18}$, and at least one of $R_3^1$-$R_3^{14}$ may include one or more L. L is

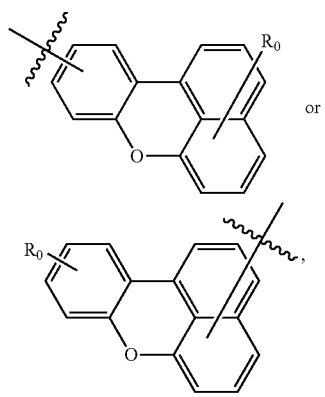

and the definition of $R_0$ is the same as the definition (above) of $R_1^1$-$R_1^{16}$, $R_2^1$-$R_2^{18}$, and $R_3^1$-$R_3^{14}$.

Light-emitting devices are self-emission display devices that have wide viewing angles, high contrast ratios, and short response times. Accordingly, light-emitting devices are receiving a lot of attention. Light-emitting devices are categorized into inorganic light-emitting devices (in which the emission layer includes an inorganic compound) and organic light-emitting devices (in which the emission layer includes an organic compound). Also, organic light-emitting devices are capable of displaying full-color images. In general, an organic light-emitting device has an anode/ organic emission layer/cathode stacked structure. Additionally, a hole injection layer and/or a hole transport layer and an electron injection layer may be further stacked between the anode and the emission layer or between the emission layer and the cathode. In the latter case, the organic light-emitting device may have an anode/hole transport layer/ organic emission layer/cathode structure, or an anode/hole transport layer/organic emission layer/electron transport layer/cathode structure.

Anthracene derivatives have been used as the material of the organic emission layer. For example, some organic light-emitting devices use a dimer or trimer compound of phenylanthracene. However, devices using this compound include two or three anthracenes linked through a conjugated system, and the organic light-emitting devices therefore have a narrow energy gap and low color purity of blue emission. Also, this compound is highly susceptible to oxidation and thus, impurities may be easily formed, which makes the purification process difficult. These problems may be reduced or overcome by developing an anthracene compound substituted with naphthalene at sites 1 and 9, and a diphenylanthracene compound substituted with an aryl group at the meta position of the phenyl groups. However, organic light-emitting devices using these compounds have low luminescent efficiency.

Also, organic light-emitting devices have used a naphthalene-substituted mono anthracene derivative. However, the luminescent efficiency of such an OLED is as low as 1 cd/A, and thus, the organic light-emitting device is not practical. Also, organic light-emitting devices have used compounds having a phenylanthracene structure. However, this compound is substituted with an aryl group at the meta position, and therefore, while organic light-emitting devices using this compound may have good heat resistance, they have luminescent efficiency characteristics as low as 2 cd/A.

A blue emission compound having a central diphenylanthracene structure and a terminal aryl group has been used as blue emission material, and organic light-emitting devices have used such blue emission compounds. However, the luminescent efficiency and brightness of such organic light-emitting devices are not satisfactory. Also, although organic light-emitting devices have used a substituted pyrene-based compound, the blue color purity of such OLEDs is low, and thus, it is difficult to display deep blue and to achieve a full-color display.

The compounds represented by Formulae 1, 2, and 3, described above, act as an emission material for an organic light-emitting device. Also, the compounds represented by Formulae 1, 2, and 3 have high glass transition temperatures (Tg) or high melting points, due to the introduction of a hetero ring. Accordingly, the durability under high temperatures, and the heat resistance against Joule's heat (which occurs within an organic layer, between organic layers, or between an organic layer and a metal electrode during emission) increase. An organic light-emitting device manufactured using a compound according to an embodiment of the present invention has high durability during storage and driving.

According to an embodiment of the present invention, the compound represented by Formula 1 may be represented by one of Formulae 4 to 7 below.

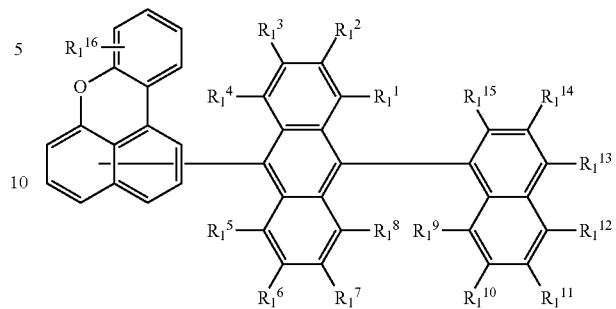

Formula 4

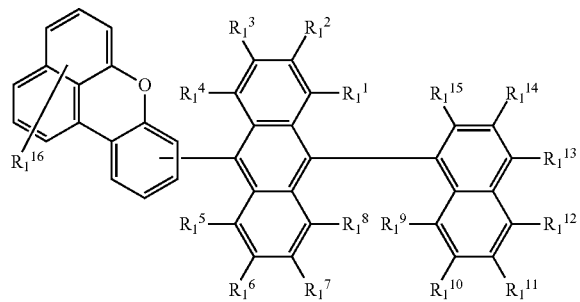

Formula 5

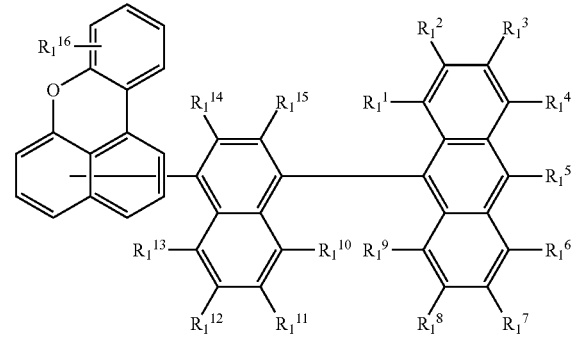

Formula 6

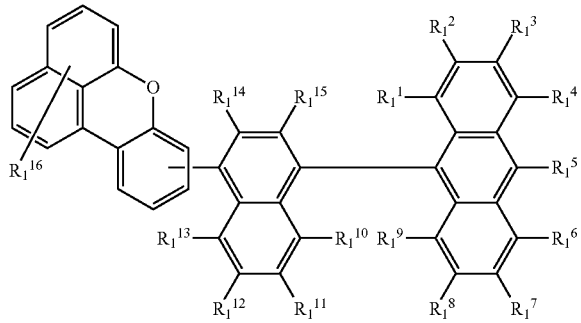

Formula 7

In Formulae 4 to 7, $R_1^1$ to $R_1^{16}$ are each independently a hydrogen atom, a deuterium atom, a halogen atom, a nitro group, a cyano group, a substituted or unsubstituted $C_1$ to $C_{60}$ alkyl group, a substituted or unsubstituted $C_2$ to $C_{60}$ alkenyl group, a substituted or unsubstituted $C_3$ to $C_{60}$ cycloalkyl group, a substituted or unsubstituted $C_6$ to $C_{60}$ aryl group, a substituted or unsubstituted $C_1$ to $C_{60}$ hetero aryl group, or a substituted or unsubstituted $C_6$ to $C_{60}$ condensed polycyclic group.

According to an embodiment of the present invention, the compound represented by Formula 2 may be represented by Formula 8 or 9 below.

Formula 8

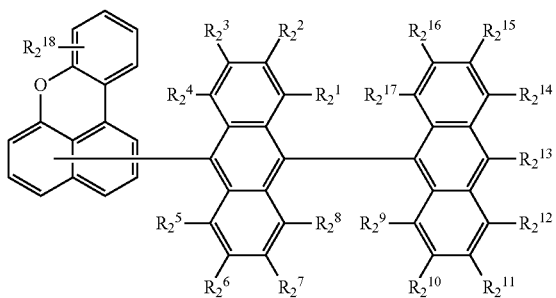

Formula 9

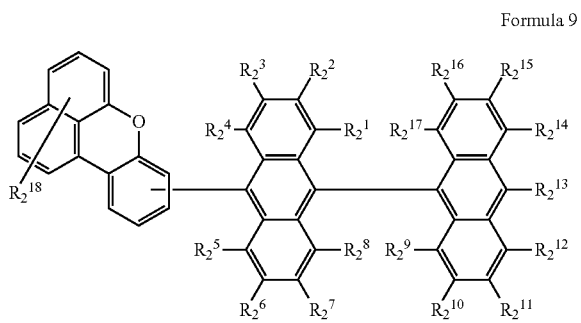

In Formulae 8 and 9, $R_2^1$ to $R_2^{18}$ are each independently a hydrogen atom, a deuterium atom, a halogen atom, a nitro group, a cyano group, a substituted or unsubstituted $C_1$ to $C_{60}$ alkyl group, a substituted or unsubstituted $C_2$ to $C_{60}$ alkenyl group, a substituted or unsubstituted $C_3$ to $C_{60}$ cycloalkyl group, a substituted or unsubstituted $C_6$ to $C_{60}$ aryl group, a substituted or unsubstituted $C_1$ to $C_{60}$ hetero aryl group, or a substituted or unsubstituted $C_6$ to $C_{60}$ condensed polycyclic group.

According to an embodiment of the present invention, the compound represented by Formula 3 may be represented by Formulae 10 or 11 below.

Formula 10

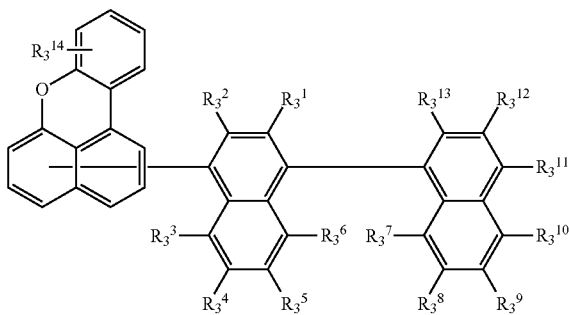

Formula 11

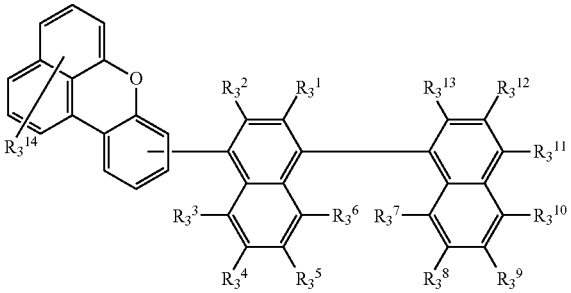

In Formulae 10 and 11, $R_3^1$ to $R_3^{14}$ are each independently a hydrogen atom, a deuterium atom, a halogen atom, a nitro group, a cyano group, a substituted or unsubstituted $C_1$ to $C_{60}$ alkyl group, a substituted or unsubstituted $C_2$ to $C_{80}$ alkenyl group, a substituted or unsubstituted $C_3$ to $C_{60}$ cycloalkyl group, a substituted or unsubstituted $C_6$ to $C_{60}$ aryl group, a substituted or unsubstituted $C_1$ to $C_{60}$ hetero aryl group, or a substituted or unsubstituted $C_6$ to $C_{60}$ condensed polycyclic group.

Substituents of the compounds of Formula 1 through Formula 11 will now be described.

According to an embodiment of the present invention, $R_1^1$, $R_1^2$, $R_1^8$, $R_1^9$, $R_1^{10}$, $R_1^{11}$, and $R_1^{16}$ of Formula 1, $R_2^1$, $R_2^2$, $R_2^8$, $R_2^9$, $R_2^{10}$, $R_2^{11}$, $R_2^{17}$, and $R_2^{18}$ of Formula 2, and $R_3^1$, $R_3^6$, $R_3^7$, $R_3^8$, $R_3^{13}$, and $R_3^{14}$ of Formula 3 may each independently be a hydrogen atom or a deuterium atom.

According to an embodiment of the present invention, $R_1^1$ to $R_1^{10}$, and $R_1^{15}$ of Formulae 4 and 5, and $R_1^1$ to $R_1^4$, $R_1^6$ to $R_1^{11}$, and $R_1^{15}$ of Formulae 6 and 7 may each independently be a hydrogen atom or a deuterium atom.

According to an embodiment of the present invention, $R_2^1$ to $R_2^{10}$, $R_2^{16}$, and $R_2^{17}$ of Formulae 8 and 9 may each independently be a hydrogen atom or a deuterium atom.

According to an embodiment of the present invention, $R_3^1$ to $R_3^8$, and $R_3^{13}$ of Formulae 10 and 11 may each independently be a hydrogen atom or a deuterium atom.

According to an embodiment of the present invention, $R_1^1$-$R_1^{16}$, $R_2^1$-$R_2^{18}$, $R_3^1$-$R_3^{14}$, and $R_0$ of Formulae 1, 2, and 3, $R_1^{13}$ and $R_8^{16}$ of Formulae 4 and 5, $R_1^5$ and $R_1^{16}$ of Formulae 6 and 7, $R_2^{13}$ and $R_2^{18}$ of Formulae 8 and 9, and $R_3^{11}$ and $R_3^{14}$ of Formulae 10 and 11 may each independently be a hydrogen atom, a deuterium atom, a cyano group, a trihalomethyl group, or any one of Formulae 2a to 2c below.

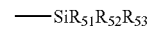

2a

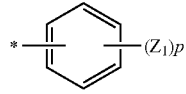

2b

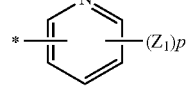

2c

In Formulae 2a through 2c, $R_{51}$, $R_{52}$, $R_{53}$, and $Z_1$ are each independently a hydrogen atom, a deuterium atom, a substituted or unsubstituted $C_1$ to $C_{20}$ alkyl group, a substituted or unsubstituted $C_6$ to $C_{20}$ aryl group, a substituted or unsubstituted $C_2$ to $C_{20}$ heteroaryl group, a substituted or unsubstituted $C_6$ to $C_{20}$ condensed polycyclic group, an amino group substituted with a $C_6$ to $C_{20}$ aryl group or a $C_2$ to $C_{20}$ heteroaryl group, a halogen atom, a cyano group, a nitro group, a hydroxyl group, or a carboxyl group. Also, p is an integer of 1 to 5, and * indicates a binding site to one of Formulae 1 through 11.

Definitions of representative substituents will now be presented. However, if is understood that the number of carbon atoms listed for a particular substituent is not limiting, and therefore does not limit the properties of the substituent. Also, unless defined otherwise, the definitions of the substituents are consistent with the general definitions of those terms, as would be understood by those of ordinary skill in the art.

As used herein, the unsubstituted $C_1$ to $C_{60}$ alkyl group may be a linear or branched alkyl group. Non-limiting examples thereof include a methyl group, an ethyl group, a propyl group, an isobutyl group, a sec-butyl group, a pentyl group, an iso-amyl group, a hexyl group, a heptyl group, an octyl group, a nonanyl group, and a dodecyl group. The substituted $C_1$ to $C_{60}$ alkyl group refers to the substitution of at least one hydrogen atom of the alkyl group with a deuterium atom, a halogen atom, a hydroxyl group, a nitro group, a cyano group, an amino group, an amidino group, a hydrazine group, a hydrazone group, a carboxyl group or salt thereof, a sulfonic acid group or salt thereof, a phosphoric acid group or salt thereof, a $C_1$ to $C_{10}$ alkyl group, a $C_1$ to $C_{10}$ alkoxy group, a $C_2$ to $C_{10}$ alkenyl group, a $C_2$ to $C_{10}$ alkynyl group, a $C_6$ to $C_{16}$ aryl group, or a $C_2$ to $C_{16}$ heteroaryl group.

As used herein, the unsubstituted $C_2$ to $C_{60}$ alkenyl group refers to an unsubstituted alkyl group having one or more carbon-carbon double bonds at the center or a terminal end. Non-limiting examples thereof include ethenyl, propenyl, and butenyl. The substituted $C_2$ to $C_{60}$ alkenyl group refers to the substitution of at least one hydrogen atom of the unsubstituted alkenyl group with the substituents described above in connection with the substituted alkyl group.

As used herein, the unsubstituted $C_2$ to $C_{60}$ alkynyl group refers to an unsubstituted alkyl group having one or more carbon-carbon triple bonds at the center or terminal end. Non-limiting examples thereof include acetylene, propylene, phenylacetylene, naphthylacetylene, isopropylacetylene, t-butylacetylene, and diphenylacetylene. The substituted $C_2$ to $C_{60}$ alkynyl group refers to the substitution of at least one hydrogen atom of the unsubstituted alkynyl group with the substituents described above in connection with the substituted alkyl group.

As used herein, the unsubstituted $C_3$ to $C_{60}$ cycloalkyl group refers to a $C_3$ to $C_{60}$ cyclic alkyl group. The substituted $C_3$ to $C_{60}$ cycloalkyl group refers to the substitution of at least one hydrogen atom of the cycloalkyl group with the substituents described above in connection with the $C_1$ to $C_{60}$ alkyl group.

As used herein, the unsubstituted $C_1$ to $C_{60}$ alkoxy group refers to a group represented by —OA where A is the unsubstituted $C_1$ to $C_{60}$ alkyl group. Non-limiting examples thereof include ethoxy, ethoxy, isopropyloxy, butoxy, and pentoxy. The substituted $C_1$ to $C_{60}$ alkoxy group refers to the substitution of at least one hydrogen atom of the unsubstituted alkoxy group with the substituents described above in connection with the alkyl group.

As used herein, the unsubstituted $C_6$ to $C_{60}$ aryl group refers to a carbocyclic aromatic system having at least one aromatic ring. When the number of rings is two or more, the rings may be fused to each other or may be linked to each other via, for example, a single bond. The term 'aryl' includes aromatic systems, such as phenyl, naphthyl, or anthracenyl. The substituted $C_6$ to $C_{60}$ aryl group refers to the substitution of at least one hydrogen atom of the aryl group with the substituents described above in connection with the $C_1$ to $C_{60}$ alkyl group.

Non-limiting examples of a substituted or unsubstituted $C_6$ to $C_{60}$ aryl group include a phenyl group, a $C_1$ to $C_{10}$ alkylphenyl group (for example, an ethylphenyl group), a biphenyl group, a $C_1$ to $C_{10}$ alkylbiphenyl group, a $C_1$ to $C_{10}$ alkoxybiphenyl group, o-, m-, and p-tolyl groups, o-, m- and p-cumenyl groups, a mesityl group, a phenoxyphenyl group, a ($\alpha,\alpha$-dimethylbenzene)phenyl group, a (N,N'-dimethyl) aminophenyl group, a (N,N'-diphenyl)aminophenyl group, a pentalenyl group, an indenyl group, a naphthyl group, a $C_1$ to $C_{10}$ alkylnaphthyl group (for example, methylnaphthyl group), a $C_1$ to $C_{10}$ alkoxynaphthyl group (for example, methoxynaphthyl group), an anthracenyl group, an azulenyl group, a heptalenyl group, an acenaphthalenyl group, a phenalenyl group, a fluorenyl group, an anthraquinolinyl group, a methylanthryl group, a phenanthryl group, a triphenylenyl group, a pyrenyl group, a chrysenyl group, an ethyl-chrysenyl group, a picenyl group, a perylenyl group, a chloroperylenyl group, a pentaphenyl group, a pentacenyl group, a tetraphenylenyl group, a hexaphenyl group, a hexacenyl group, a rubicenyl group, a coronenyl group, trinaphthalenyl group, a heptaphenyl group, a heptacenyl group, a pyranthrenyl group, and an ovalenyl group.

As used herein, the unsubstituted $C_1$-$C_{60}$ heteroaryl group refers to an aryl group (as defined above) that includes at least one ring hetero atom, such as nitrogen (N), oxygen (O), phosphorous (P), or sulfur (S). When the heteroaryl group has two or more rings, the rings may be fused to each other or may be linked to each other via, for example, a single bond. Non-limiting examples of the unsubstituted $C_1$-$C_{60}$ heteroaryl group include a pyrazolyl group, an imidazolyl group, a oxazolyl group, a thiazolyl group, a triazolyl group, a tetrazolyl group, an oxadiazolyl group, a pyridinyl group, a pyridazinyl group, a pyrimidinyl group, a triazinyl group, a carbazolyl group, an indolyl group, a quinolinyl group, an isoquinolinyl group, and a dibenzothiophenyl group. The substituted $C_1$-$C_{60}$ heteroaryl group refers to the substitution of at least one hydrogen atom of the heteroaryl group with the substituents described above in connection with the $C_1$ to $C_{60}$ alkyl group.

As used herein, the unsubstituted $C_6$ to $C_{60}$ aryloxy group refers to a group represented by —$OA_1$, where $A_1$ is the $C_6$ to $C_{60}$ aryl group. A non-limiting example of the aryloxy group is a phenoxy group. The substituted $C_6$ to $C_{60}$ aryloxy group refers to the substitution of at least one hydrogen atom of the aryloxy group with the substituents described above in connection with the $C_1$ to $C_{60}$ alkyl group.

As used herein, the $C_6$ to $C_{60}$ unsubstituted arylthio group refers to a group represented by —$SA_1$, where $A_1$ is the $C_6$ to $C_{60}$ aryl group. Non-limiting examples of the arylthio group include a benzenethio group and a naphthylthio group. The substituted arylthio group refers to the substitution of at least one hydrogen atom of the arylthio group with the substituents described above in connection with the $C_1$ to $C_{60}$ alkyl group.

As used herein, the unsubstituted $C_6$ to $C_{60}$ condensed polycyclic group refers to a substituent having two or more rings formed by fusing at least one aromatic ring and/or at least one non-aromatic ring, or to a substituent in which an unsaturated group is present in a ring but that is not a conjugated system. The condensed polycyclic group does not have overall aromaticity, which is how the condensed polycyclic group is distinguished from the aryl group or the heteroaryl group.
Non-limiting examples of compounds represented by Formula 1, Formula 2, and Formula 3 include Compounds 1-66 below.
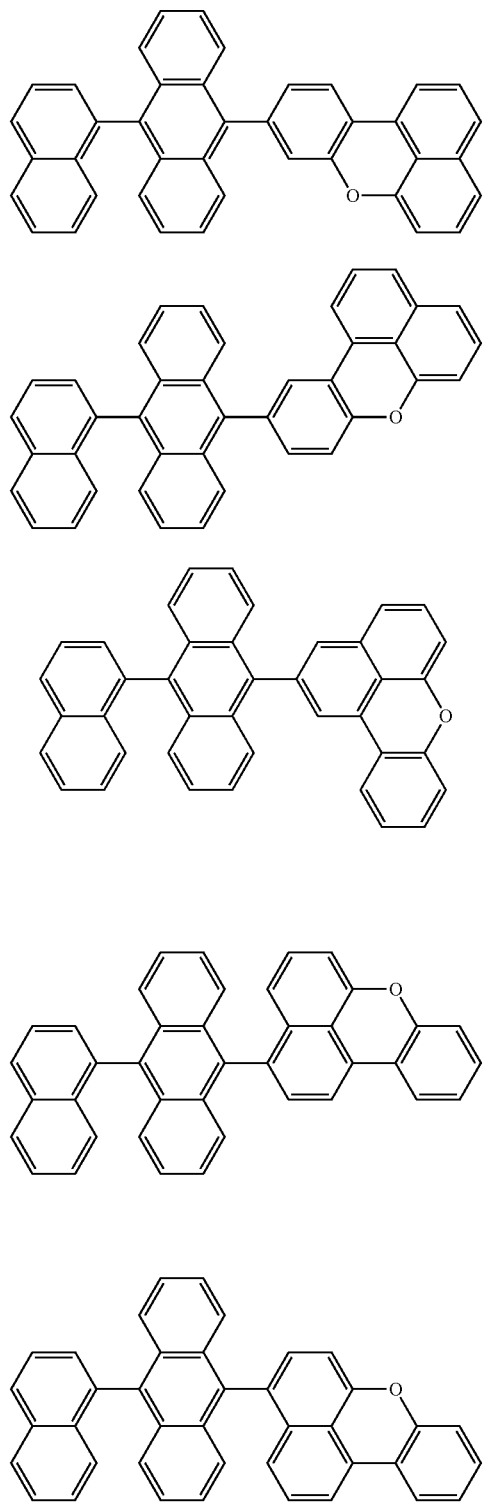
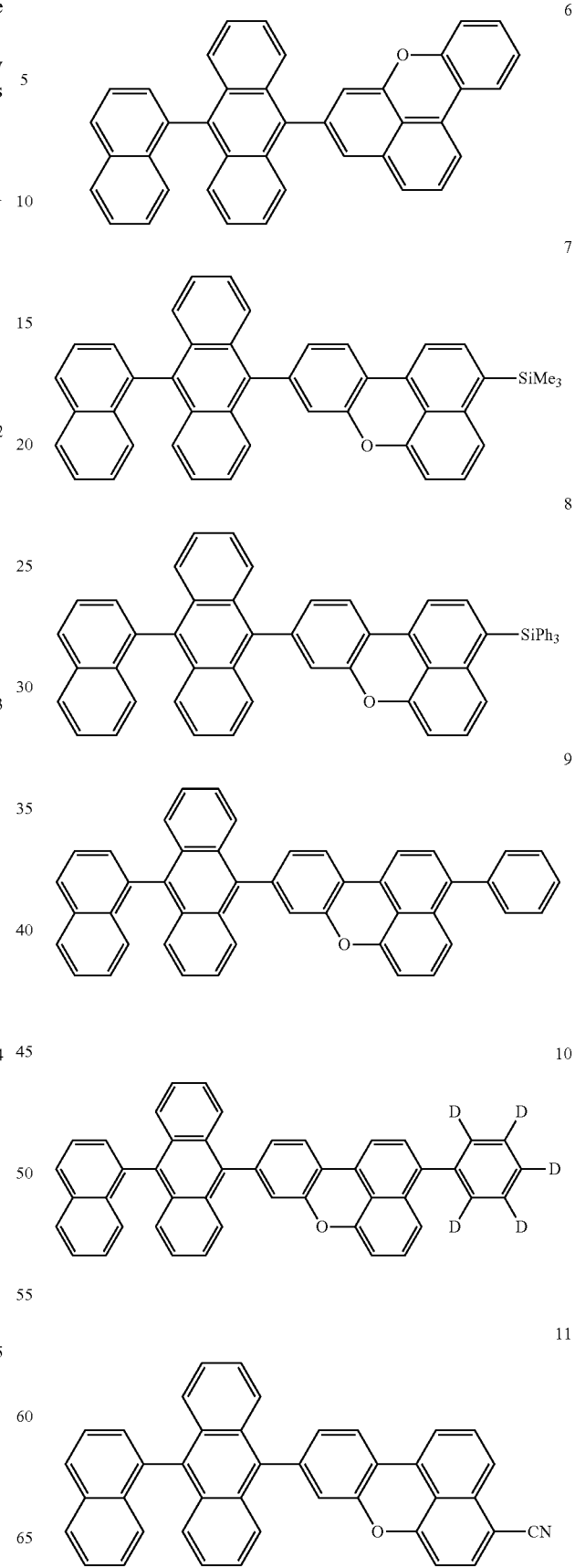

12
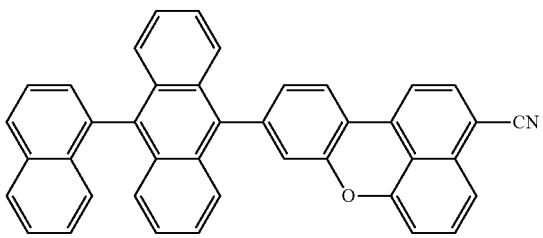
13
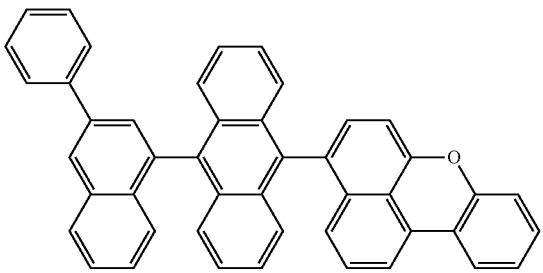
14
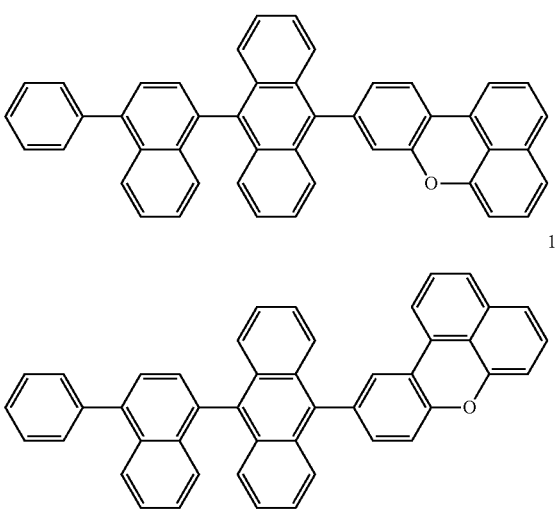
18
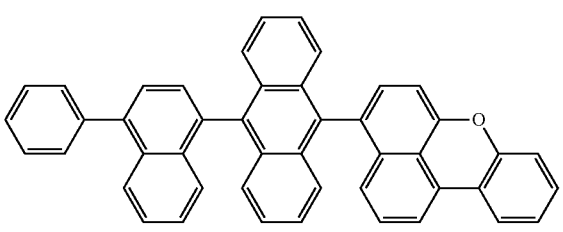
19
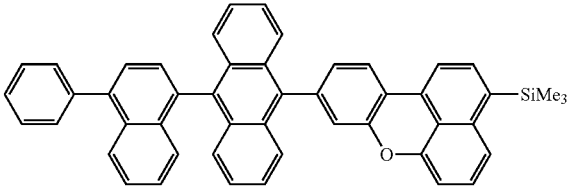
20
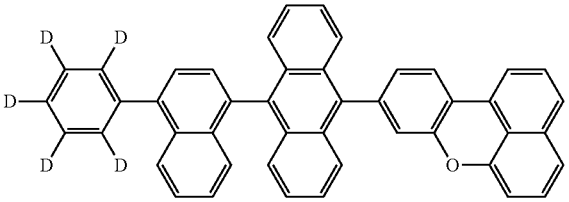
21
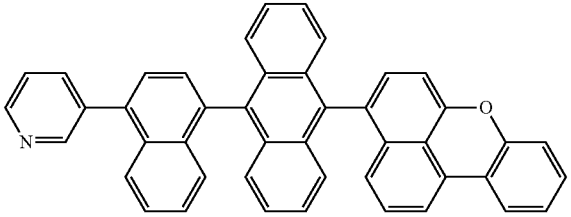
22
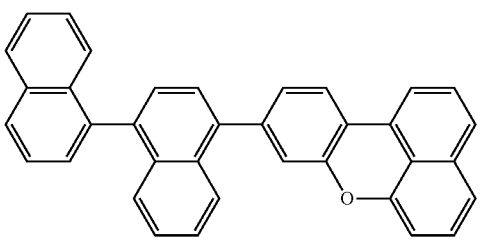
23
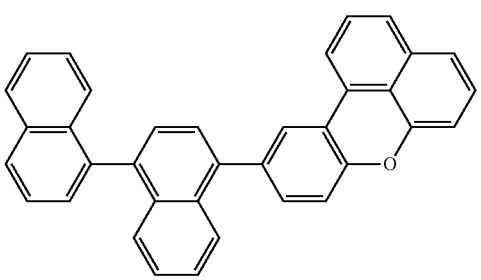

-continued
24
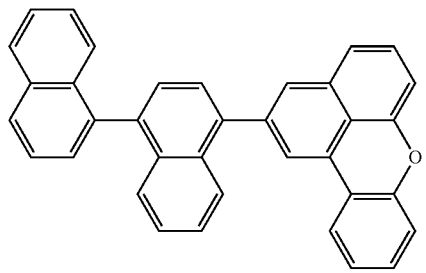
25
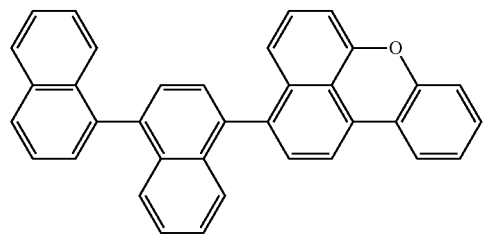
26
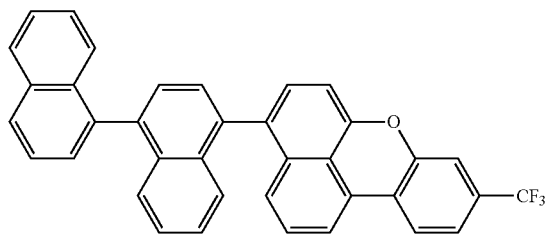
27
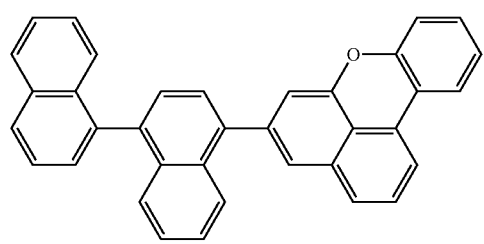
28
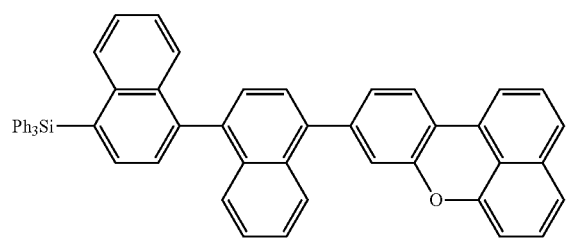
29
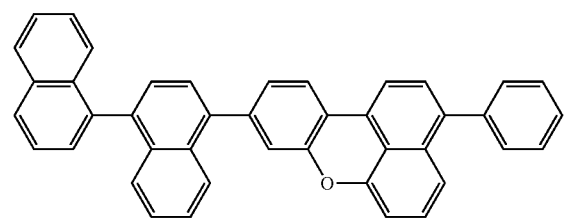
-continued
30
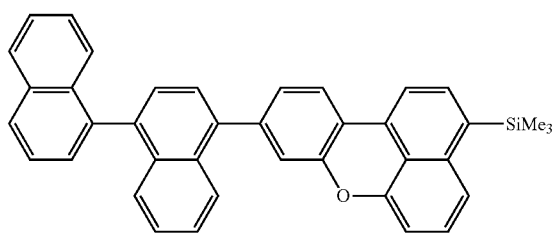
31
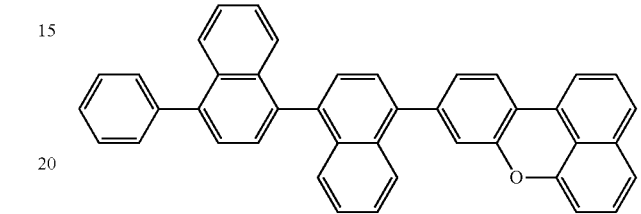
32
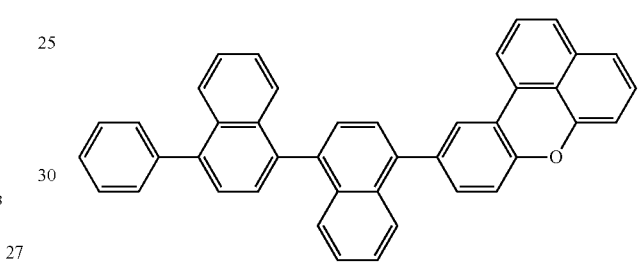
33
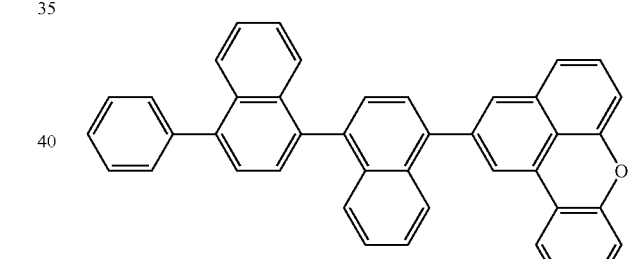
34
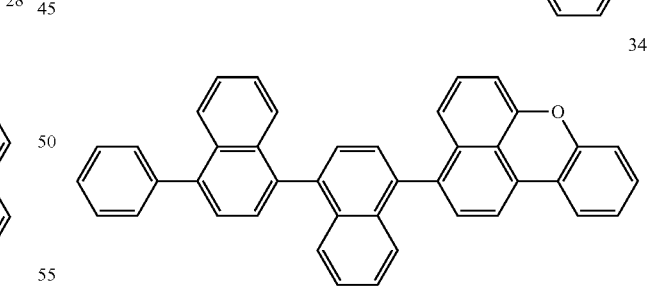
35
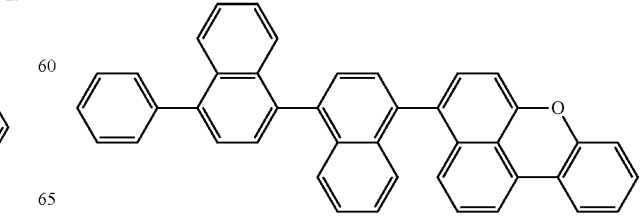

36
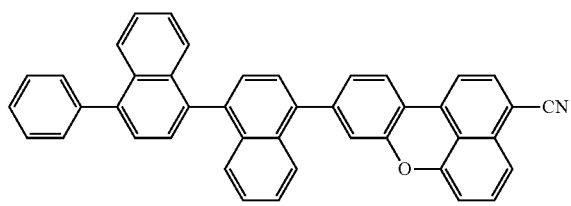
37
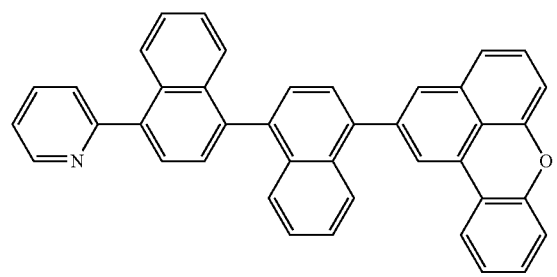
38
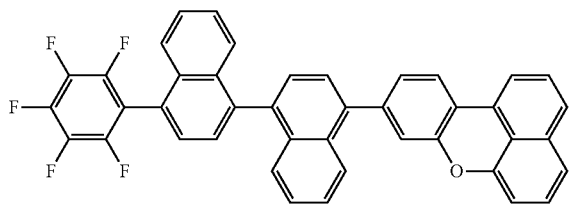
39
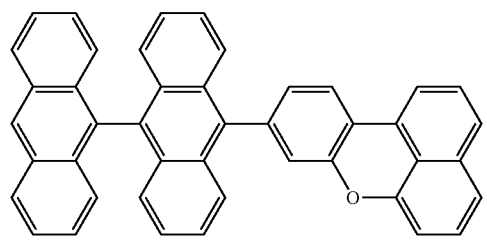
40
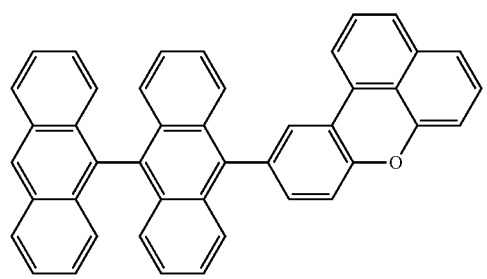
41
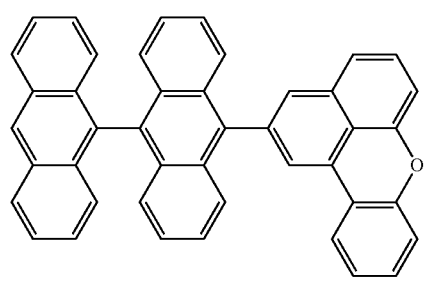
42
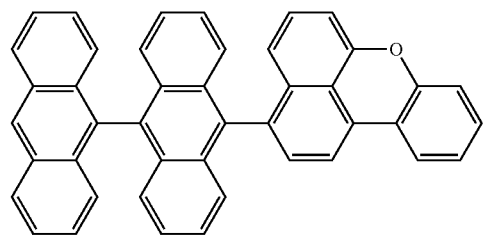
43
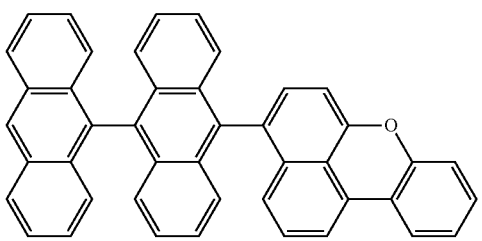
44
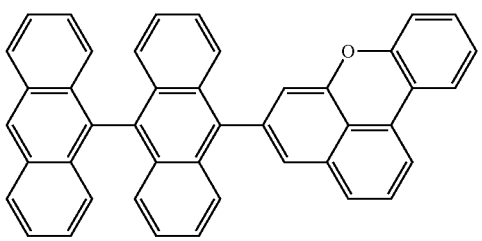
45
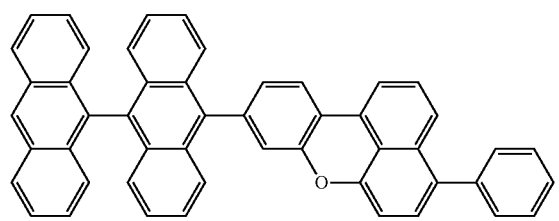
46
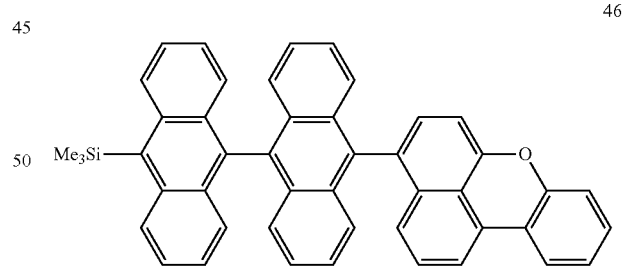
47
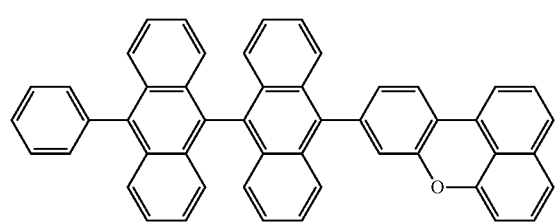

48
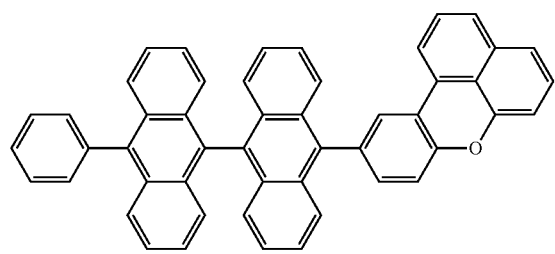
49
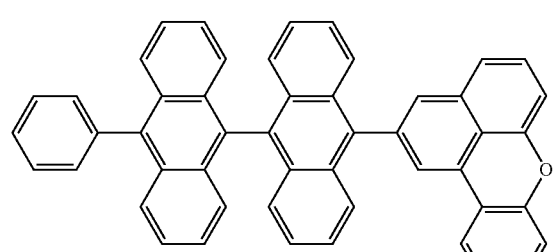
50
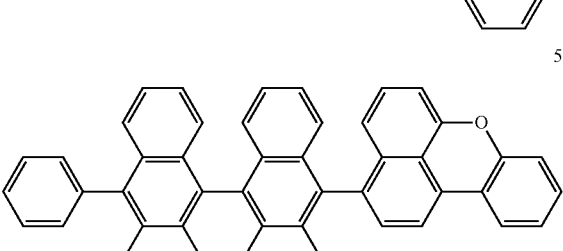
51
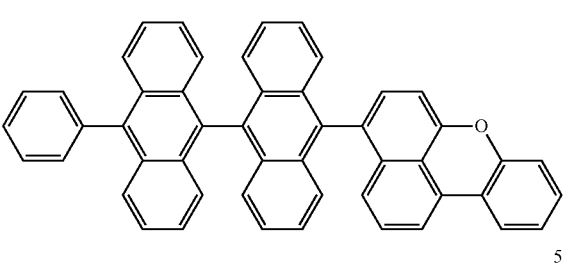
52
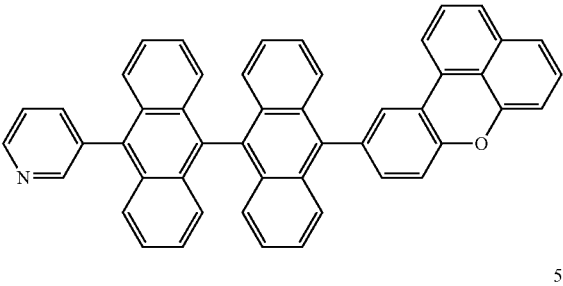
53
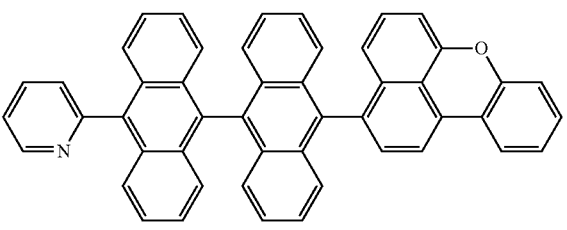
54
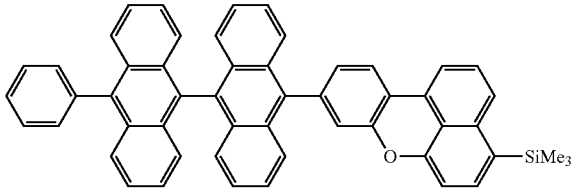
55
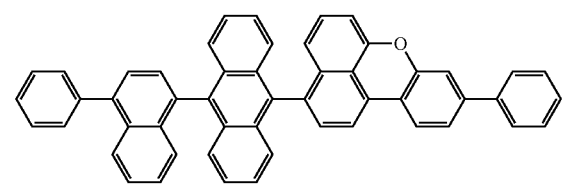
56
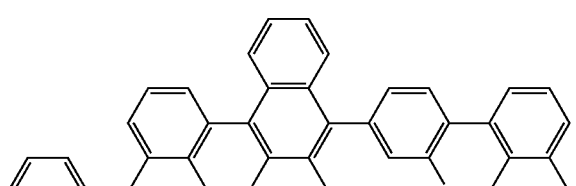
57
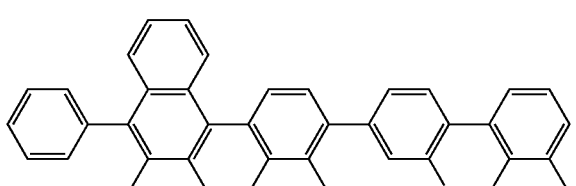
58
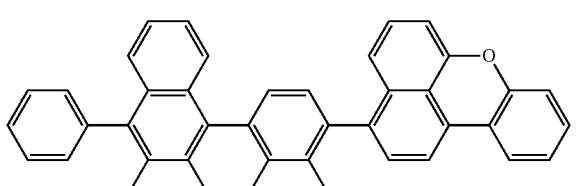
59
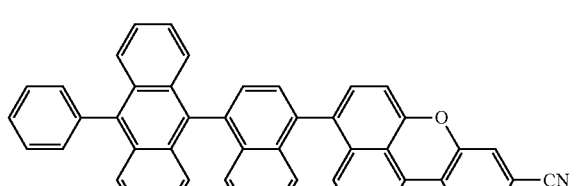
60
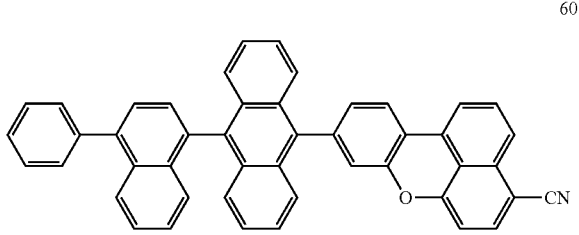

-continued

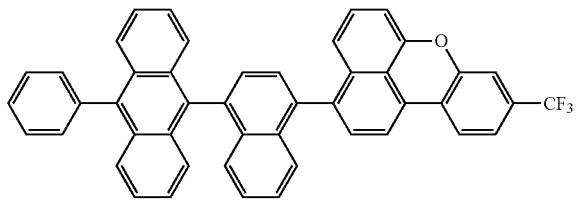
61

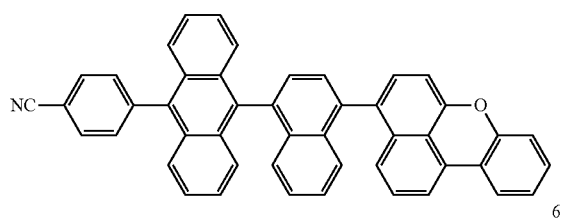
62

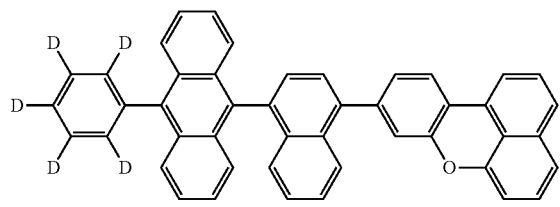
63

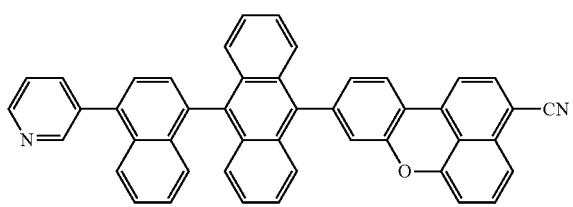
64

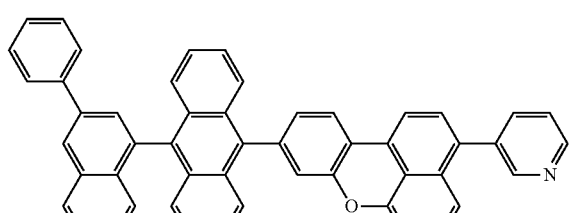
65

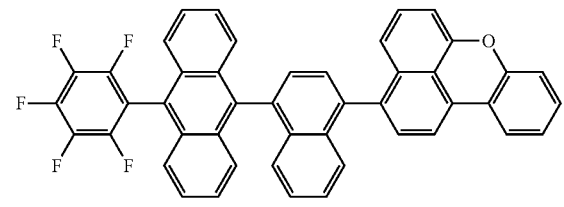
66

An organic light-emitting device according to an embodiment of the present invention includes a first electrode, a second electrode, and an organic layer between the first electrode and the second electrode. The organic layer includes the compound represented by any one of Formulae 1-9, discussed above.

The organic layer may include at least one of a hole injection layer, a hole transport layer, a functional layer having a hole injection function and a hole transport function (hereinafter referred to as an "H-functional layer"), a buffer layer, an electron blocking layer, an emission layer, a hole blocking layer, an electron transport layer, an electron injection layer, and/or a functional layer having an electron transport function and an electron injection function (hereinafter referred to as an "E-functional layer").

For example, the organic layer may be an emission layer, an electron injection layer, an electron transport layer, and/or a functional layer having electron injection capability and electron transportation capability. For example, the organic layer may be a blue emission layer or an electron injection layer.

According to an embodiment of the present invention, the organic layer may further include an electron injection layer, an electron transport layer, a functional layer having electron injection capability and electron transportation capability, an emission layer, a hole injection layer, a hole transport layer, or a functional layer having hole injection capability and hole transportation capability. The emission layer may include an anthracene-based compound, an arylamine-based compound, or a styryl-based compound.

According to another embodiment of the present invention, the organic layer may include an electron injection layer, an electron transport layer, a functional layer having electron injection capability and electron transportation capability, an emission layer, a hole injection layer, a hole transport layer, or a functional layer having hole injection capability and hole transportation capability. The emission layer may include a red layer, a green layer, a blue layer, and a white layer, and any one of these layers may include a phosphorescent compound. The hole injection layer, the hole transport layer, or the functional layer having hole injection capability and hole transportation capability may include a charge-generation material. The charge-generation material may be a p-dopant, and the p-dopant may be a quinone derivative, a metal oxide, or a cyano group-containing compound.

According to another embodiment of the present invention, the organic layer may include an electron transport layer that includes an electron-transportable organic compound and a metal complex. The metal complex may be a Li complex.

The term "organic layer," as used herein, refers to a single layer and/or a plurality of layers between the first electrode and the second electrode of an organic light-emitting device.

The organic layer includes an emission layer, and the emission layer may include the compound represented by Formula 1. The organic layer may include at least one additional layer, such as, for example, a hole injection layer, a hole transport layer, or a H-functional layer. The at least one additional layer (e.g., a hole injection layer, a hole transport layer, or a H-functional layer) may include the compound.

The FIGURE is a schematic cross-sectional view of an organic light-emitting device according to an embodiment of the present invention. The structure of an organic light-emitting device according to an embodiment of the present invention, and a method of manufacturing the organic light-emitting device according to an embodiment of the present invention, will be described with reference to the FIGURE.

A substrate (not shown) of the OLED may be any one of various substrates commonly used in organic light-emitting devices, and may be, for example, a glass substrate or a transparent plastic substrate with mechanical strength, thermal stability, transparency, surface smoothness, ease of handling, and water resistance.

A first electrode may be formed on the substrate by depositing or sputtering a first electrode material on the substrate. When the first electrode is an anode, the first electrode material may be selected from materials having a high work function to facilitate easy hole injection. The first electrode may be a reflective electrode or a transmission (i.e., transparent) electrode. The first electrode material may be a transparent material with high conductivity, non-limiting examples of which include indium tin oxide (ITO), indium zinc oxide (IZO), tin oxide ($SnO_2$), and zinc oxide (ZnO). According to an embodiment of the present invention, the first electrode may be formed as a reflective electrode using magnesium (Mg), aluminum (Al), aluminum-lithium (Al—Li), calcium (Ca), magnesium-indium (Mg—In), or magnesium-silver (Mg—Ag).

The first electrode may be a single- or multi-layered structure. For example, the first electrode may have a three-layered structure, e.g., ITO/Ag/ITO, but the structure of the first electrode is not limited thereto.

An organic layer is disposed on the first electrode. The organic layer may include a hole injection layer, a hole transport layer, a buffer layer (not shown), an emission layer, an electron transport layer, or an electron injection layer.

The hole injection layer (HIL) may be formed on the first electrode by various methods, such as vacuum deposition, spin coating, casting, LB deposition, or the like. When the HIL is formed by vacuum deposition, the deposition conditions may vary according to the material that is used to form the HIL, and the desired structural and thermal characteristics of the HIL. For example, the deposition conditions may include a deposition temperature of about 100 to about 500° C., a vacuum pressure of about $10^{-8}$ to about $10^{-3}$ torr, and a deposition rate of about 0.01 to about 100 Å/sec. However, the deposition conditions are not limited thereto.

When the HIL is formed using spin coating, the coating conditions may vary according to the material used to form the HIL, and the desired structural and thermal properties of the HIL. For example, the coating speed may be about 2000 rpm to about 5000 rpm, and the temperature at which heat treatment is performed to remove solvent after coating may be about 80° C. to about 200° C. However, the coating conditions are not limited thereto.

The hole injection material may be any suitable hole injection material, non-limiting examples of which include N,N'-diphenyl-N,N'-bis-[4-(phenyl-m-tolyl-amino)-phenyl]-biphenyl-4,4'-diamine (DNTPD), a phthalocyanine compound such as copper phthalocyanine, 4,4',4''-tris(3-methylphenylphenylamino)triphenylamine (m-MTDATA), N,N'-di(1-naphthyl)-N,N'-diphenylbenzidine (NPB), TDATA, 2-TNATA, a polyaniline/dodecylbenzenesulfonic acid (pani/DBSA), poly(3,4-ethylenedioxythiophene)/poly (4-styrenesulfonate) (PEDOT/PSS), polyaniline/camphor sulfonicacid (pani/CSA), and (polyaniline)/poly(4-styrenesulfonate) (PANI/PSS).

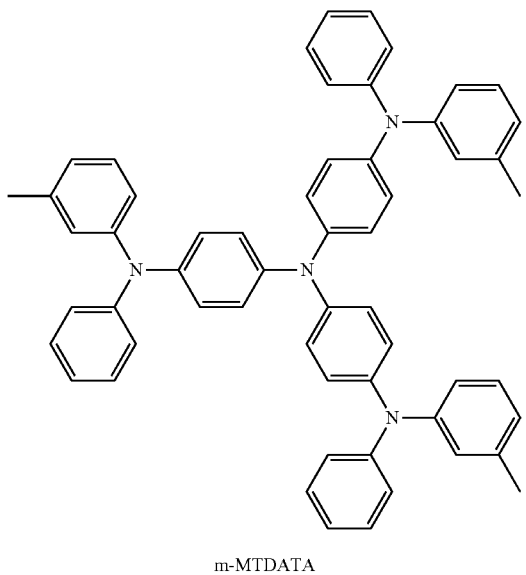

m-MTDATA

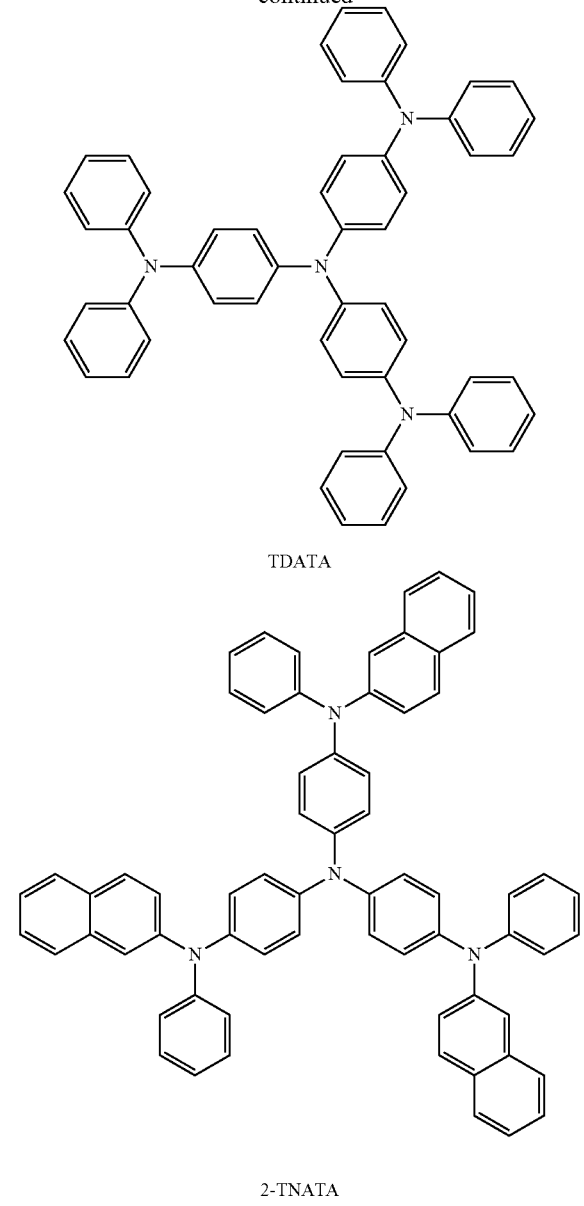

TDATA

2-TNATA

The thickness of the HIL may be about 100 Å to about 10,000 Å, for example, about 100 Å to about 1000 Å. When the thickness of the HIL is within either of these ranges, the HIL may have satisfactory hole injection characteristics without a substantial increase in a driving voltage.

Then, a hole transport layer (HTL) may be formed on the HIL by vacuum deposition, spin coating, casting, Langmuir-Blodgett (LB) deposition, or the like. When the HTL is formed using vacuum deposition or spin coating, the deposition or coating conditions may be similar to those used to form the HIL, though the conditions for deposition and coating may vary according to the material that is used to form the HTL.

The hole-transportation material may be any suitable hole transport material, non-limiting examples of which include a carbazole derivative, such as N-phenylcarbazole or polyvinylcarbazole, N,N'-bis(3-methylphenyl)-N,N'-diphenyl-[1,1-biphenyl]-4,4'-diamine (TPD), 4,4',4''-tris(N-carbazolyl)triphenylamine (TCTA), and N,N'-di(1-naphthyl)-N, N'-diphenylbenzidine (NPB).

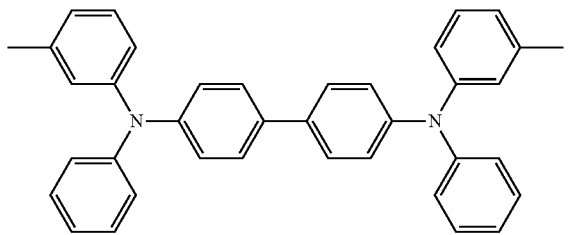

TPD

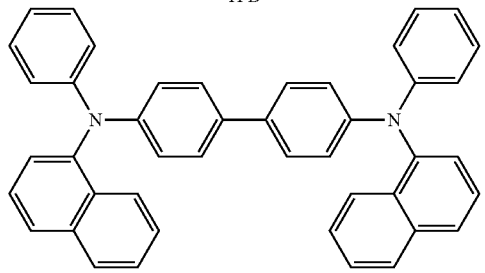

NPB

The thickness of the HTL may be about 50 Å to about 2,000 Å, for example, about 100 Å to about 1,500 Å. When the thickness of the HTL is within either of these ranges, the HTL may have satisfactory hole transportation properties without a substantial increase in a driving voltage.

An H-functional layer (i.e., a functional layer having a hole injection capability and a hole transport capability) may include one or more HIL materials and HTL materials. The thickness of the H-functional layer may be about 500 Å to about 10,000 Å, for example, about 100 Å to about 1,000 Å. When the thickness of the H-functional layer is within either of these ranges, satisfactory hole injection and transportation properties may be obtained without a substantial increase in driving voltage.

In addition, at least one of the HIL, the HTL, and the H-functional layer may include at least one of a compound represented by Formula 300 and a compound represented by Formula 350.

Formula 300

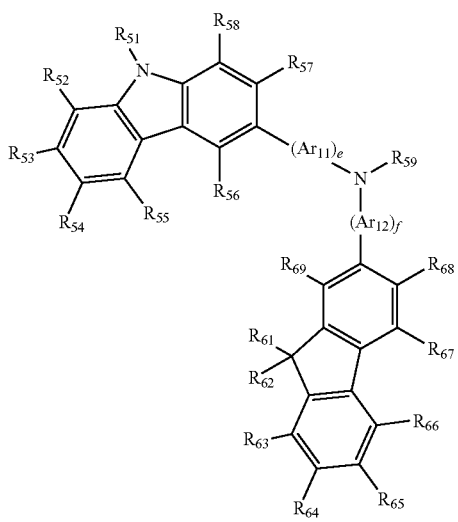

Formula 350

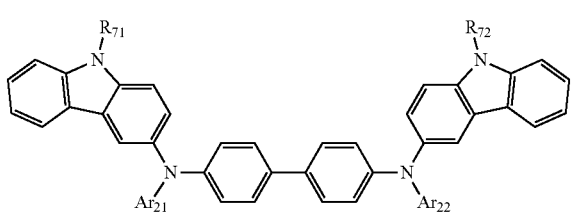

In Formulae 300 and 350, $Ar_{11}$, $Ar_{12}$, $Ar_{21}$, and $Ar_{22}$ are each independently a substituted or unsubstituted $C_5$-$C_{60}$ arylene group.

e and f in Formula 300 may each independently be an integer of 0 to 5, or 0, 1 or 2. For example, e may be 1 and f may be 0, but e and f are not limited thereto.

$R_{51}$ to $R_{58}$, $R_{61}$ to $R_{69}$, and $R_{71}$ and $R_{72}$ in Formulae 300 and 350 may each independently be a hydrogen atom, a deuterium atom, a halogen atom, a hydroxyl group, a cyano group, a nitro group, an amino group, an amidino group, hydrazine group, a hydrazone group, a carboxyl group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{60}$ cycloalkyl group, a substituted or unsubstituted $C_5$-$C_{60}$ aryl group, a substituted or unsubstituted $C_5$-$C_{60}$ aryloxy group, or a substituted or unsubstituted $C_5$-$C_{60}$ arylthio group. For example, $R_{51}$ to $R_{58}$, $R_{61}$ to $R_{69}$, $R_{71}$ and $R_{72}$ may each independently be a hydrogen atom; a deuterium atom; a halogen atom; a hydroxyl group; a cyano group; a nitro group; an amino group; an amidino group; a hydrazine group; a hydrazone group; a carboxyl group or a salt thereof; a sulfonic acid group or a salt thereof; a phosphoric acid group or a salt thereof; a $C_1$-$C_{10}$ alkyl group (for example, a methyl group, an ethyl group, a propyl group, a butyl group, a pentyl group, a hexyl group, or the like); a $C_1$-$C_{10}$ alkoxy group (for example, a methoxy group, an ethoxy group, a propoxy group, a butoxy group, a pentoxy group, or the like); a $C_1$-$C_{10}$ alkyl group or a $C_1$-$C_{10}$ alkoxy group substituted with at least one of a deuterium atom, a halogen atom, a hydroxyl group, a cyano group, a nitro group, an amino group, an amidino group, a hydrazine group, a hydrazone group, a carboxyl group or a salt thereof, a sulfonic acid group or a salt thereof, or a phosphoric acid group or a salt thereof; a phenyl group; a naphthyl group; an anthryl group; a fluorenyl group; a pyrenyl group; or a phenyl group, a naphthyl group, an anthryl group, a fluorenyl group, or a pyrenyl group substituted with at least one of a deuterium atom, a halogen atom, a hydroxyl group, a cyano group, a nitro group, an amino group, an amidino group, hydrazine, hydrazone, a carboxyl group or a salt thereof, a sulfonic acid group or a salt thereof, a phosphoric acid group or a salt thereof, a $C_1$-$C_{10}$ alkyl group, or a $C_1$-$C_{10}$ alkoxy group. However, $R_{51}$ to $R_{58}$, $R_{61}$ to $R_{69}$, $R_{71}$ and $R_{72}$ are not limited thereto.

$R_{59}$ in Formula 300 may be a phenyl group; a naphthyl group; an anthryl group; a biphenyl group; or a pyridyl group; or a phenyl group, a naphthyl group, an anthryl group, a biphenyl group, or a pyridyl group substituted with at least one of a deuterium atom, a halogen atom, a hydroxyl group, a cyano group, a nitro group, an amino group, an amidino group, hydrazine, hydrazone, a carboxyl group or a salt thereof, a sulfonic acid group or a salt thereof, a phosphoric acid group or a salt thereof, a substituted or unsubstituted $C_1$-$C_{20}$ alkyl group, or a substituted or unsubstituted $C_1$-$C_{20}$ alkoxy group.

According to an embodiment of the present invention, the compound represented by Formula 300 may be represented by Formula 300A, but the chemical structure of the compound is not limited thereto.

Formula 300A

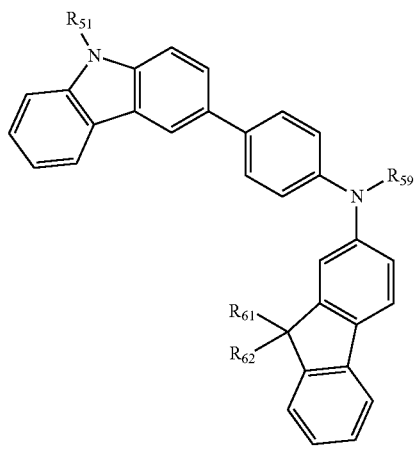

In Formula 300A, $R_{51}$, $R_{61}$, $R_{62}$, and $R_{59}$ are described above with respect to Formula 300.

In some exemplary embodiments, at least one of the HIL, the HTL, and the H-functional layer may include at least one of Compounds 301 to 320 below, but the HIL, HTL and H-functional layer are not limited thereto, and may include other materials.

301

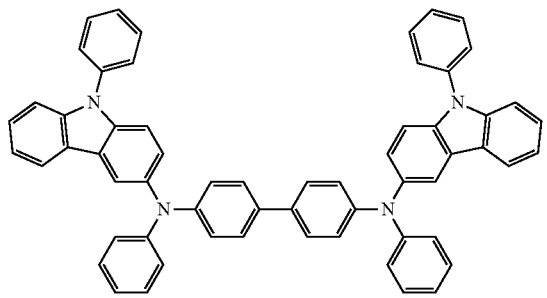

302

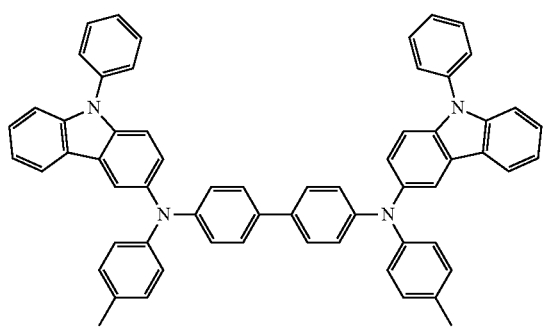

303

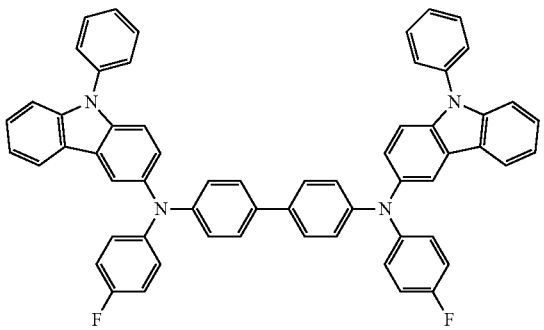

304

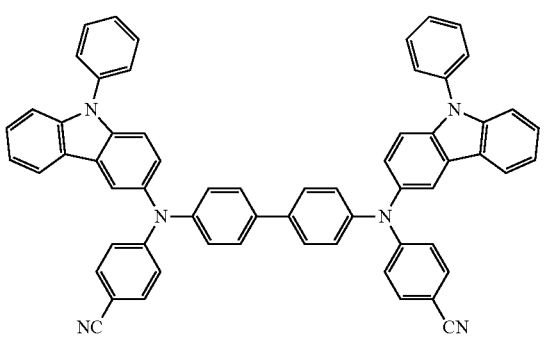

305

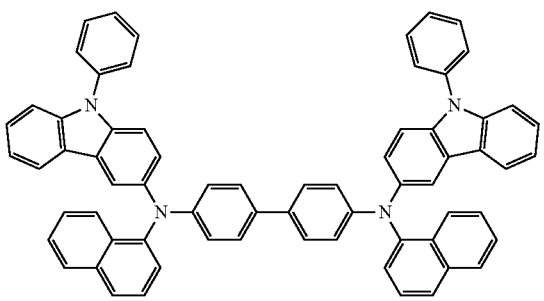

306

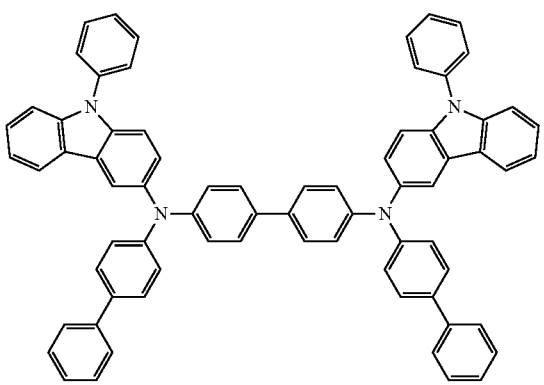

307
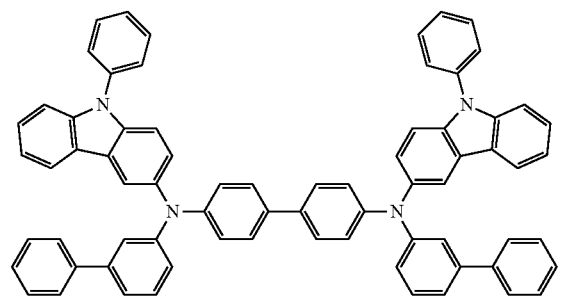
308
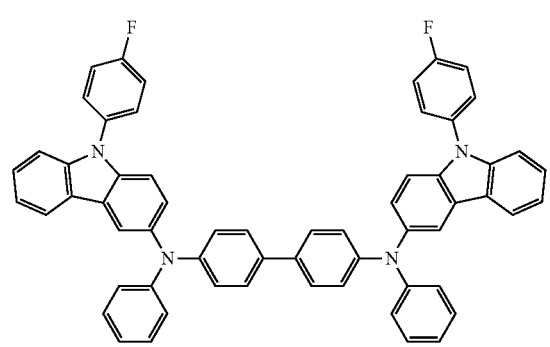
309
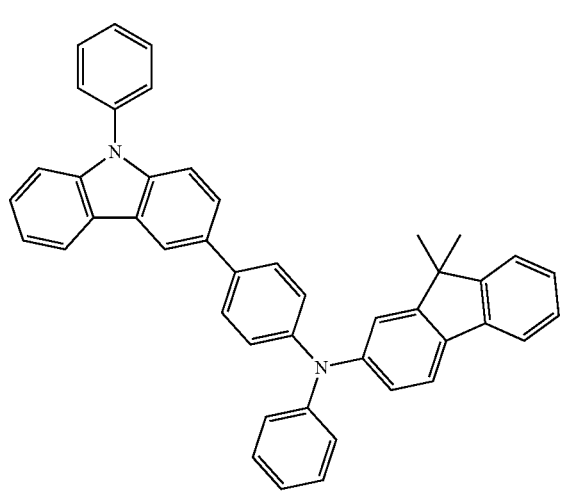
310
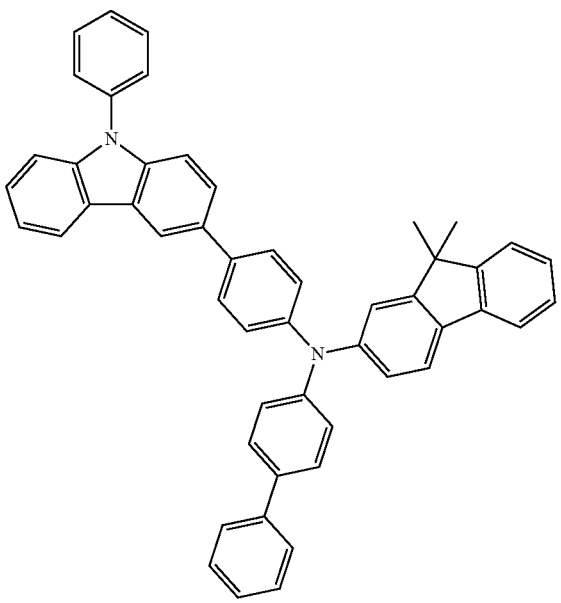
311

31
-continued
312
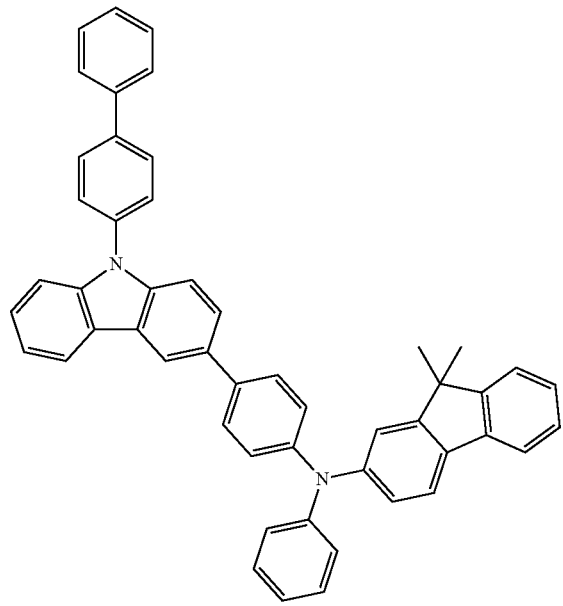
313
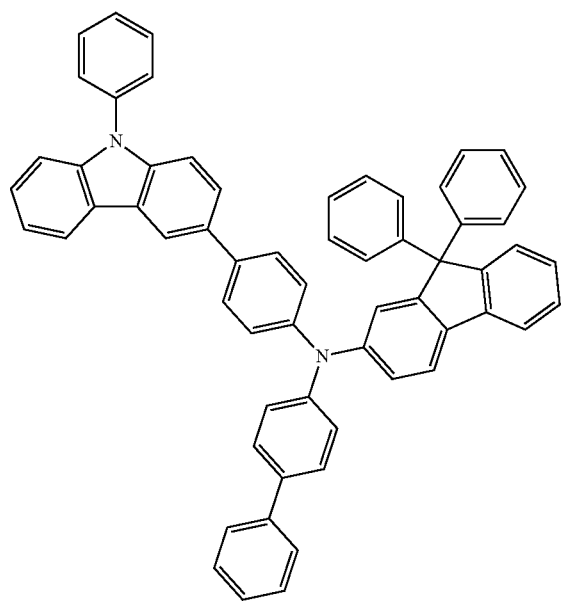
32
-continued
314
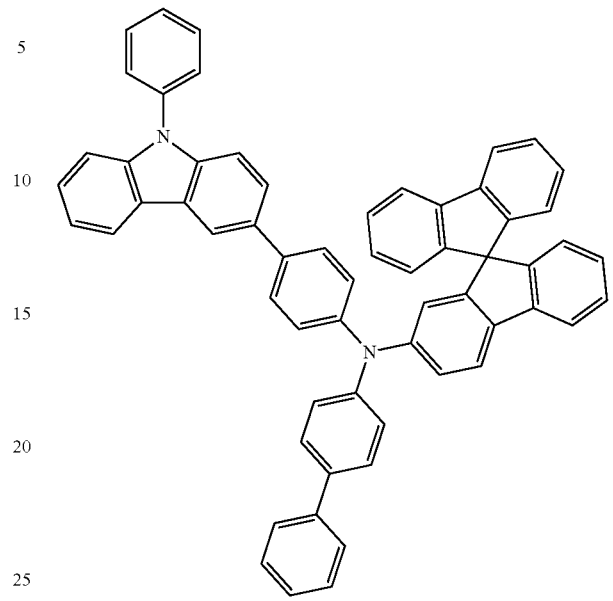
315
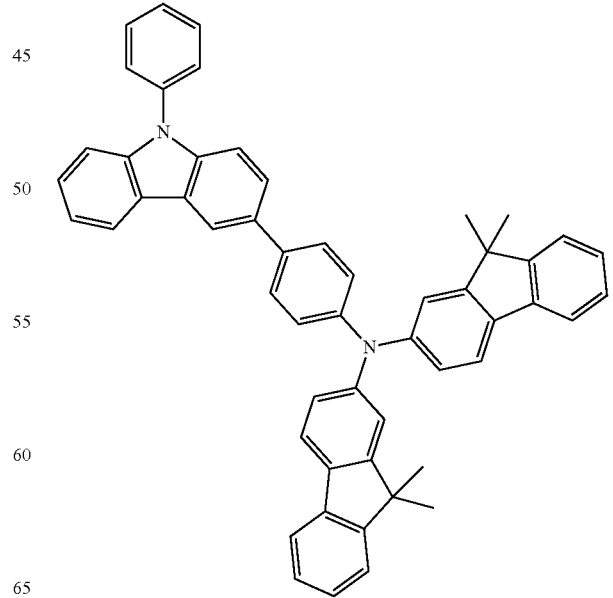

316

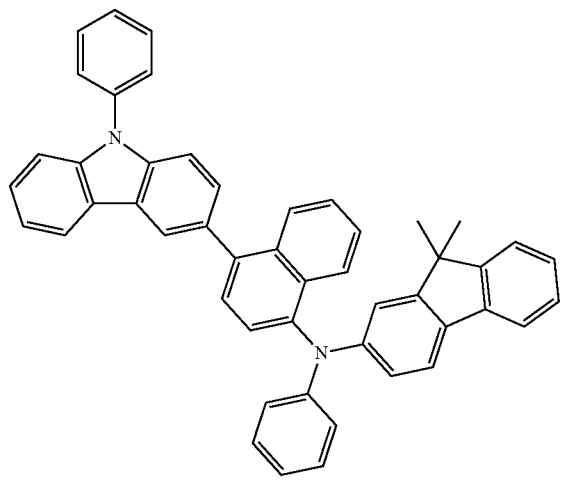

317

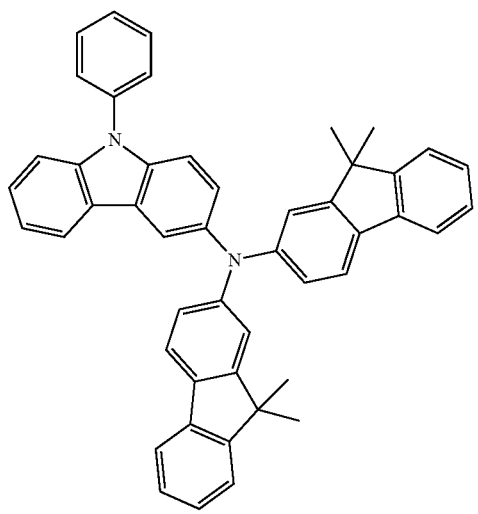

318

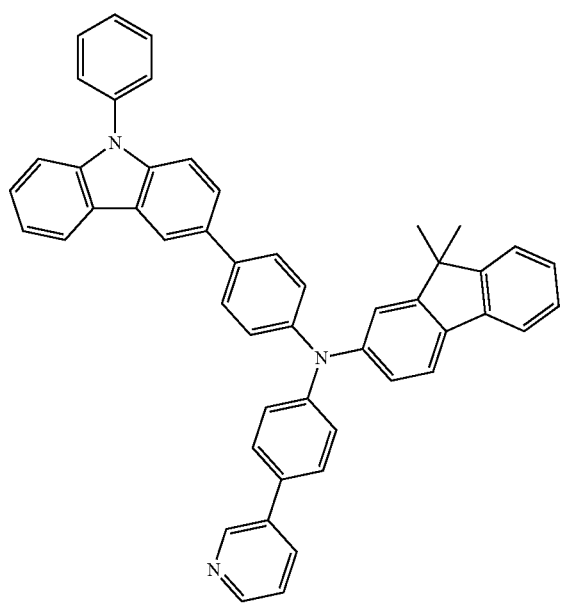

319

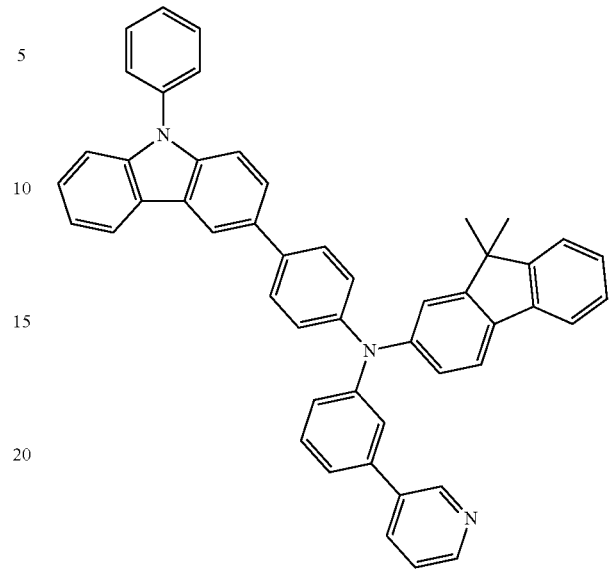

320

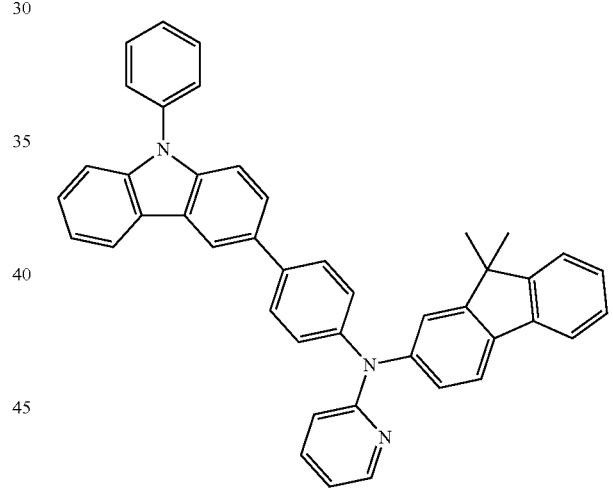

To increase conductivity of the layer, at least one of the HIL, the HTL, and the H-functional layer may further include a charge-generation material in addition to the hole injecting materials, hole transport materials, and/or materials having both hole injection and hole transport capabilities.

The charge-generation material may be, for example, a p-dopant. The p-dopant may be one of a quinone derivative, a metal oxide, or a cyano group-containing compound, but is not limited thereto. Non-limiting examples of the p-dopant include a quinone derivative, such as tetracyanoquinonedimethane (TCNQ) and 2,3,5,6-tetrafluoro-tetracyano-1,4-benzoquinonedimethane (F4-TCNQ), or the like; a metal oxide, such as a tungsten oxide or a molybdenum oxide; and a cyano group-containing compound, such as Compound 200.

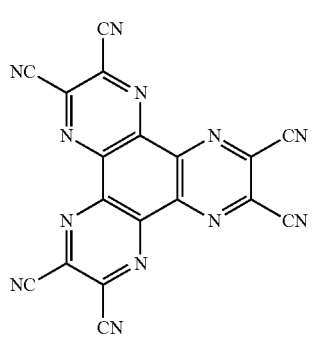

Compound 200

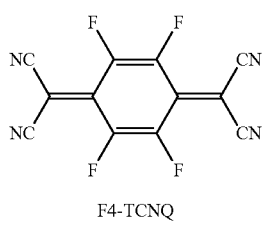

F4-TCNQ

When the HIL, the HTL or the H-functional layer further includes the charge-generation material, the charge-generation material may be homogeneously dispersed or non-homogeneously distributed in the HIL, the HTL, or the H-functional layer.

A buffer layer may be disposed between the emission layer and at least one of the HIL, the HTL, and the H-functional layer. The buffer layer may compensate for an optical resonance distance according to a wavelength of light emitted from the emission layer. As such, the efficiency of a resulting organic light-emitting device may be improved. The buffer layer may include a hole injection material and a hole transportation material. Also, the buffer layer may include a material that is the same as the material included in the hole injection layer, the hole transport layer, or the H-functional layer beneath the buffer layer.

Subsequently, an emission layer (EML) may be formed on the hole transport layer, the H-functional layer, or the buffer layer by vacuum deposition, spin coating, casting, LB deposition, etc. If the EML is formed by vacuum deposition or spin coating, the deposition or coating conditions may be similar to those used to form the HIL, although the deposition or coating conditions may vary according to the material that is used to form the EML.

The EML may include the compound according to an embodiment of the present invention, or various hosts and dopants. The dopant for use in the EML may be a fluorescent dopant or a phosphorescent dopant.

Non-limiting examples of suitable hosts include $Alq_3$, 4,4'-N,N'-dicarbazole-biphenyl (CBP), poly(n-vinylcarbazole)(PVK), 9,10-di(naphthalene-2-yl)anthracene (ADN), TCTA, 1,3,5-tris(N-phenylbenzimidazole-2-yl)benzene (TPBI), 3-tert-butyl-9,10-di(naphth-2-yl) anthracene (TBADN), E3, distyrylarylene (DSA), dmCBP (see the following chemical structure), Compounds 501 to 509 illustrated below, or the like. However, other materials may also be used as the host.

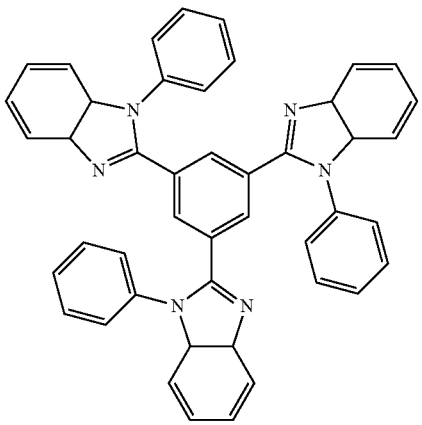

TPBI

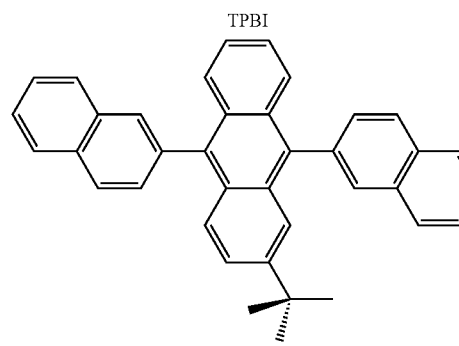

TBADN

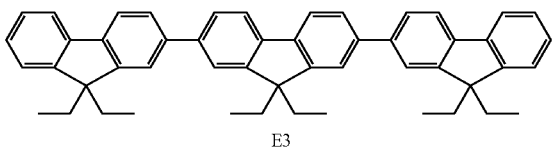

E3

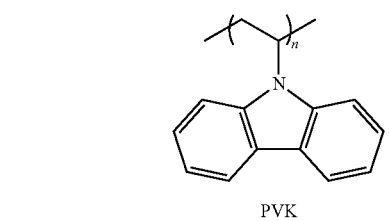

PVK

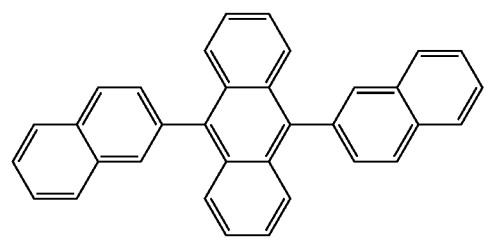

ADN

CBP
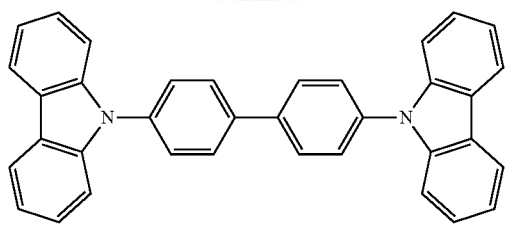
dmCBP
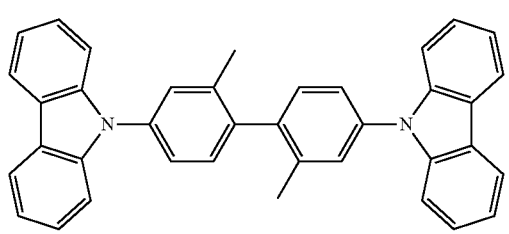
501
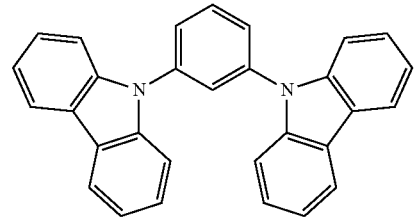
502
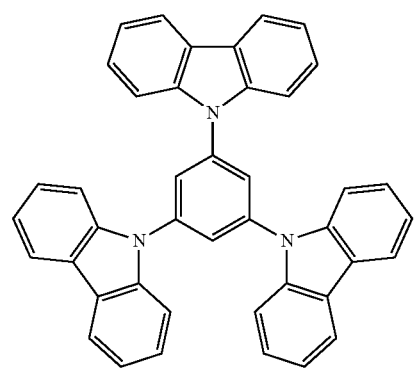
503
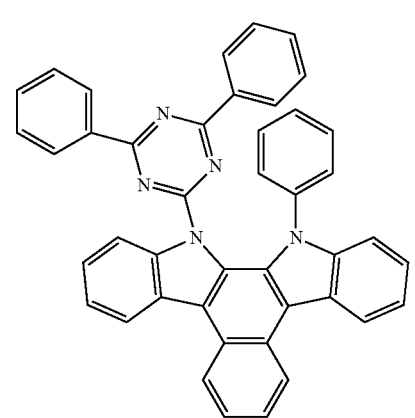
504
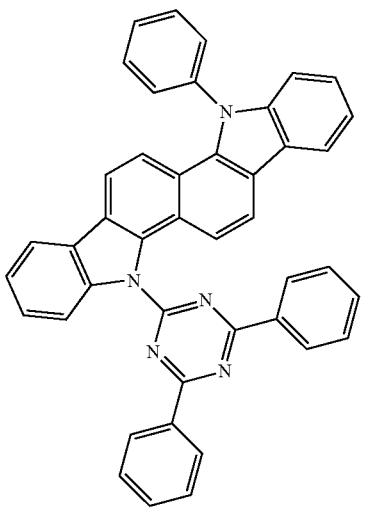
505
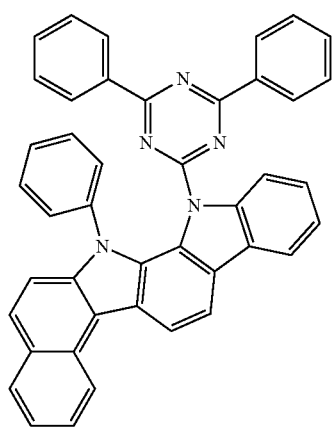
506
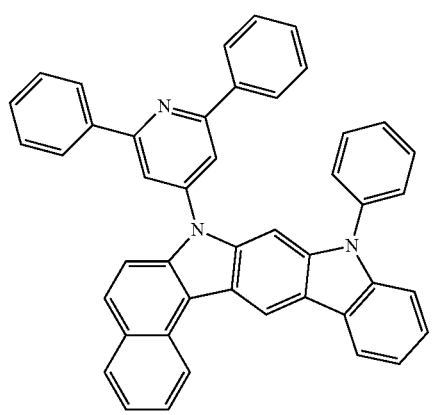

-continued

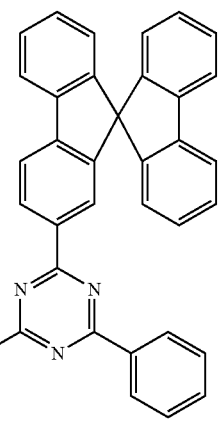
507

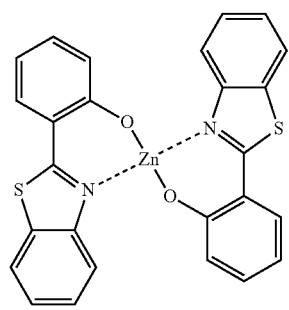
508

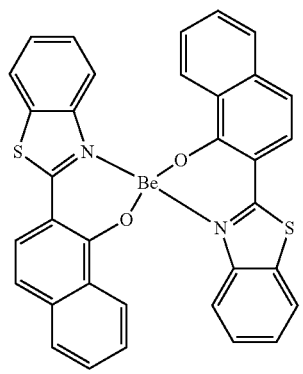
509

Also, the host may be an anthracene-based compound represented by Formula 400 below.

Formula 400

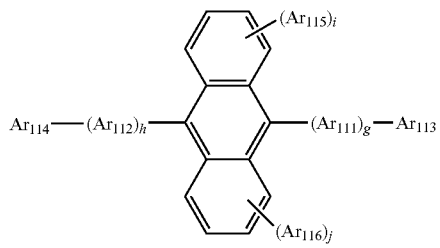

In Formula 400, $Ar_{111}$ and $Ar_{112}$ may each independently be a substituted or unsubstituted $C_5$-$C_{60}$ arylene group. $Ar_{113}$ to $Ar_{116}$ may each independently be a substituted or unsubstituted $C_1$-$C_{10}$ alkyl group, or a substituted or unsubstituted $C_5$-$C_{60}$ aryl group. Also, g, h, l, and j are each independently an integer of 0 to 4.

For example, $Ar_{111}$ and $Ar_{112}$ in Formula 400 may each independently be a phenylene group, a naphthalene group, a phenanthrenyl group, or a pyrenylene group; or a phenylene group, a naphthalene group, a phenanthrenyl group, a fluorenyl group, or a pyrenylene group substituted with at least one of a phenyl group, a naphthyl group, or an anthryl group. However, $Ar_{111}$ and $Ar_{112}$ are not limited thereto.

g, h, i, and j in Formula 400 may each independently be 0, 1, or 2.

$Ar_{113}$ to $Ar_{116}$ in Formula 400 may each independently be a $C_1$-$C_{10}$ alkyl group substituted with at least one of a phenyl group, a naphthyl group, or an anthryl group; a phenyl group; a naphthyl group; an anthryl group; a pyrenyl group; a phenanthrenyl group; a fluorenyl group; or a phenyl group, a naphthyl group, an anthryl group, a pyrenyl group, a phenanthrenyl group, or a fluorenyl group substituted with at least one of a deuterium atom, a halogen atom, a hydroxyl group, a cyano group, a nitro group, an amino group, an amidino group, a hydrazine group, a hydrazone group, a carboxyl group or salt thereof, a sulfonic acid group or salt thereof, a phosphoric acid group or salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a phenyl group, a naphthyl group, an anthryl group, pyrenyl group, a phenanthrenyl group, a fluorenyl group, or

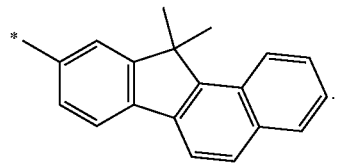 [SMILES: Cc1ccc2c(c1)C(C)(C)c1c-2ccc2ccccc12]

However, $Ar_{113}$ to $Ar_{116}$ are not limited thereto.

For example, the anthracene-based compound represented by Formula 400 may be one of the following compounds, but is not limited thereto.

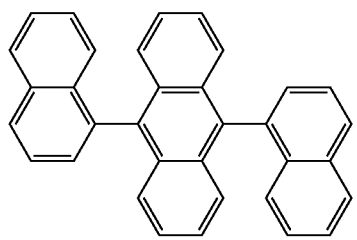

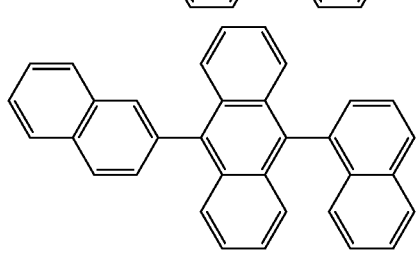

-continued
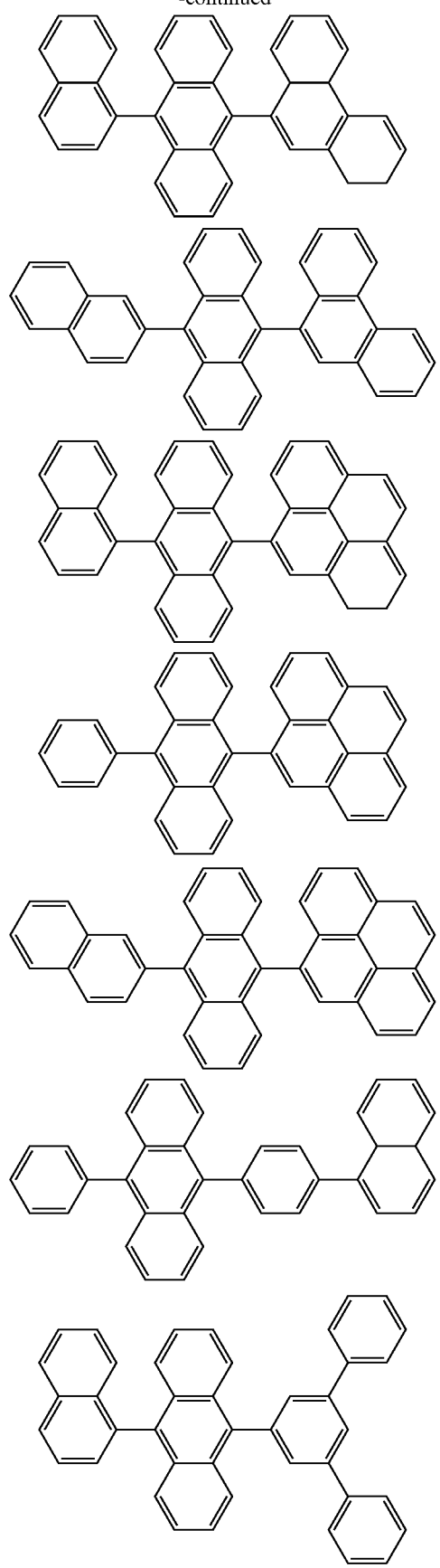
-continued
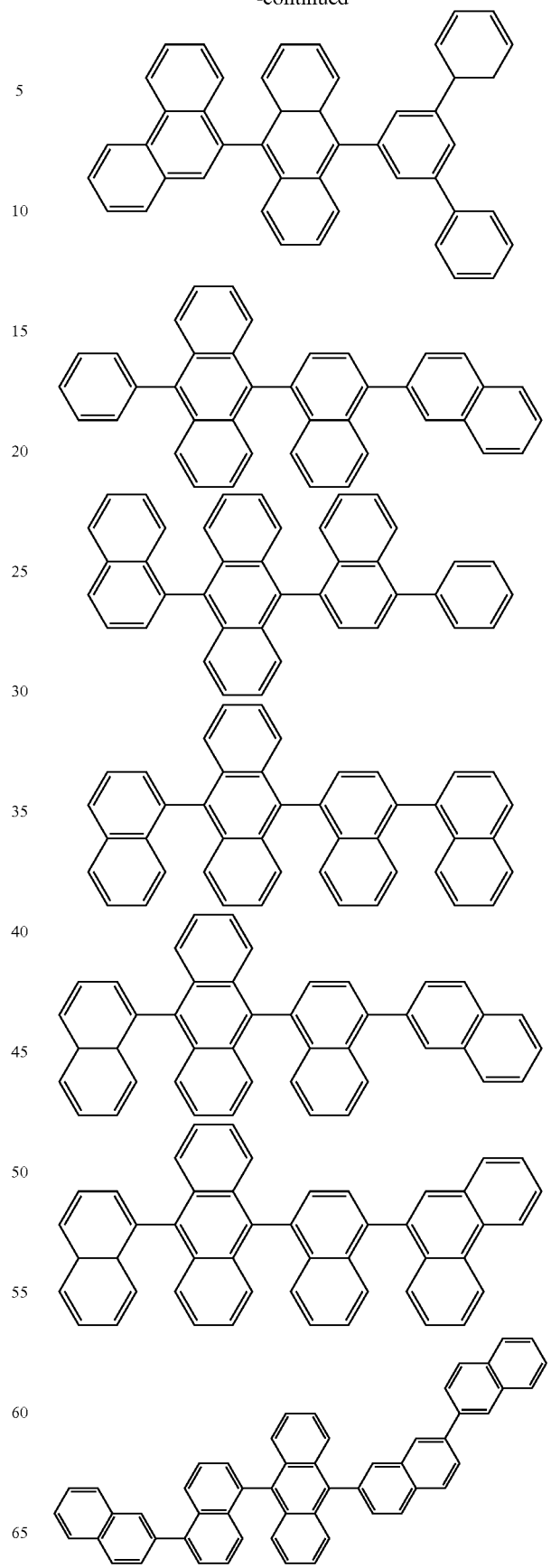

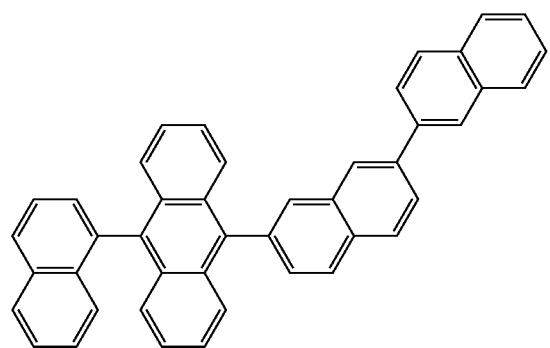

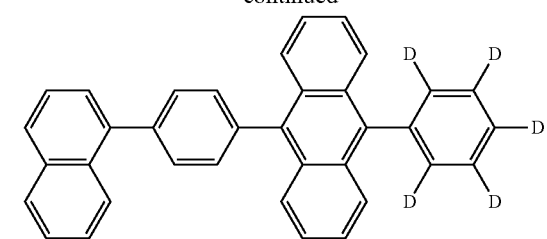
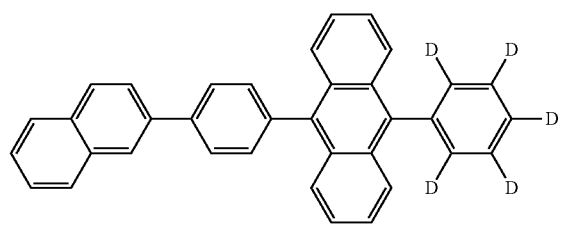
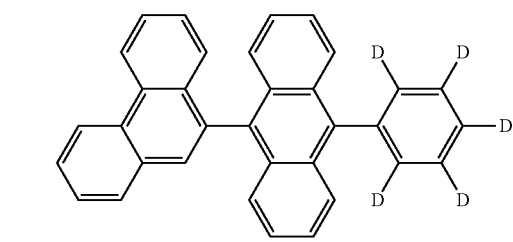
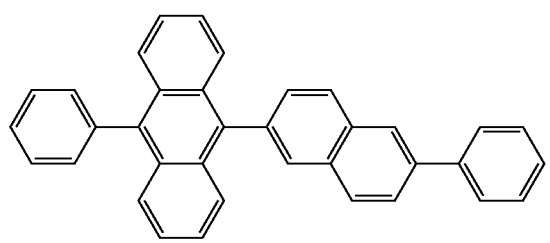
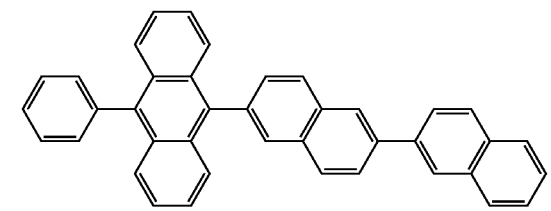
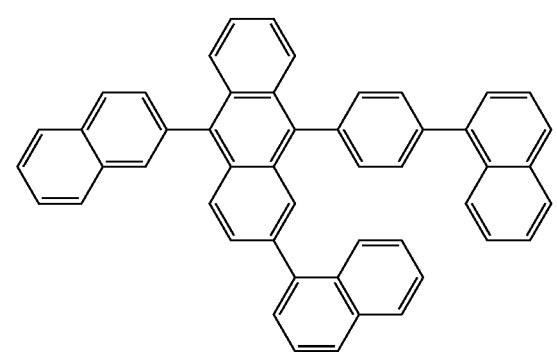
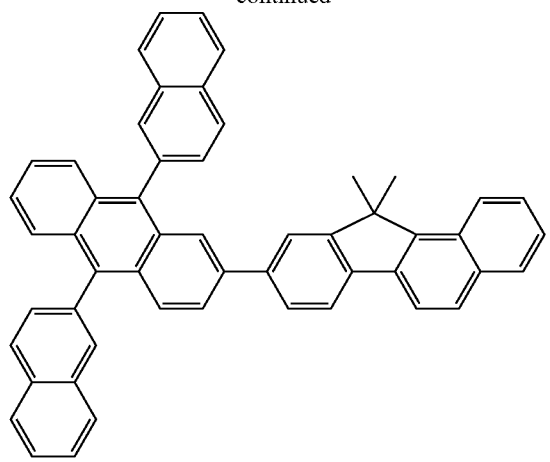
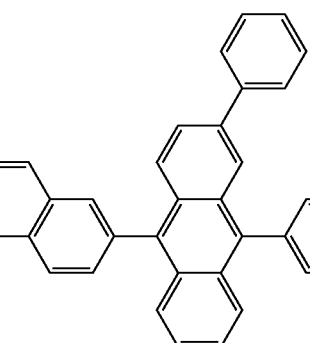
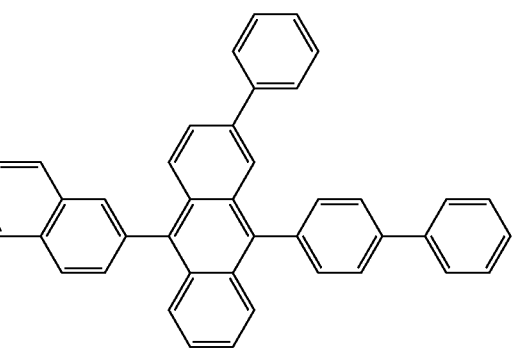
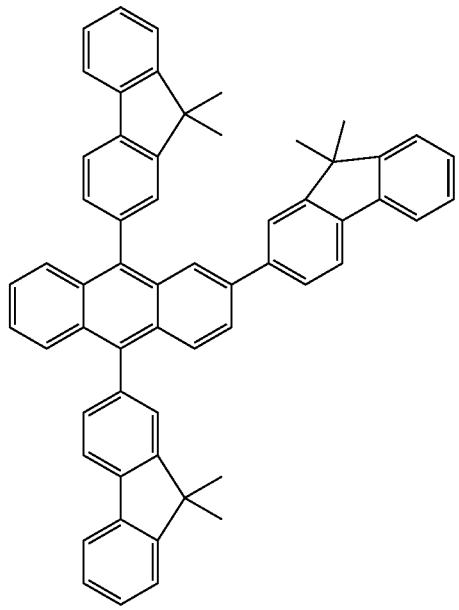

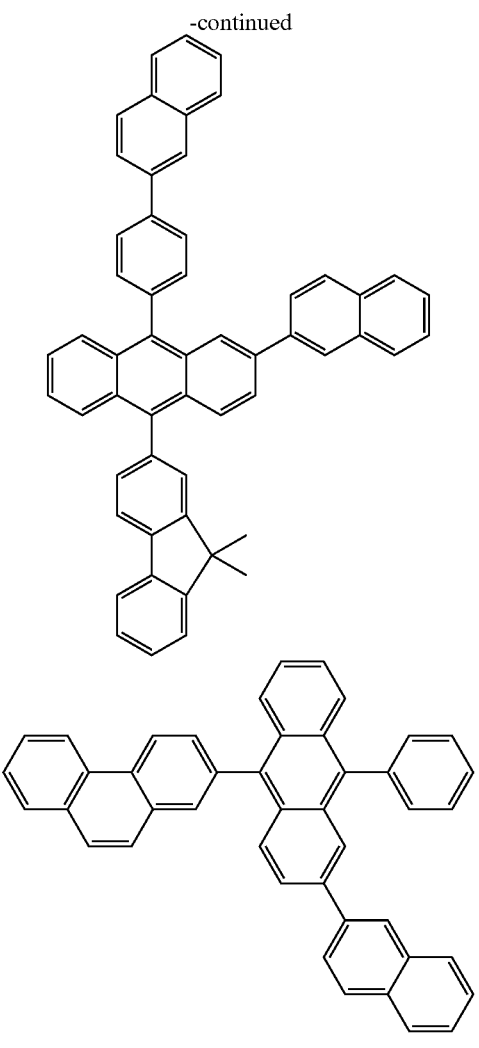

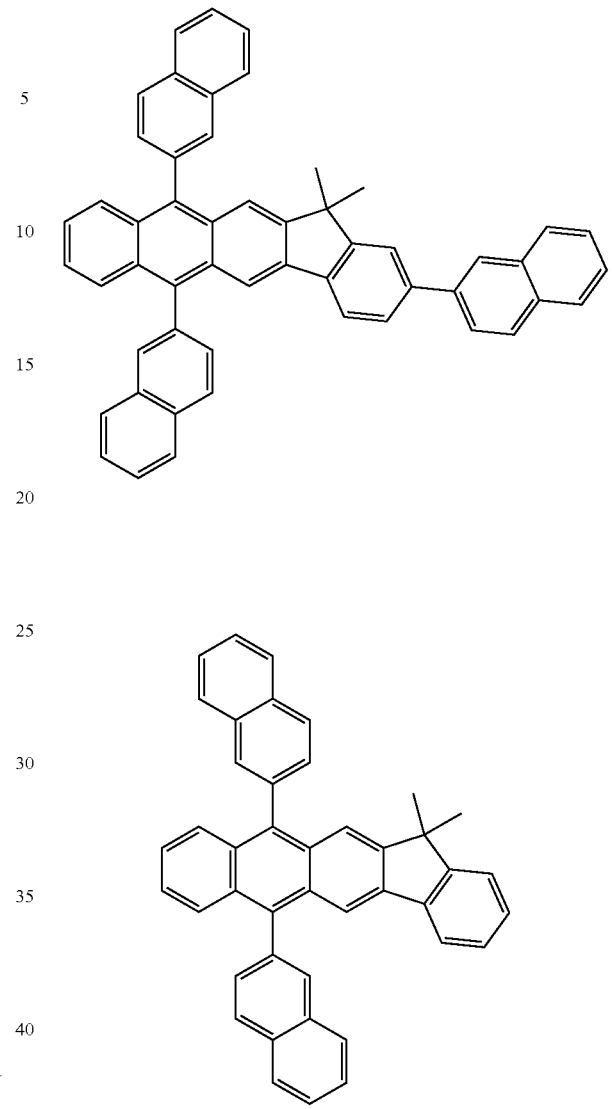

Also, the host may be an anthracene-based compound represented by Formula 401 below.

Formula 401

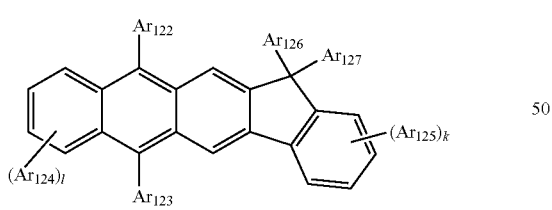

$Ar_{122}$ to $Ar_{125}$ in Formula 401 are the same as $Ar_{113}$ in Formula 400, and the description of $Ar_{113}$ in Formula 400 is fully incorporated here.

$Ar_{126}$ and $Ar_{127}$ in Formula 401 may each independently be a $C_1$-$C_{10}$ alkyl group (for example, a methyl group, an ethyl group, or a propyl group).

k and l in Formula 401 may each independently be an integer of 0 to 4. For example, k and l may be 0, 1, or 2.

For example, the anthracene-based compound represented by Formula 401 may be one of the following compounds, but is not limited thereto.

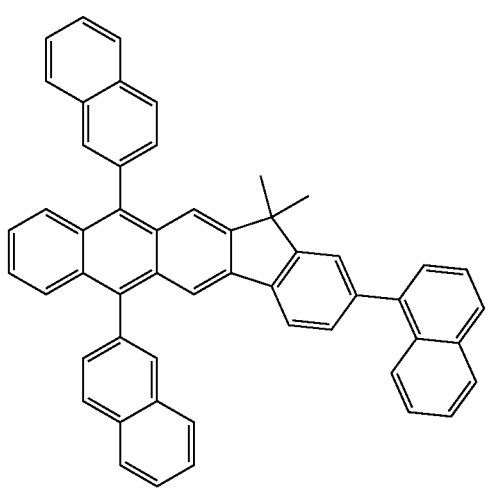

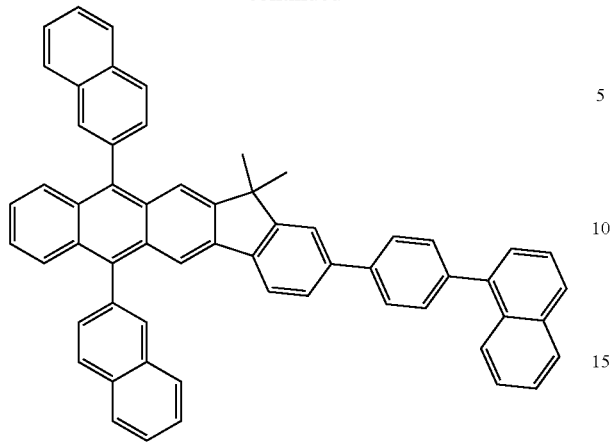
When the organic light-emitting device is a full color organic light-emitting device, the EML may be patterned into a red EML, a green EML, and a blue EML. The red EML, green EML, and blue EML may include the following dopants (ppy=phenylpyridine).
Non-limiting examples of suitable blue dopants include the following compounds.
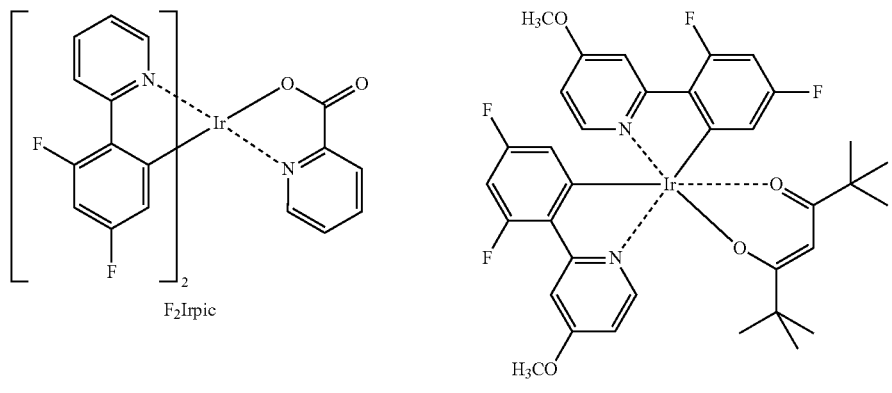
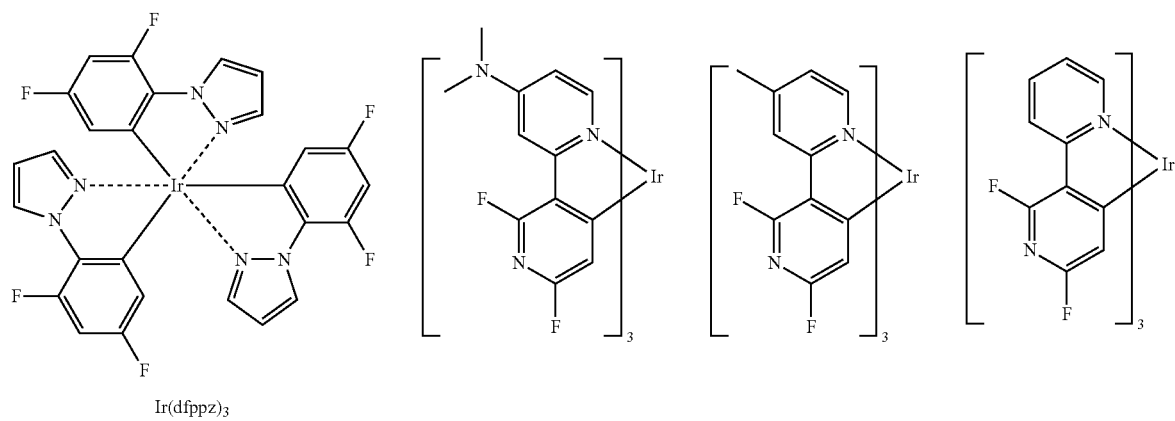

-continued
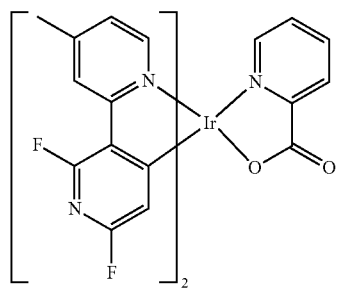
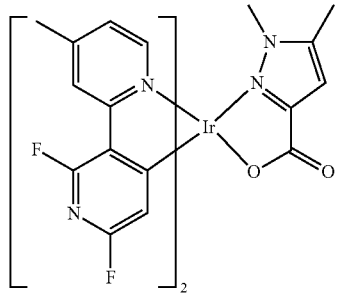
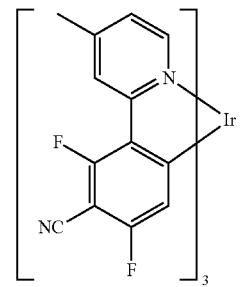
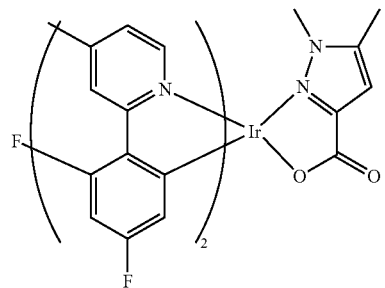
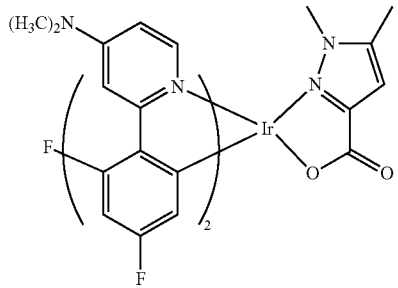
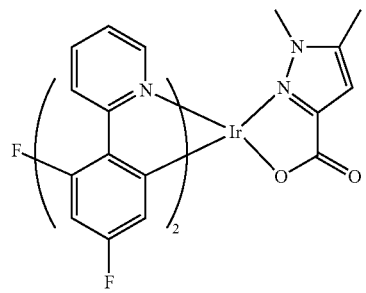
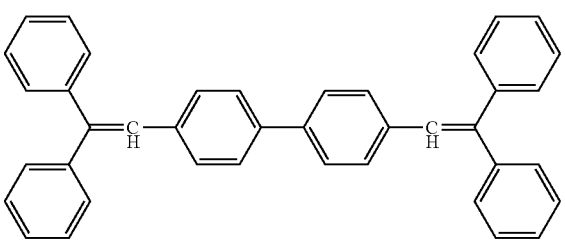
DPVBi
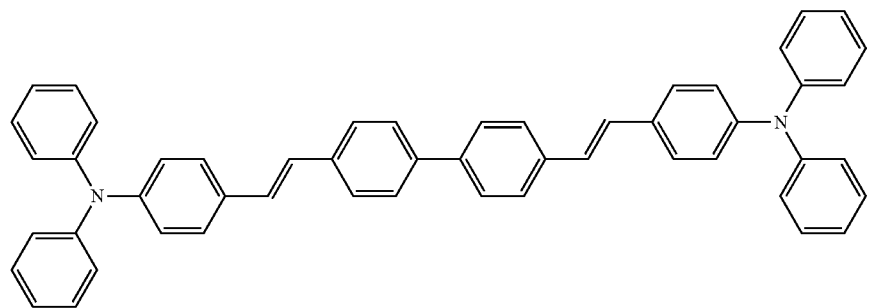
DPAVBi
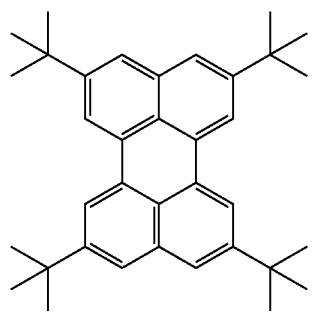
TBPe Non-limiting examples of suitable red dopants include the following compounds.
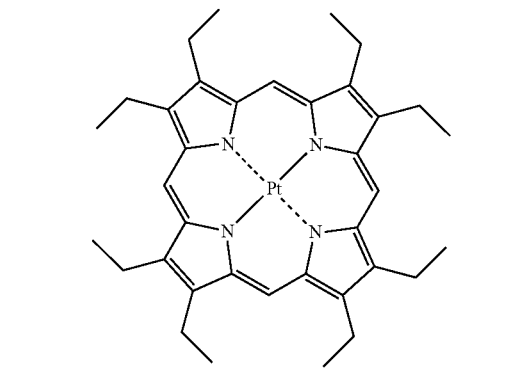
PtOEP
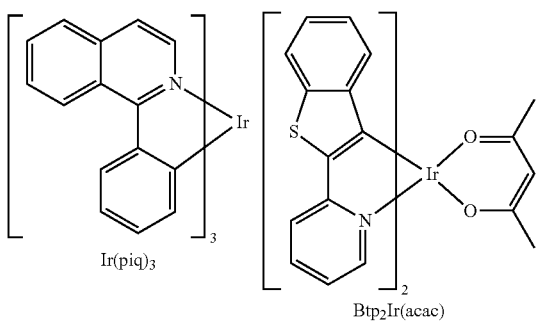
Ir(piq)₃         Btp₂Ir(acac)
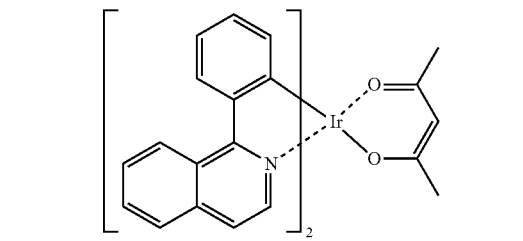
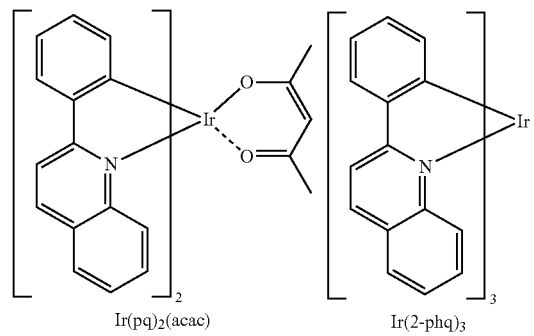
Ir(pq)₂(acac)         Ir(2-phq)₃
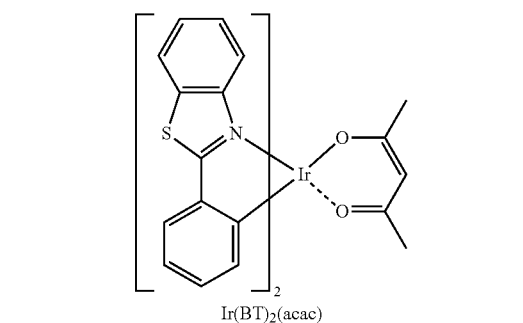
Ir(BT)₂(acac)
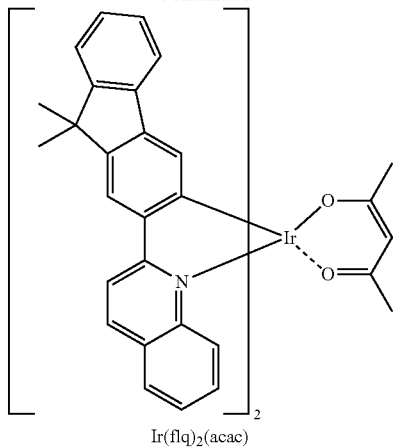
Ir(flq)₂(acac)
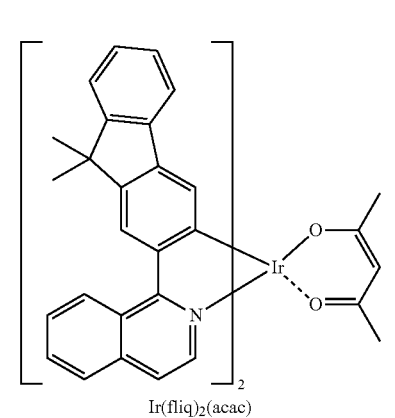
Ir(fliq)₂(acac)
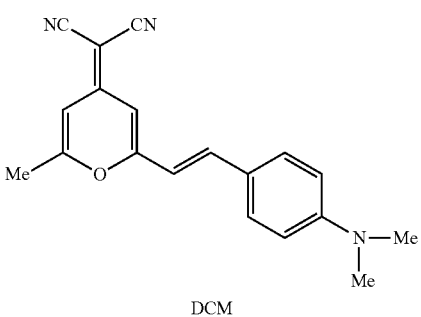
DCM
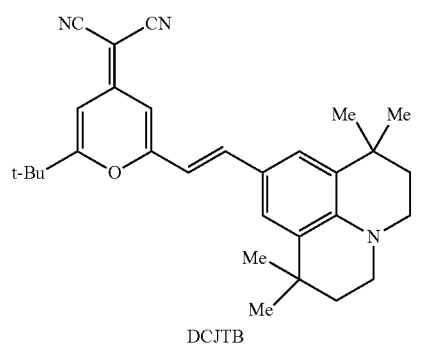
DCJTB
Non-limiting examples of suitable green dopants include the following compounds.

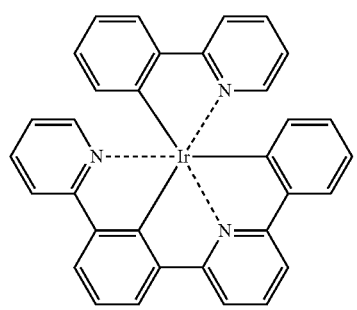
Ir(ppy)₃
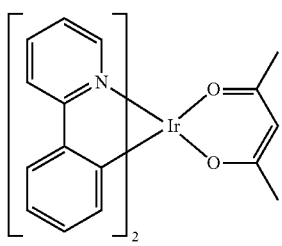
Ir(ppy)₂(acac)
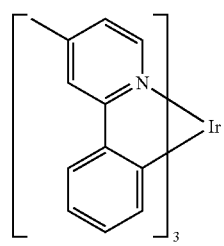
Ir(mpyp)₃
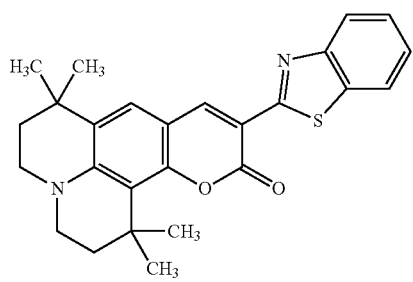
C545T
The dopant in the EML may also be a Pd-complex or a Pt-complex, but the dopant is not limited thereto. Non-limiting examples of suitable Pd-complexes and Pt-complexes include the following compounds.
D1
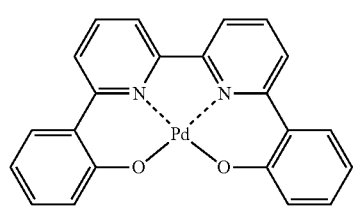
D2
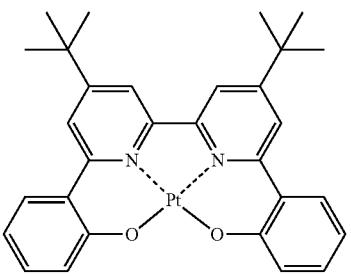
D3
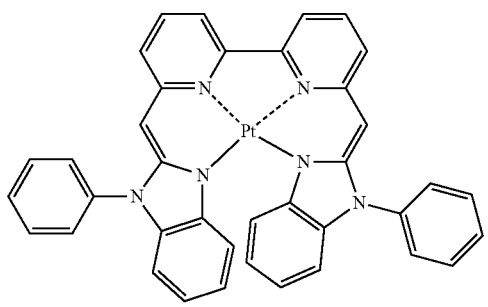
D4
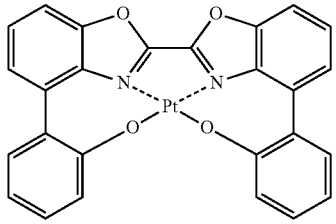
D5
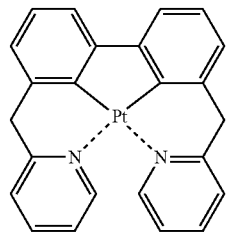
D6
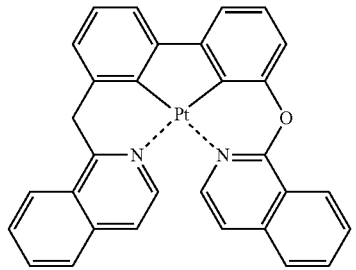
D7
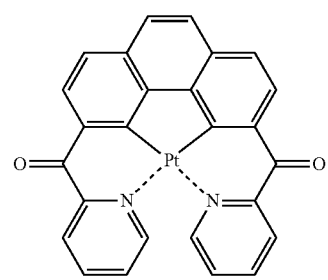

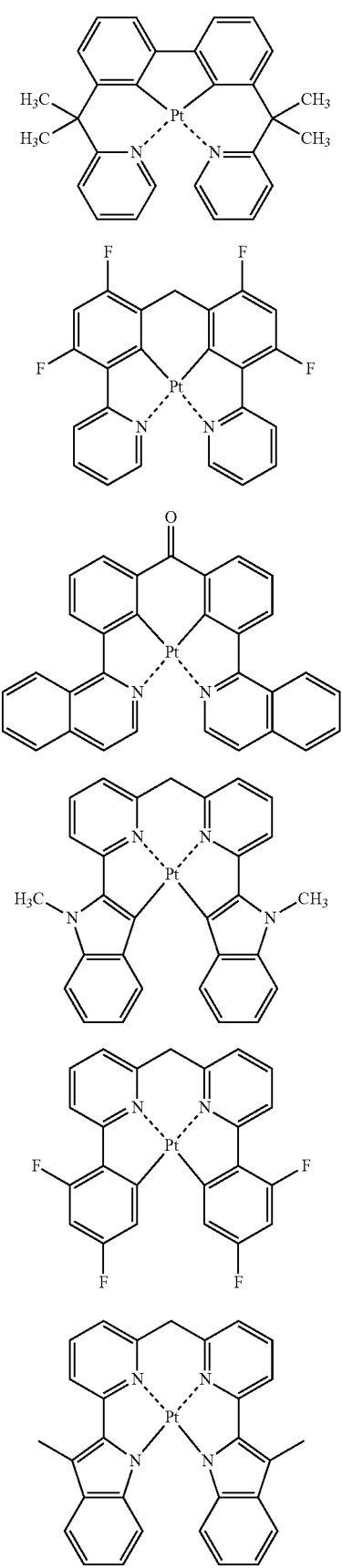
D8
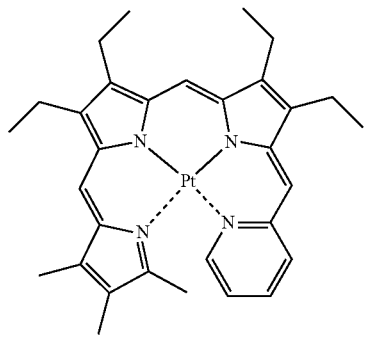
D9
D14
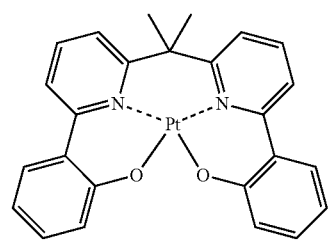
D10
D15
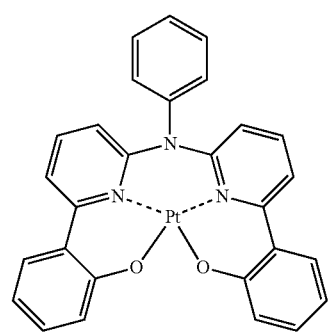
D11
D16
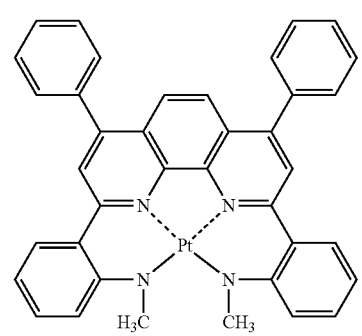
D12
D17
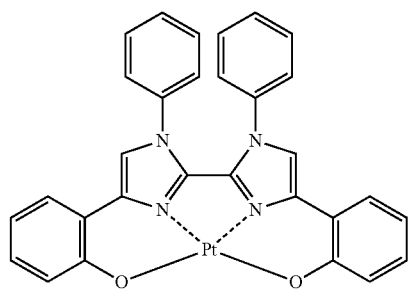
D13
D18

D19 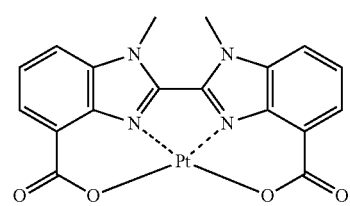
D20 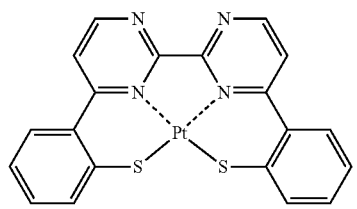
D21 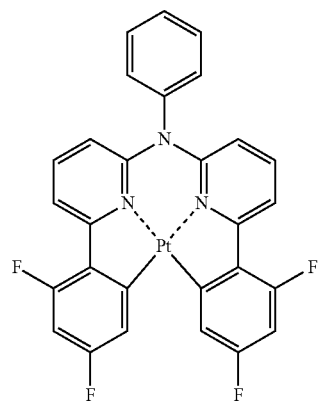
D22 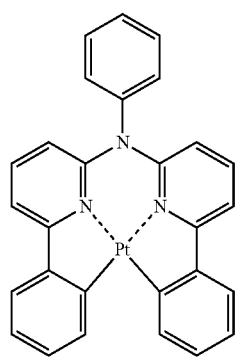
D23 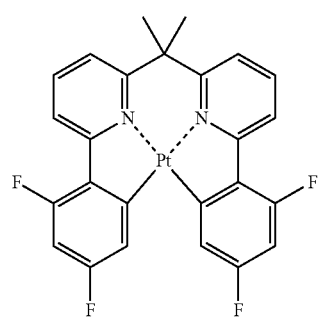
D24 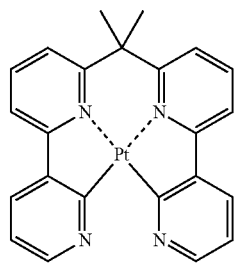
D25 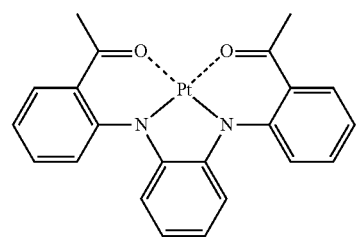
D26 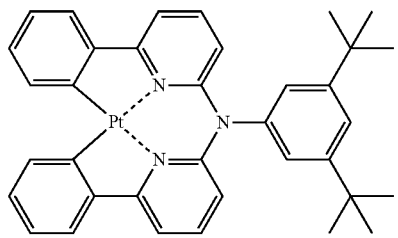
D27 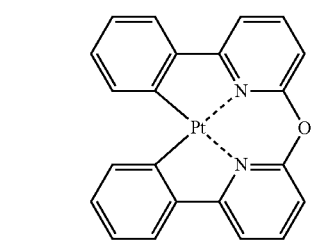
D28 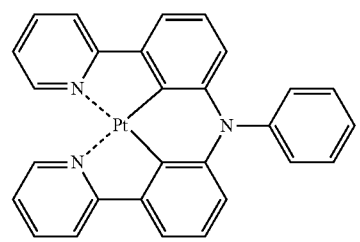
D29 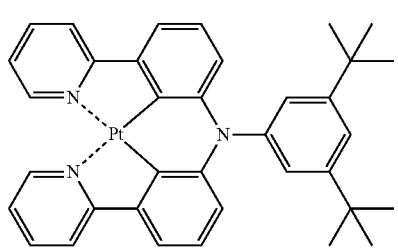

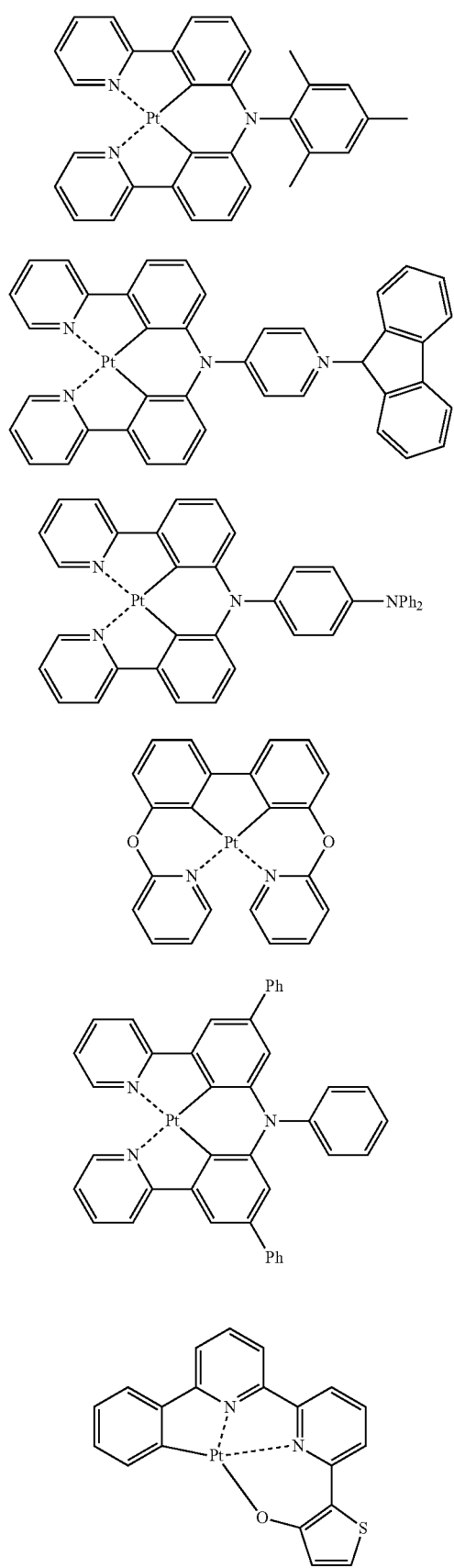
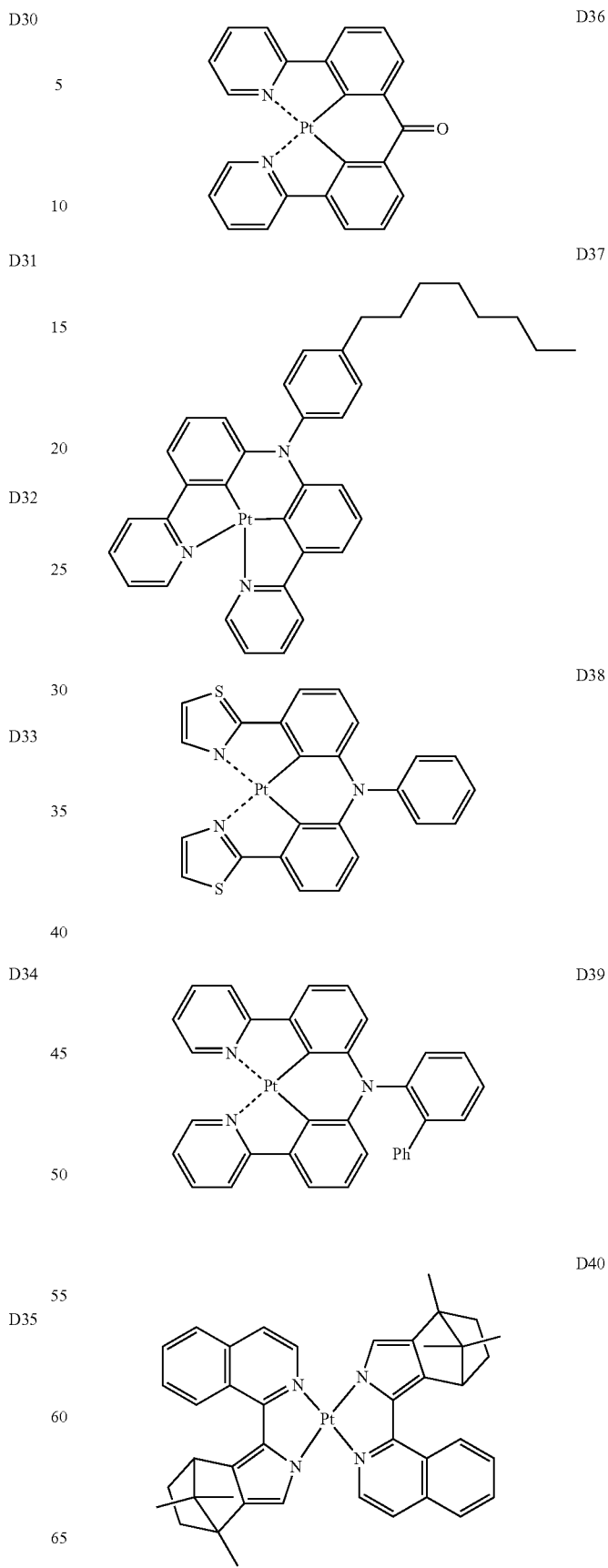

D41 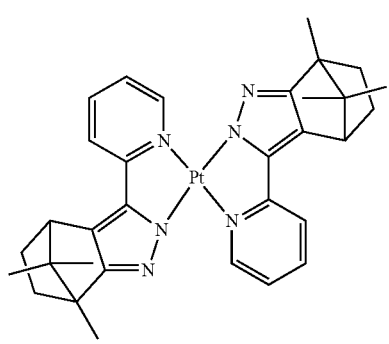
D42 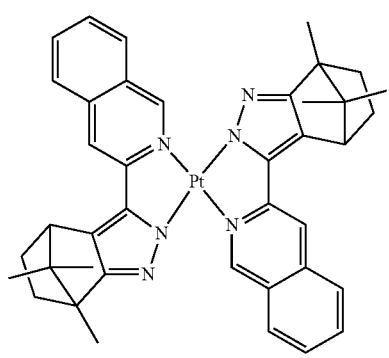
D43 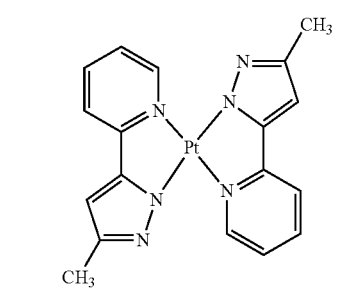
D44 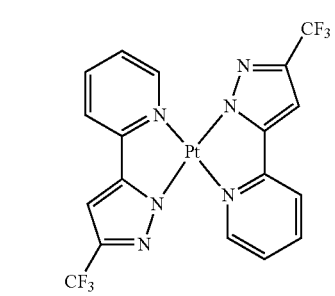
D45 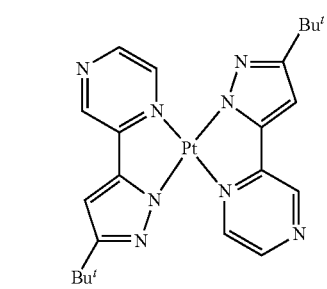
D46 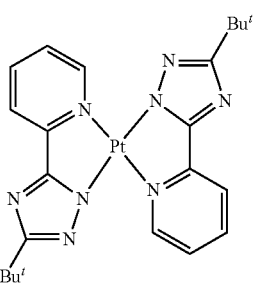
D47 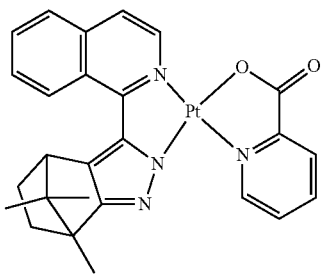
D48 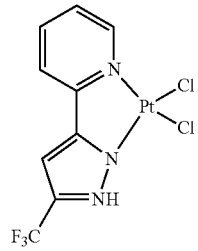
D49 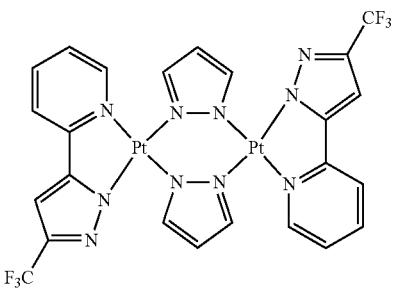
D50 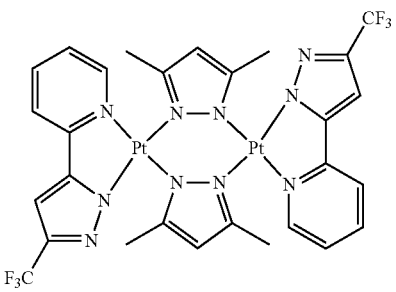
The dopant in the EML may also be an Os-complex, but the dopant is not limited thereto. Non-limiting examples of suitable Os-complexes include the following compounds.

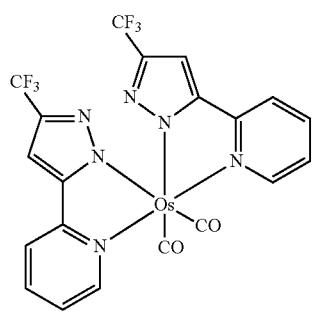

Os(fppz)₂(CO)₂

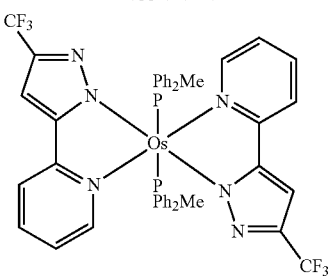

Os(fppz)₂(PPh₂Me)₂

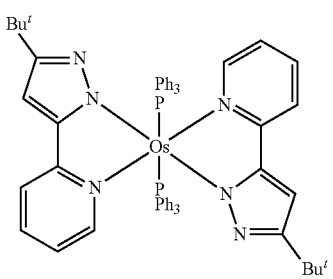

Os(bppz)₂(PPh₃)₂

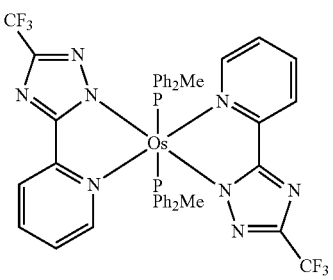

Os(fptz)₂(PPh₂Me)₂

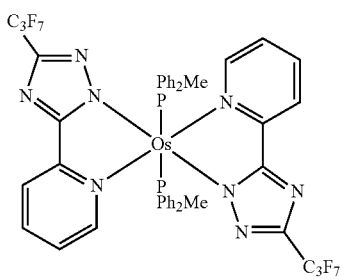

Os(hptz)₂(PPh₂Me₂)₂

When the EML includes a host and a dopant, the amount of the dopant may be about 0.01 to about 15 parts by weight based on about 100 parts by weight of the host. However, the amount of the dopant is not limited thereto.

The thickness of the EML may be about 100 Å to about 10,000 Å, for example, about 200 Å to about 600 Å. If the thickness of the EML is within either of these ranges, good luminescent characteristics may be obtained without a substantial increase in driving voltage.

Next, an electron transport layer (ETL) is formed on the EML by various methods, for example, by vacuum deposition, spin coating, casting, or the like. When the ETL is formed using vacuum deposition or spin coating, the deposition or coating conditions may be similar to those used to form the HIL, though the conditions for deposition or coating may vary according to the material that is used to form the ETL.

Any material capable of stably transporting electrons injected from an electron injection electrode (cathode) may be used as the material for the ETL. Non-limiting examples of suitable electron transportation materials include a quinoline derivative, such as tris(8-hydroxyquinolinato)aluminum (Alq3), TAZ, Balq, beryllium bis(benzoquinolin-10-olate) (Bebq₂), ADN, Compound 201, or Compound 202.

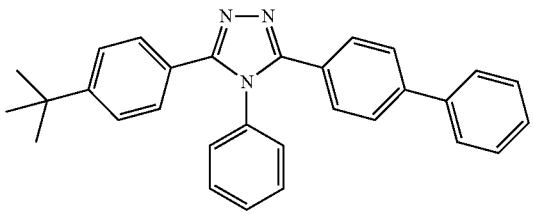

TAZ

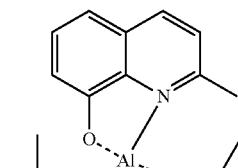
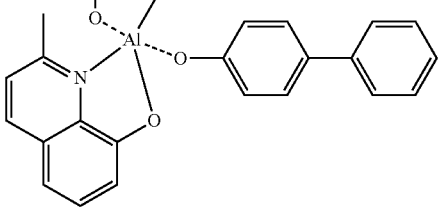

BAlq

Compound 201

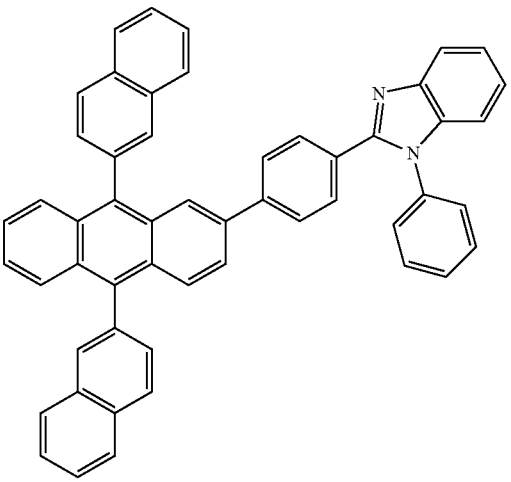

Compound 202

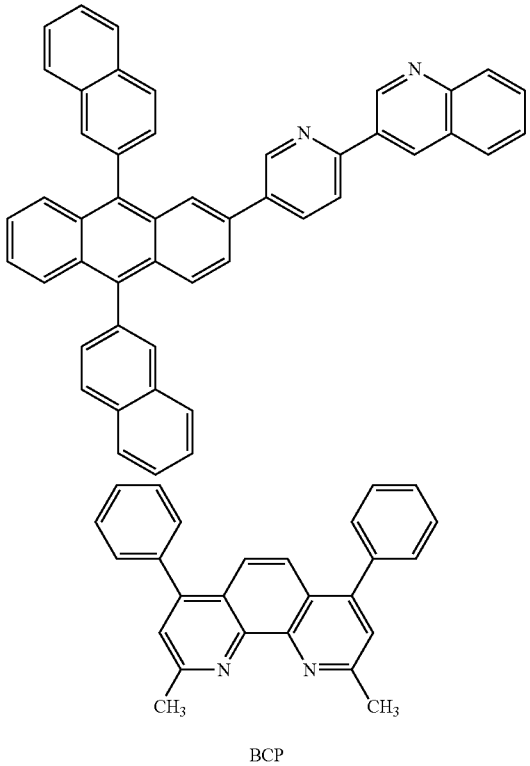

BCP

The thickness of the ETL may be about 100 Å to about 1,000 Å, for example, about 150 Å to about 500 Å. When the thickness of the ETL is within either of these ranges, the ETL may have satisfactory electron transportation characteristics without a substantial increase in driving voltage.

In addition to an electron transporting organic compound, the ETL may further include a metal-containing material. The metal-containing material may include a lithium (Li) complex. Non-limiting examples of the Li complex include lithium quinolate (LiQ) and Compound 203.

Compound 203

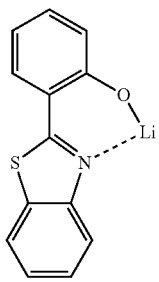

Then, an electron injection layer (EIL), which facilitates injection of electrons from the cathode, may be formed on the ETL. Any suitable electron-injecting material may be used to form the EIL. Non-limiting examples of suitable EIL materials include LiF, NaCl, CsF, $Li_2O$, and BaO. The deposition conditions of the EIL may be similar to those used to form the HIL, although the deposition conditions may vary according to the material that is used to form the EIL.

The thickness of the EIL may be about 1 Å to about 100 Å, for example, about 3 Å to about 90 Å. When the thickness of the EIL is within either of these ranges, the EIL may have satisfactory electron transportation characteristics without a substantial increase in a driving voltage.

The second electrode may be disposed on the organic layer. The second electrode may be a cathode, which is an electron injection electrode. The second electrode material may be a low work function material, such as a metal, an alloy, an electrically conductive compound, or a mixture thereof. For example, lithium (Li), magnesium (Mg), aluminum (Al), aluminum-lithium (Al—Li), calcium (Ca), magnesium-indium (Mg—In), magnesium-silver (Mg—Ag), etc. may be used to form a thin film transmissive electrode. In some embodiments, a top-emission light-emitting device may be made using indium tin oxide (ITO) or indium zinc oxide (IZO) to form a transmissive electrode.

Although the organic light-emitting device has been described with reference to the FIGURE, the OLED is not limited thereto.

Also, when the EML includes a phosphorescent dopant, to prevent diffusion of triplet excitons or holes into the ETL a hole blocking layer (HBL) may be formed between the ETL and the EML or between the E-functional layer and the EML by vacuum deposition, spin coating, casting, LB deposition, etc. When the HBL is formed by vacuum deposition or spin coating, the deposition or coating conditions may be similar to those used to form the HIL, although the deposition or coating conditions may vary according to the material that is used to form the HBL. The hole blocking material may be any suitable hole blocking material, non-limiting examples of which include an oxadiazole derivative, a triazole derivative, a phenanthroline derivative, etc. For example, BCP (illustrated below) may be used as the hole blocking material.

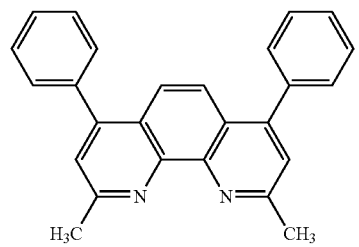

BCP

The thickness of the HBL may be about 20 Å to about 1,000 Å, for example, about 30 Å to about 300 Å. If the thickness of the HBL is within either of these ranges, good hole blocking properties may be obtained without a substantial increase in driving voltage.

An organic light-emitting device according to an embodiment of the present invention may be used in various flat panel display apparatuses, such as passive matrix organic light-emitting display apparatuses or active matrix organic light-emitting display apparatuses. In particular, when the organic light-emitting device is included in an active matrix organic light-emitting display apparatus, the first electrode (disposed on the substrate) functions as a pixel and may be electrically connected to a source electrode or a drain electrode of a thin film transistor. In addition, the organic light-emitting device may be included in a flat panel display apparatus that emits light in opposing directions.

The organic layer of an organic light-emitting device according to an embodiment of the present invention may be formed by depositing a compound according to an embodiment of the present invention, or by coating a solution including the compound according to an embodiment of the present invention. The latter method is referred to as a wet method.

Hereinafter, one or more embodiments of the present invention will be described with reference to the following examples. These examples are presented for illustrative purposes only, and do not limit the purpose and scope of the one or more embodiments of the present invention.

EXAMPLES

Synthesis Example 1

Synthesis of Compound 1

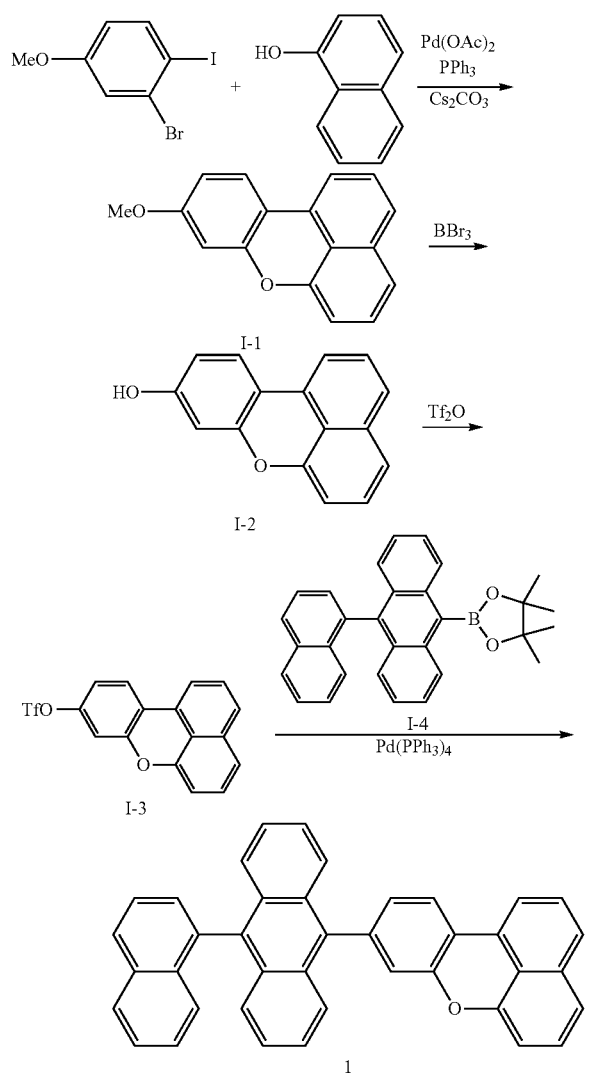

Synthesis of Intermediate I-1

3.13 g (10 mmol) of 2-bromo-1-iodo-4-methoxybenzene, 1.58 g (11 mmol) of 1-naphthol, 0.112 g (0.5 mmol) of palladium acetate, 0.651 g (2.0 mmol) of triphenylphosphine, and 13 g (40 mmol) of cesium carbonate were dissolved in 60 mL of dimethylformamide (DMF), and then, the mixture was stirred at a temperature of 140° C. for 24 hours. The reaction solution was cooled to room temperature, and then, 60 mL of water was added thereto, and an extraction process was performed three times using 60 mL of ethylether. The collected organic layer was dried using magnesium sulfate, and the residue obtained by evaporating the solvent was separation-purified by silica gel column chromatography to obtain 1.64 g (yield 66%) of Intermediate I-1. The obtained compound was identified by MS/FAB. $C_{17}H_{12}O_2$: calc. 248.08. found 248.10.

Synthesis of Intermediate I-2

1.64 g (6.6 mmol) of Intermediate I-1 was dissolved in 60 mL of methylene chloride (MC), and then, 0.93 mL (9.9 mmol) of $BBr_3$ was slowly added dropwise thereto at a temperature of −78° C. The reaction solution was heated to room temperature and then stirred for 24 hours at room temperature. When the reaction was completed, 15 mL of MeOH and 30 mL of $H_2O$ were added thereto, and an extraction process was performed three times using 30 mL of MC. The collected organic layer was dried using magnesium sulfate, and then the residue obtained by evaporating the solvent was separation-purified by silica gel column chromatography to obtain 1.41 g (yield 91%) of Intermediate I-2. The obtained compound was identified by MS/FAB. $C_{16}H_{10}O_2$: calc. 234.07. found 234.11.

Synthesis of Intermediate I-3

1.41 g (6.0 mmol) of Intermediate I-2 was dissolved in 20 mL of toluene and 20 mL of 30% potassium phosphate, and then, at a temperature of 0° C., 2.03 g (7.2 mmol) of trifluoromethanesulfonic acid anhydride was slowly added dropwise thereto. The reaction solution was heated to room temperature, and then stirred for 3 hours. Then, 30 mL of water was added thereto, and an extraction process was performed three times using 30 mL of ethylether. The collected organic layer was dried using magnesium sulfate and the residue obtained by evaporating the solvent was separation-purified by silica gel column chromatography to obtain 1.63 g (yield 81%) of Intermediate I-1. The obtained compound was identified by MS/FAB. $C_{17}H_9F_3O_4S$: calc. 336.02. found 336.0.

Synthesis of Compound 1

1.63 g (4.4 mmol) of Intermediate I-3, 1.89 g (4.4 mmol) of Intermediate I-4, 0.25 g (0.22 mmol) of tetrakis(triphenylphosphine)palladium ($Pd(PPh_3)_4$), and 1.40 g (6.6 mmol) of potassium phosphate were dissolved in 50 mL of THF solution, and then, at a temperature of 70° C., the mixture was stirred for 6 hours. The reaction solution was cooled to room temperature, and then, 40 mL of water was added thereto. Then, an extraction process was performed three times using 40 mL of ethylether. The collected organic layer was dried using magnesium sulfate and the residue obtained by evaporating the solvent was separation-purified by silica gel column chromatography to obtain 1.95 g (yield 85%) of Compound 1. The obtained compound was identified by MS/FAB. $C_{40}H_{24}O$: calc. 520.18. found 520.21.

Synthesis Example 2

Synthesis of Compound 5

1.88 g (yield 82%) of Compound 5 was obtained as in the synthesis of Compound 1, except that 2-bromoiodobenzene was used instead of 2-bromo-1-iodo-4-methoxybenzene, and 4-methoxy-1-naphthol was used instead of 1-naphthol. The obtained compound was identified by MS/FAB. $C_{40}H_{24}O$: calc. 520.18. found 520.20.

Synthesis Example 3

Synthesis of Compound 12

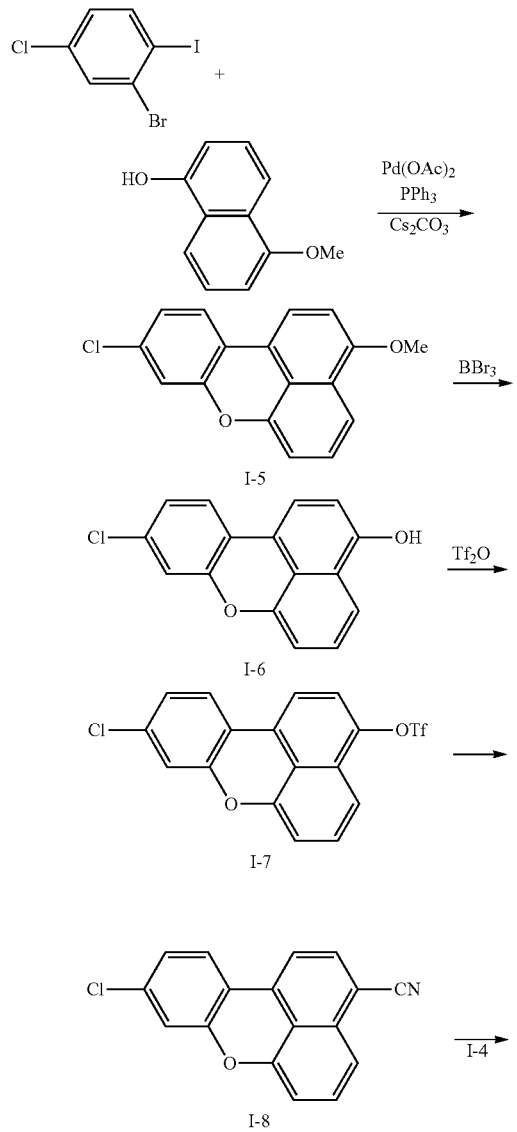

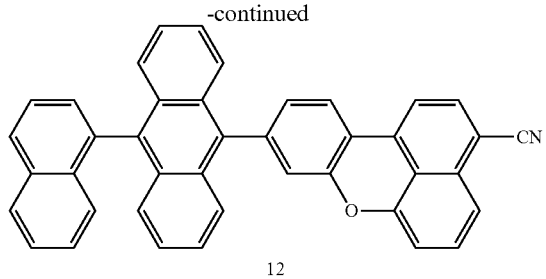

Synthesis of Intermediate I-5

3.17 g (10 mmol) of 2-bromo-4-chloro-1-iodobenzene, 1.92 g (11 mmol) of 5-methoxy-1-naphthol, 0.112 g (0.5 mmol) of palladium acetate, 0.651 g (2.0 mmol) of triphenylphosphine, and 13 g (40 mmol) of cesium carbonate were dissolved in 60 mL of DMF, and then the mixture was stirred at a temperature of 140° C. for 24 hours. The reaction solution was cooled to room temperature, and then 60 mL of water was added thereto. Then, an extraction process was performed three times using 60 mL of ethylether. The collected organic layer was dried using magnesium sulfate and the residue obtained by evaporating the solvent was separation-purified by silica gel column chromatography to obtain 1.64 g (yield 58%) of Intermediate I-5. The obtained compound was identified by MS/FAB. $C_{17}H_{11}ClO_2$: calc. 282.04. found 282.01.

Synthesis of Intermediate I-6

1.64 g (5.8 mmol) of Intermediate I-5 was dissolved in 60 mL of MC, and then, at a temperature of −78° C., 0.82 mL (8.7 mmol) of $BBr_3$ was slowly added dropwise thereto. The reaction solution was heated to room temperature and then stirred for 24 hours at room temperature. When the reaction was completed, 15 mL of MeOH and 30 mL of $H_2O$ were added thereto, and then an extraction process was performed three times using 30 mL of MC. The collected organic layer was dried using magnesium sulfate, and then the residue obtained by evaporating the solvent was separation-purified by silica gel column chromatography to obtain 1.43 g (yield 92%) of Intermediate I-6. The obtained compound was identified by MS/FAB. $C_{16}H_9ClO_2$: calc. 268.03. found 268.01.

Synthesis of Intermediate I-7

1.43 g (5.3 mmol) of Intermediate I-6 was dissolved in 20 mL of toluene and 20 mL of 30% potassium phosphate, and then, at a temperature of 0° C., 1.79 g (6.4 mmol) of trifluoromethanesulfonic acid anhydride was slowly added dropwise thereto. The reaction solution was heated to room temperature, and then stirred for 3 hours. Then, 30 mL of water was added thereto, and an extraction process was performed three times using 30 mL of ethylether. The collected organic layer was dried using magnesium sulfate and the residue obtained by evaporating the solvent was separation-purified by silica gel column chromatography to obtain 1.70 g (yield 80%) of Intermediate I-7. The obtained compound was identified by MS/FAB. $C_{17}H_8ClF_3O_4S$: calc. 399.98. found 400.01.

Synthesis of Intermediate I-8

1.70 g (4.2 mmol) of Intermediate I-7, 4.7 mg (0.021 mmol) of palladium acetate, 0.39 g (0.92 mmol) of $K_4$[Fe (CN)₆].3H₂O, and 0.58 g (4.2 mmol) of potassium carbonate were dissolved in 20 mL of H₂O/1,4-dioxane (1:1). Then, at a temperature of 140° C., the mixture was stirred for 10 hours. The reaction solution was cooled to room temperature, and then extracted three times with 30 mL of water and 30 mL of diethylether. The collected organic layer was dried using magnesium sulfate, and then the residue obtained by evaporating the solvent was separation-purified by silica gel column chromatography to obtain 0.96 g (yield 82%) of Intermediate I-8. The obtained compound was identified by MS/FAB. C₁₇H₈ClNO: calc. 277.03. found 277.01.

Synthesis of Compound 12

0.96 g (3.4 mmol) of Intermediate I-8, 1.46 g (3.4 mmol) of Intermediate I-4, 0.046 g (0.05 mmol) of Pd₂(dba)₃, 0.02 g (0.1 mmol) of PtBu₃, and 1.66 g (5.1 mmol) of cesium carbonate were dissolved in 30 mL of a 1,4-dioxane solution. Then, at a temperature of 90° C., the mixture was stirred for 20 hours. The reaction solution was cooled to room temperature, and then 40 mL of water was added thereto. Then, an extraction process was performed three times using 40 mL of ethylether. The collected organic layer was dried using magnesium sulfate and the residue obtained by evaporating the solvent was separation-purified by silica gel column chromatography to obtain 1.54 g (yield 83%) of Compound 12. The obtained compound was identified by MS/FAB. C₄₁H₂₃NO: calc. 545.18. found 545.20.

Synthesis Example 4

Synthesis of Compound 15

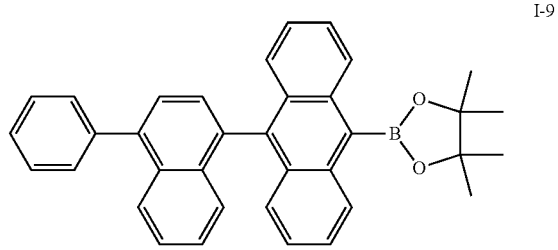 [SMILES: CC1(C)OB(c2c3ccccc3c(-c3ccc(-c4ccccc4)c4ccccc34)c3ccccc23)OC1(C)C]

2.28 g (yield 82%) of Compound 15 was obtained as in the synthesis of Compound 1, except that 1-bromo-2-iodo-4-methoxybenzene was used instead of 2-bromo-1-iodo-4-methoxybenzene, and Intermediate I-9 was used instead of Intermediate I-4. The obtained compound was identified by MS/FAB. C₄₆H₂₈O: calc. 596.21. found 596.18.

Synthesis Example 5

Synthesis of Compound 59

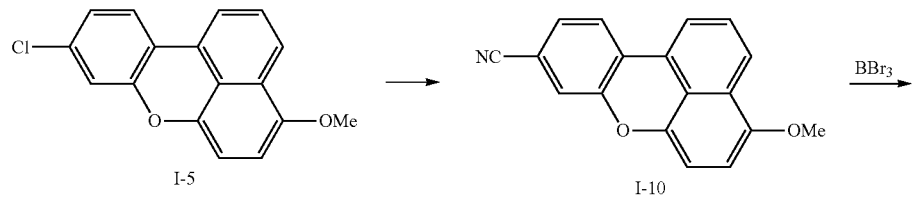

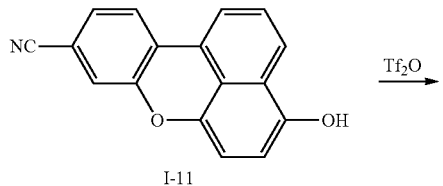

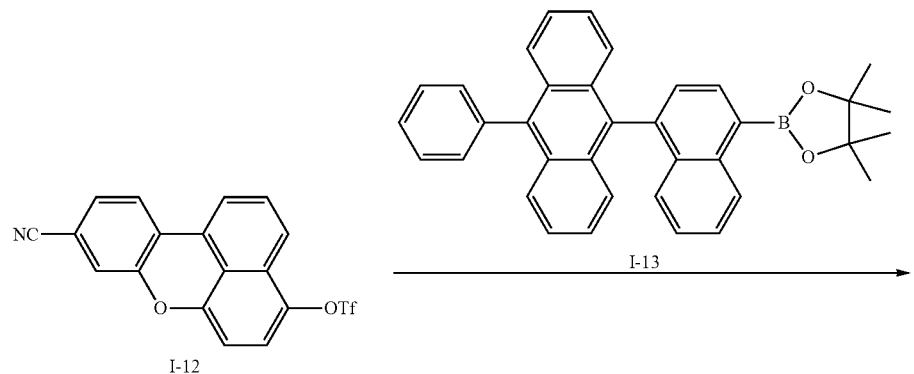

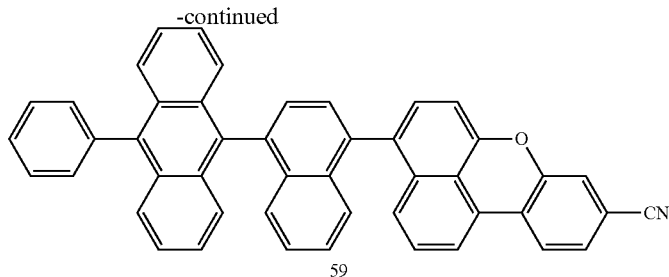

59

Synthesis of Intermediate I-10

1.70 g (4.2 mmol) of Intermediate I-5, 19 mg (0.084 mmol) of palladium acetate, 60 mg (0.13 mmol) of Xphos, 0.44 g (1.05 mmol) of $K_4[Fe(CN)_6] \cdot 3H_2O$, and 0.58 g (4.2 mmol) of potassium carbonate were dissolved in 20 mL of $H_2O/1,4$-dioxane (1:1). Then, at a temperature of 120° C., the mixture was stirred for 10 hours. The reaction solution was cooled to room temperature, and then extracted three times with 30 mL of water and 30 mL of diethylether. The collected organic layer was dried using magnesium sulfate, and then the residue obtained by evaporating the solvent was separation-purified by silica gel column chromatography to obtain 0.99 g (yield 86%) of Intermediate I-10. The obtained compound was identified by MS/FAB. $C_{18}H_{11}NO_2$: calc. 273.08. found 273.11.

Synthesis of Intermediate I-11

0.99 g (3.6 mmol) of Intermediate I-10 was dissolved in 20 mL of MC, and then, at a temperature of −78° C., 0.51 mL (5.4 mmol) of $BBr_3$ was slowly added dropwise thereto. The reaction solution was heated to room temperature and then stirred for 24 hours at room temperature. When the reaction was completed, 10 mL of MeOH and 20 mL of $H_2O$ were added thereto, and then an extraction process was performed three times using 20 mL of MC. The collected organic layer was dried using magnesium sulfate, and then the residue obtained by evaporating the solvent was separation-purified by silica gel column chromatography to obtain 0.87 g (yield 93%) of Intermediate I-11. The obtained compound was identified by MS/FAB. $C_{17}H_9NO_2$: calc. 259.06. found 259.10.

Synthesis of Intermediate I-12

0.87 g (3.3 mmol) of Intermediate I-6 was dissolved in 10 mL of toluene and 10 mL of 30% potassium phosphate, and then, at a temperature of 0° C., 1.09 g (3.9 mmol) of trifluoromethanesulfonic acid anhydride was slowly added dropwise thereto. The reaction solution was heated to room temperature, and then stirred for 3 hours. Then, 20 mL of water was added thereto, and an extraction process was performed three times using 20 mL of ethylether. The collected organic layer was dried using magnesium sulfate and the residue obtained by evaporating the solvent was separation-purified by silica gel column chromatography to obtain 1.06 g (yield 82%) of Intermediate I-12. The obtained compound was identified by MS/FAB. $C_{18}H_8F_3NO_4S$: calc. 391.01. found 391.05.

Synthesis of Compound 59

1.06 g (2.7 mmol) of Intermediate I-12, 1.37 g (2.7 mmol) of Intermediate I-13, 0.16 g (0.14 mmol) of tetrakis(triphenylphosphine)palladium $(Pd(PPh_3)_4)$, and 0.87 g (4.1 mmol) of potassium phosphate were dissolved in 40 mL of a THF solution. Then, at a temperature of 70° C., the mixture was stirred for 6 hours. The reaction solution was cooled to room temperature, and then 30 mL of water was added thereto. Then, an extraction process was performed three times using 30 mL of ethylether. The collected organic layer was dried using magnesium sulfate and the residue obtained by evaporating the solvent was separation-purified by silica gel column chromatography to obtain 1.04 g (yield 82%) of Compound 59. The obtained compound was identified by MS/FAB. $C_{40}H_{24}O$: calc. 621.21. found 621.24.

Additional compounds were synthesized using analogous synthesis methods to those described above, and appropriate intermediate materials. $^1H$ NMR and MS/FAB results of the synthetic compounds are shown in Table 1 below.

Also, methods for synthesizing compounds other than the compounds shown in Table 1 would be determinable by those of ordinary skill in the art by reference to the synthesis paths and source materials described above.

TABLE 1

| Compound | $^1H$ NMR (CDCl$_3$, 400 MHz) | MS/FAB found | calc. |
|---|---|---|---|
| 1 | δ = 8.02-8.00 (dd, 1H), 7.94 (d, 2H), 7.84-7.82 (m, 2H), 7.80 (d, 1H), 7.78 (d, 1H), 7.76 (d, 1H), 7.73-7.69 (m, 2H), 7.60-7.57 (m, 3H), 7.55-7.51 (m, 2H), 7.47-7.44 (m, 1H), 7.38-7.29 (m, 6H), 7.08-7.04 (m, 1H), 7.02-7.00 (dd, 1H) | 520.21 | 520.18 |
| 5 | δ = 8.12-8.10 (dd, 1H), 8.03-8.01 (dd, 1H), 7.85-7.80 (m, 5H), 7.73-7.69 (m, 2H), 7.64-7.62 (m, 1H), 7.54-7.52 (dd, 1H), 7.46-7.44 (m, 1H), 7.40-7.38 (m, 1H), 7.35-7.30 (m, 6H), 7.25-7.21 (m, 2H), 7.12-7.09 (m, 2H), 7.03-7.01 (m, 1H) | 520.20 | 520.18 |

TABLE 1-continued

| Compound | $^1$H NMR (CDCl$_3$, 400 MHz) | MS/FAB found | MS/FAB calc. |
|---|---|---|---|
| 7 | δ = 8.24-8.22 (m, 1H), 7.91 (t, 2H), 7.84-7.82 (m, 3H), 7.80 (d, 1H), 7.78 (d, 1H), 7.75 (d, 1H), 7.72-7.66 (m, 3H), 7.56-7.53 (m, 2H), 7.46-7.44 (dd, 1H), 7.37-7.26 (m, 7H), 7.02-6.99 (m, 1H), 0.39 (s, 9H) | 592.22 | 592.19 |
| 10 | δ = 8.21-8.19 (m, 1H), 7.99-7.92 (m, 3H), 7.85-7.82 (m, 2H), 7.81 (d, 1H), 7.79 (d, 1H), 7.77 (d, 1H), 7.72-7.69 (m, 2H), 7.58-7.51 (m, 3H), 7.46-7.44 (dd, 1H), 7.37-7.28 (m, 6H), 7.04-7.01 (m, 1H), 6.99-6.98 (dd, 1H) | 601.21 | 601.24 |
| 12 | δ = 8.08-8.04 (m, 2H), 7.95-7.90 (m, 2H), 7.84-7.81 (m, 2H), 7.80 (d, 1H), 7.77 (d, 1H), 7.76-7.74 (m, 2H), 7.73-7.69 (m, 3H), 7.55-7.52 (dd, 1H), 7.47-7.45 (dd, 1H), 7.36-7.27 (m, 6H), 7.10-7.08 (m, 1H), 7.01-6.99 (m, 1H) | 545.20 | 545.18 |
| 15 | δ = 8.34-8.33 (dd, 1H), 8.19-8.16 (m, 1H), 8.04-8.01 (m, 2H), 7.93-7.91 (d, 1H), 7.83 (d, 1H), 7.81 (d, 1H), 7.71-7.68 (m, 5H), 7.60-7.57 (m, 3H), 7.50-7.45 (m, 3H), 7.40-7.35 (m, 4H), 7.32-7.28 (m, 3H), 7.06-7.01 (m, 3H) | 596.23 | 596.21 |
| 18 | δ = 8.18-8.16 (m, 1H), 8.09-8.08 (dd, 1H), 8.03-8.01 (m, 2H), 7.94-7.92 (d, 1H), 7.84-7.79 (m, 4H), 7.72-67 (m, 3H), 7.65-7.63 (m, 1H), 7.50-7.45 (m, 2H), 7.41-7.31 (m, 7H), 7.25-7.21 (m, 2H), 7.15-7.10 (m, 2H), 7.07-7.03 (m, 2H) | 596.25 | 596.21 |
| 21 | δ = 8.41-8.39 (m, 1H), 8.30-8.28 (m, 1H), 8.15-8.14 (dd, 1H), 8.08-8.07 (dd, 1H), 7.93-7.91 (m, 1H), 7.85-7.80 (m, 5H), 7.75-7.70 (m, 2H), 7.62 (t, 1H), 7.40-7.24 (m, 10H), 7.13-7.09 (m, 3H), 7.06-7.03 (m, 1H) | 597.26 | 597.21 |
| 25 | δ = 8.21 (d, 1H), 8.10-8.08 (dd, 1H), 7.88 (d, 1H), 7.82-7.80 (m, 2H), 7.69-7.67 (dd, 1H), 7.65-7.56 (m, 4H), 7.54-7.49 (m, 2H), 7.45-7.43 (m, 1H), 7.35-7.32 (tt, 1H), 7.29-7.21 (m, 3H), 7.11-7.09 (tt, 1H), 7.06-7.01 (m, 4H), | 470.20 | 470.17 |
| 26 | δ = 8.13-8.11 (dd, 1H), 8.00-7.98 (m, 1H), 7.82-7.80 (m, 1H), 7.70-7.67 (m, 2H), 7.66-7.55 (m, 6H), 7.51-7.48 (m, 2H), 7.44-7.42 (dd, 1H), 7.33-7.21 (m, 3H), 7.12-7.10 (dd, 1H), 7.07-7.03 (m, 3H) | 538.19 | 538.15 |
| 28 | δ = 8.05-8.01 (m, 1H), 7.97-7.96 (m, 2H), 7.92-7.89 (m, 1H), 7.78-7.76 (m, 1H), 7.70 (s, 2H), 7.63-7.55 (m, 12H), 7.51-7.48 (m, 2H), 7.39-7.38 (m, 1H), 7.31-7.22 (m, 11H), 7.04-7.00 (m, 2H), 6.98-6.96 (m, 1H) | 728.23 | 728.25 |
| 31 | δ = 8.04-8.01 (m, 3H), 7.97-7.96 (m, 2H), 7.91-7.89 (m, 1H), 7.72-7.68 (m, 2H), 7.65-7.64 (m, 2H), 7.61-7.57 (m, 4H), 7.53-7.45 (m, 4H), 7.41-7.35 (m, 3H), 7.06-7.03 (m, 4H), 7.00-6.97 (m, 1H) | 546.18 | 546.20 |
| 38 | δ = 8.23-8.20 (m, 2H), 8.05-8.02 (m, 2H), 7.98-7.96 (m, 2H), 7.91-7.89 (m, 1H), 7.73-7.70 (m, 1H), 7.64-7.63 (m, 2H), 7.59-7.55 (m, 3H), 7.53-7.50 (m, 2H), 7.39 (t, 1H), 7.17-7.13 (tt, 1H), 7.06-6.99 (m, 4H) | 636.18 | 636.15 |
| 42 | δ = 8.34-8.32 (m, 1H), 8.25-8.23 (dd, 1H), 8.13-8.11 (dd, 2H), 8.09-8.08 (m, 1H), 7.94-7.91 (m, 2H), 7.85-7.83 (m, 2H), 7.71 (d, 1H), 7.57-7.53 (m, 1H), 7.47-7.40 (m, 2H), 7.38-7.32 (m, 6H), 7.25-7.23 (m, 1H), 7.16-7.10 (m, 5H), 7.03-7.01 (m, 1H) | 570.23 | 570.20 |
| 44 | δ = 8.33-8.32 (m, 1H), 8.23-8.21 (m, 1H), 8.14-8.13 (m, 2H), 8.12-8.11 (m, 1H), 8.03-8.01 (dd, 1H), 7.95-7.93 (m, 2H), 7.92-7.91 (m, 2H), 7.66-7.55 (m, 5H), 7.47-7.43 (m, 2H), 7.40-7.36 (m, 1H), 7.33-7.29 (m, 2H), 7.23-7.21 (dd, 1H), 7.16-7.09 (m, 5H) | 570.25 | 570.20 |
| 48 | δ = 8.31 (d, 1H), 8.21-8.17 (m, 1H), 7.96-7.95 (m, 2H), 7.94-7.93 (m, 2H), 7.81 (d, 1H), 7.80-7.77 (m, 3H), 7.60-7.54 (m, 7H), 7.50-7.46 (m, 3H), 7.41-7.35 (m, 4H), 7.33-7.27 (m, 5H), 7.04-7.02 (m, 1H) | 646.27 | 646.23 |
| 53 | δ = 8.41-8.39 (m, 1H), 8.26 (d, 1H), 8.13-8.11 (dd, 1H), 8.02-8.00 (dd, 2H), 7.95-7.91 (m, 3H), 7.83-7.80 (m, 3H), 7.70 (d, 1H), 7.57-7.53 (m, 1H), 7.42-7.33 (m, 10H), 7.26-7.23 (m, 2H), 7.13-7.07 (m, 3H), 7.01-6.99 (m, 1H) | 647.25 | 647.22 |
| 57 | δ = 8.11-8.09 (m, 1H), 8.03-8.01 (m, 1H), 7.97-7.96 (dd, 2H), 7.83 (d, 1H), 7.81 (d, 1H), 7.79-7.77 (m, 2H), 7.69-7.63 (m, 2H), 7.60-7.58 (m, 2H), 7.57-7.56 (m, 2H), 7.54 (d, 1H), 7.50-7.46 (m, 4H), 7.41-7.29 (m, 6H), 7.09-7.05 (m, 1H), 6.99-6.96 (m, 1H) | 596.20 | 596.21 |
| 59 | δ = 8.09-8.07 (dd, 1H), 8.06-8.04 (dd, 1H), 7.99-7.97 (m, 1H), 7.86-7.84 (m, 1H), 7.83-7.82 (dd, 1H), 7.81-7.80 (dd, 1H), 7.79-7.76 (m, 2H), 7.69-7.63 (m, 4H), 7.58-7.54 (m, 3H), 7.51-7.46 (m, 4H), 7.40-7.26 (m, 6H), 7.06-7.02 (m, 1H), 6.99-6.95 (m, 1H) | 621.19 | 621.21 |

TABLE 1-continued

| Compound | $^1$H NMR (CDCl$_3$, 400 MHz) | MS/FAB found | MS/FAB calc. |
|---|---|---|---|
| 60 | δ = 8.24-8.22 (dd, 1H), 8.05-8.02 (m, 4H), 7.93-7.90 (m, 2H), 7.83 (d, 1H), 7.81 (d, 1H), 7.79-7.76 (m, 3H), 7.71-7.68 (m, 3H), 7.64-7.60 (m, 1H), 7.48-7.45 (m, 2H), 7.41-7.28 (m, 6H), 7.23 (d, 1H), 7.04-6.96 (m, 2H) | 621.26 | 621.21 |
| 65 | δ = 8.45-8.44 (dd, 1H), 8.32-8.30 (m, 1H), 8.19 (d, 1H), 8.02-7.90 (m, 5H), 7.85-7.82 (m, 5H), 7.80-7.76 (m, 3H), 7.67-7.60 (m, 3H), 7.48-7.32 (m, 10H), 7.09-7.06 (tt, 1H), 7.01-6.99 (dd, 1H) | 673.27 | 673.24 |

Example 1

An anode was manufactured as follows: a corning 15 Ω/cm$^2$ (1200 Å) ITO glass substrate was cut to a size of 50 mm×50 mm×0.7 mm, sonicated with isopropyl alcohol and pure water each for 5 minutes, and then washed by UV irradiation for 30 minutes and ozone. The resultant glass substrate was loaded into a vacuum deposition apparatus.

2-TNATA was vacuum deposited on the substrate to form a HIL having a thickness of 600 Å. Then, 4,4'-bis[N-(1-naphthyl)-N-phenylamino]biphenyl (NPB) was vacuum deposited thereon to form a HTL having a thickness of 300 Å.

On the HTL, Compound 1 (as a blue fluorescent host) and 4,4'-bis[2-(4-(N,N-diphenylamino)phenyl)vinyl]biphenyl (DPAVBi) were co-deposited at a weight ratio of 98:2 to form an EML having a thickness of 300 Å.

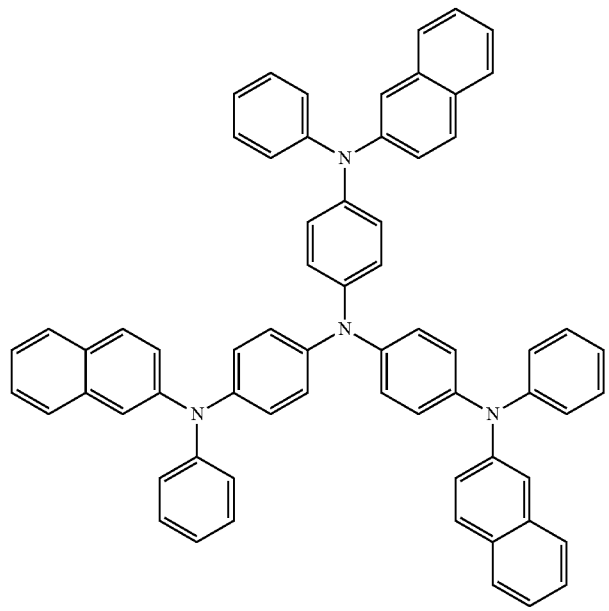

2-TNATA

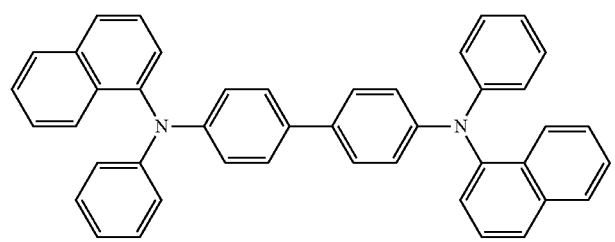

NPB

-continued

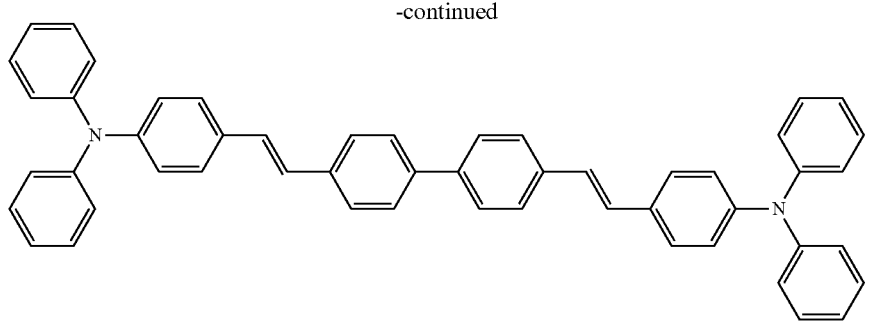

DPAVBi

Subsequently, Alq$_3$ was deposited on the EML to form an ETL having a thickness of 300 Å, and then LiF, which is a halogenated alkali metal, was deposited on the ETL to form an EIL having a thickness of 10 Å. Al was vacuum deposited to form a cathode having a thickness of 3,000 Å to form a LiF/Al electrode, thereby completing the manufacture of an organic light-emitting device.

At a current density of 10 mA/cm$^2$, the device had a driving voltage of 5.12 V, a luminescence brightness of 3,535 cd/m$^2$, a luminescence efficiency of 7.07 cd/A, and a half-lifespan (hr @100 mA/cm$^2$) of 295 hours.

Example 2

An organic light-emitting device was manufactured as in Example 1, except that Compound 7 was used instead of Compound 1 to form the EML.

At a current density of 10 mA/cm$^2$, the device had a driving voltage of 5.21 V, a luminescence brightness of 3,620 cd/m$^2$, a luminescence efficiency of 7.24 cd/A, and a half-lifespan (hr @100 mA/cm$^2$) of 308 hours.

Example 3

An organic light-emitting device was manufactured in Example 1, except that 9,10-di-naphthalene-2-yl-anthracene (DNA) was used instead of Compound 1 to form the EML, and Compound 12 was used instead of Alq$_3$ to form the ETL.

At a current density of 10 mA/cm$^2$, the device had a driving voltage of 5.37 V, a luminescence brightness of 3,725 cd/m$^2$, a luminescence efficiency of 7.45 cd/A, and a half-lifespan (hr @100 mA/cm$^2$) of 378 hours.

Example 4

An organic light-emitting device was manufactured as in Example 1, except that Compound 18 was used instead of Compound 1 to form the EML.

At a current density of 10 mA/cm$^2$, the device had a driving voltage of 5.17 V, a luminescence brightness of 3,575 cd/m$^2$, a luminescence efficiency of 7.15 cd/A, and a half-lifespan (hr @100 mA/cm$^2$) of 324 hours.

Example 5

An organic light-emitting device was manufactured as in Example 1, except that Compound 25 was used instead of Compound 1 to form the EML.

At a current density of 10 mA/cm$^2$, the device had a driving voltage of 5.26 V, a luminescence brightness of 3,380 cd/m$^2$, a luminescence efficiency of 6.76 cd/A, and a half-lifespan (hr @100 mA/cm$^2$) of 276 hours.

Example 6

An organic light-emitting device was manufactured as in Example 1, except that Compound 31 was used instead of Compound 1 to form the EML.

At a current density of 10 mA/cm$^2$, the device had a driving voltage of 5.29 V, a luminescence brightness of 3,455 cd/m$^2$, a luminescence efficiency of 6.91 cd/A, and a half-lifespan (hr @100 mA/cm$^2$) of 295 hours.

Example 7

An organic light-emitting device was manufactured as in Example 1, except that Compound 42 was used instead of Compound 1 to form the EML.

At a current density of 10 mA/cm$^2$, the device had a driving voltage of 5.33 V, a luminescence brightness of 3,665 cd/m$^2$, a luminescence efficiency of 7.33 cd/A, and a half-lifespan (hr @100 mA/cm$^2$) of 276 hours.

Example 8

An organic light-emitting device was manufactured as in Example 1, except that Compound 53 was used instead of Compound 1 to form the EML.

At a current density of 10 mA/cm$^2$, the device had a driving voltage of 5.25 V, a luminescence brightness of 3,645 cd/m$^2$, a luminescence efficiency of 7.28 cd/A, and a half-lifespan (hr @100 mA/cm$^2$) of 283 hours.

Example 9

An organic light-emitting device was manufactured as in Example 3, except that Compound 60 was used instead of Compound 12 to form the ETL.

At a current density of 10 mA/cm$^2$, the device had a driving voltage of 5.34 V, a luminescence brightness of 3,790 cd/m$^2$, a luminescence efficiency of 7.58 cd/A, and a half-lifespan (hr @100 mA/cm$^2$) of 385 hours.

Comparative Example 1

An organic light-emitting device was manufactured as in Example 1, except that DNA (depicted below) was used instead of Compound 1 as a blue fluorescent host in the EML.

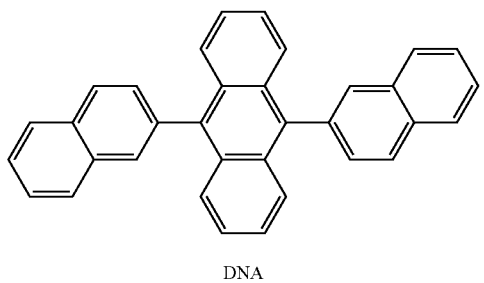 [SMILES: c1ccc2cc(-c3c4ccccc4c(-c4ccc5ccccc5c4)c4ccccc34)ccc2c1]

DNA

At a current density of 10 mA/cm², the device had a driving voltage of 7.35 V, a luminescence brightness of 2,065 cd/m², a luminescence efficiency of 4.13 cd/A, and a half-lifespan (hr @100 mA/cm²) of 145 hours.

In Examples 1 through 9, compounds represented by Formulae 1 through 3 were used as host materials for blue EMLs. Compared with DNA, the compounds represented by Formulae 1 through 3 had low driving voltages, high efficiency, and good I-V-L characteristics. In particular, OLEDs using the compounds represented by Formulae 1 through 3 exhibited significant lifespan improvement effects, thereby substantially prolonging lifespan. Representative characteristics and lifespan results were summarized and the results are shown in Table 1.

TABLE 1

|  | Emission material and Electron transport material | Driving voltage (V) | Current density (mA/cm²) | Brightness (cd/m²) | Efficiency (cd/A) | Emission color | Half lifespan (hr@100 mA/cm²) |
|---|---|---|---|---|---|---|---|
| Example 1 | Compound 1 | 5.12 | 50 | 3,535 | 7.07 | Blue | 295 hr |
| Example 2 | Compound 7 | 5.21 | 50 | 3,620 | 7.24 | Blue | 308 hr |
| Example 3 | Compound 12 | 5.37 | 50 | 3,725 | 7.45 | Blue | 378 hr |
| Example 4 | Compound 18 | 5.17 | 50 | 3,575 | 7.15 | Blue | 324 hr |
| Example 5 | Compound 25 | 5.26 | 50 | 3,380 | 6.76 | Blue | 276 hr |
| Example 6 | Compound 31 | 5.29 | 50 | 3,455 | 6.91 | Blue | 295 hr |
| Example 7 | Compound 42 | 5.33 | 50 | 3,665 | 7.33 | Blue | 276 hr |
| Example 8 | Compound 53 | 5.23 | 50 | 3,640 | 7.29 | Blue | 283 hr |
| Example 9 | Compound 60 | 5.34 | 50 | 3,790 | 7.58 | Blue | 385 hr |
| Comparative Example 1 | DNA | 7.35 | 50 | 2,065 | 4.13 | Blue | 145 hr |

As described above, according to one or more embodiments of the present invention, compounds represented by Formulae 1 through 3 are suitable for use in a full color device, such as red, green, blue, or white fluorescent or phosphorescent devices. Due to the inclusion of the compound of one of Formulae 1 through 3, the organic light-emitting device has high efficiency, low voltage, high brightness, and a long lifespan.

It should be understood that the exemplary embodiments described herein are presented for descriptive purposes only, and not for purposes of limitation. Accordingly, descriptions of features or aspects within each embodiment should typically be considered as available for other similar features or aspects in other embodiments.

While one or more embodiments of the present invention have been described, it will be understood by those of ordinary skill in the art that various changes may be made to the described embodiments without departing from the spirit and scope of the present invention as defined by the following claims.

What is claimed is:

1. A compound represented by Formula 1, Formula 2, or Formula 3:

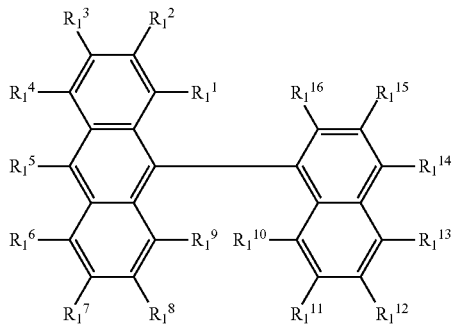

Formula 1

-continued

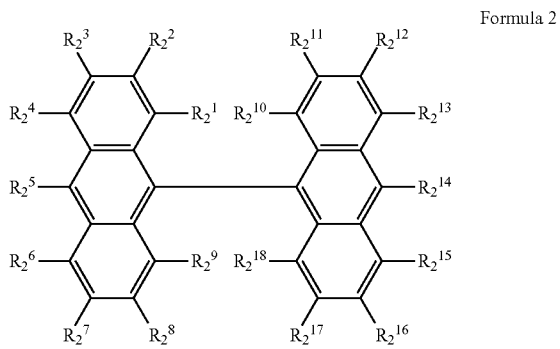

Formula 2

-continued

Formula 3
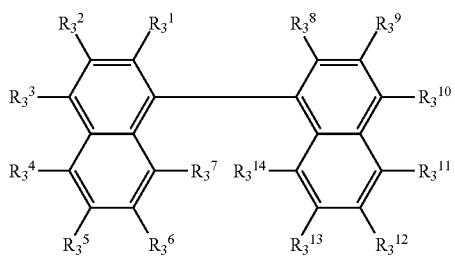

wherein, in Formulae 1, 2, and 3, $R_1^1$ to $R_1^{16}$, $R_2^1$ to $R_2^{18}$, and $R_3^1$ to $R_3^{14}$ are each independently a hydrogen atom, a deuterium atom, a halogen atom, a nitro group, a cyano group, a substituted or unsubstituted $C_1$ to $C_{60}$ alkyl group, a substituted or unsubstituted $C_2$ to $C_{60}$ alkenyl group, a substituted or unsubstituted $C_3$ to $C_{60}$ cycloalkyl group, a substituted or unsubstituted $C_6$ to $C_{60}$ aryl group, a substituted or unsubstituted $C_1$ to $C_{60}$ hetero aryl group, a substituted or unsubstituted $C_6$ to $C_{60}$ condensed polycyclic group, or L, provided that at least one of $R_1^1$ to $R_1^{16}$, at least one of $R_2^1$ to $R_2^{18}$, and at least one of $R_3^1$ to $R_3^{14}$ is L, wherein:

L is,

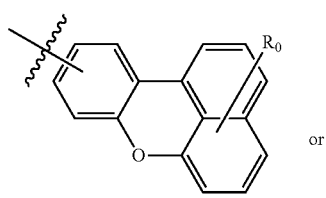

or

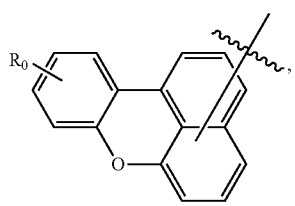

and $R_0$ is a hydrogen atom, a deuterium atom, a halogen atom, a nitro group, a cyano group, a substituted or unsubstituted $C_1$ to $C_{60}$ alkyl group, a substituted or unsubstituted $C_2$ to $C_{60}$ alkenyl group, a substituted or unsubstituted $C_3$ to $C_{60}$ cycloalkyl group, a substituted or unsubstituted $C_6$ to $C_{60}$ aryl group, a substituted or unsubstituted $C_1$ to $C_{60}$ hetero aryl group, or a substituted or unsubstituted $C_6$ to $C_{60}$ condensed polycyclic group.

2. The compound of claim 1, wherein the compound represented by Formula 1 is represented by one of Formulae 4 through 7:

Formula 4
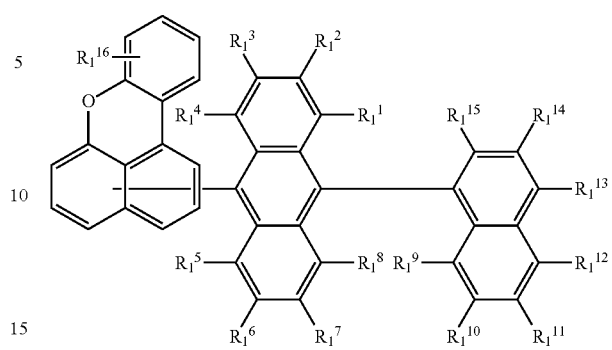

Formula 5
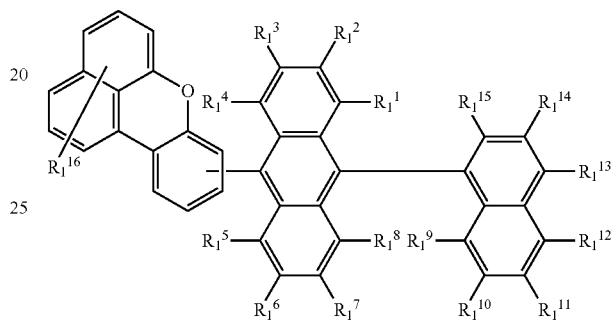

Formula 6
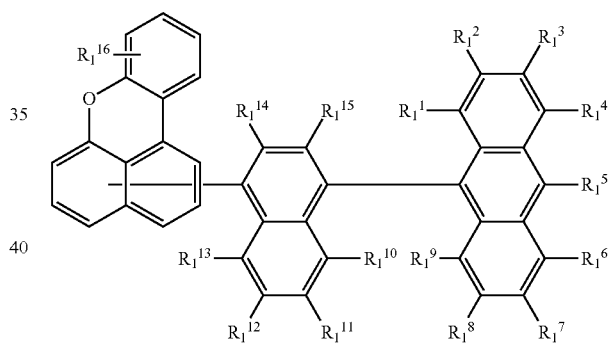

Formula 7
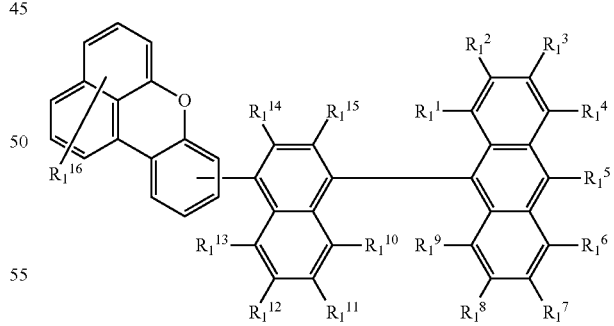

wherein in Formulae 4 to 7, $R_1^1$ to $R_1^{16}$ are each independently a hydrogen atom, a deuterium atom, a halogen atom, a nitro group, a cyano group, a substituted or unsubstituted $C_1$ to $C_{60}$ alkyl group, a substituted or unsubstituted $C_2$ to $C_{60}$ alkenyl group, a substituted or unsubstituted $C_3$ to $C_{60}$ cycloalkyl group, a substituted or unsubstituted $C_6$ to $C_{60}$ aryl group, a substituted or unsubstituted $C_1$ to $C_{60}$ hetero aryl group, or a substituted or unsubstituted $C_6$ to $C_{60}$ condensed polycyclic group.

3. The compound of claim 1, wherein the compound represented by Formula 2 is represented by Formula 8 or 9:

Formula 8

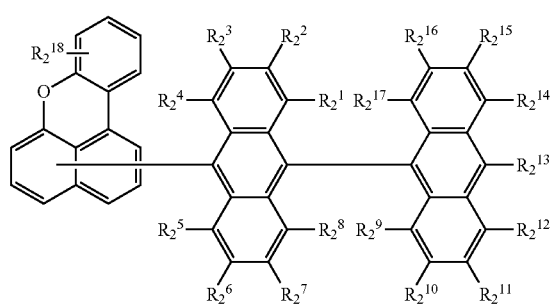

Formula 9

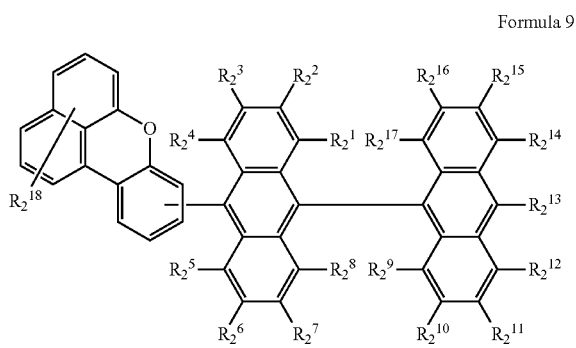

wherein, in Formulae 8 and 9, $R_2^1$ to $R_2^{18}$ are each independently a hydrogen atom, a deuterium atom, a halogen atom, a nitro group, a cyano group, a substituted or unsubstituted $C_1$ to $C_{60}$ alkyl group, a substituted or unsubstituted $C_2$ to $C_{60}$ alkenyl group, a substituted or unsubstituted $C_3$ to $C_{60}$ cycloalkyl group, a substituted or unsubstituted $C_6$ to $C_{60}$ aryl group, a substituted or unsubstituted $C_1$ to $C_{50}$ hetero aryl group, or a substituted or unsubstituted $C_6$ to $C_{60}$ condensed polycyclic group.

4. The compound of claim 1, wherein the compound represented by Formula 3 is represented by Formula 10 or 11:

Formula 10

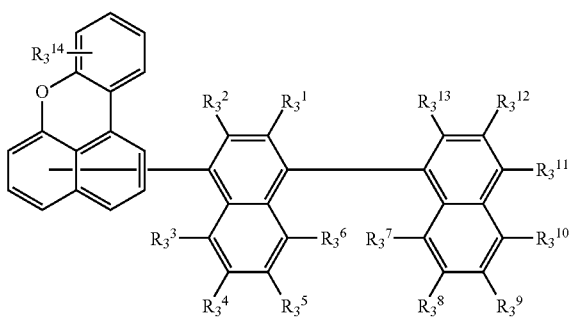

Formula 11

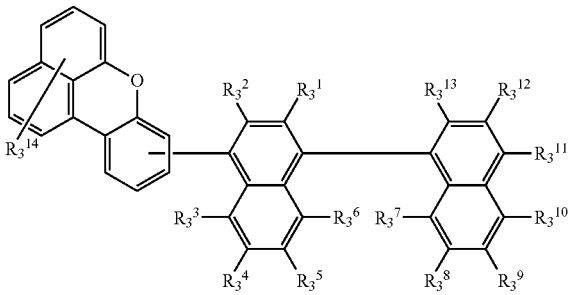

Wherein, in Formulae 10 and 11, $R_3^1$ to $R_3^{14}$ are each independently a hydrogen atom, a deuterium atom, a halogen atom, a nitro group, a cyano group, a substituted or unsubstituted $C_1$ to $C_{60}$ alkyl group, a substituted or unsubstituted $C_2$ to $C_{60}$ alkenyl group, a substituted or unsubstituted $C_3$ to $C_{60}$ cycloalkyl group, a substituted or unsubstituted $C_6$ to $C_{60}$ aryl group, a substituted or unsubstituted $C_1$ to $C_{60}$ hetero aryl group, or a substituted or unsubstituted $C_6$ to $C_{60}$ condensed polycyclic group.

5. The compound of claim 1, wherein $R_1^1$, $R_1^2$, $R_1^8$, $R_1^9$, $R_1^{10}$, $R_1^{11}$, and $R_1^{16}$ of Formula 1, $R_2^1$, $R_2^2$, $R_2^8$, $R_2^9$, $R_2^{10}$, $R_2^{11}$, $R_2^{17}$, and $R_2^{18}$ of Formula 2, and $R_3^1$, $R_3^6$, $R_3^7$, $R_3^6$, $R_3^{13}$, and $R_3^{14}$ of Formula 3 are each independently a hydrogen atom or a deuterium atom.

6. The compound of claim 2, wherein $R_1^1$ to $R_1^{10}$, and $R_1^{15}$ of Formulae 4 and 5, and $R_1^1$ to $R_1^4$, $R_1^6$ to $R_1^{11}$, and $R_1^{15}$ of Formulae 6 and 7 are each independently a hydrogen atom or a deuterium atom.

7. The compound of claim 3, wherein $R_2^1$ to $R_2^{10}$, $R_2^{16}$, and $R_2^{17}$ of Formulae 8 and 9 are each independently a hydrogen atom or a deuterium atom.

8. The compound of claim 4, wherein $R_3^1$ to $R_3^8$, and $R_3^{13}$ of Formulae 10 and 11 are each independently a hydrogen atom or a deuterium atom.

9. The compound of claim 1, wherein at least one of $R_1^1$-$R_1^{16}$, at least one of $R_2^1$-$R_2^{18}$, and at least one of $R_3^1$-$R_3^{14}$, in Formulae 1, 2 and 3 is L, and $R_0$ and remaining ones of $R_1^1$-$R_1^{16}$, $R_2^1$-$R_2^{18}$, $R_3^1$-$R_3^{14}$ of Formulae 1, 2, and 3 are each independently a hydrogen atom, a deuterium atom, a cyano group, a trihalomethyl group, or any one of Formulae 2a through 2c:

2a

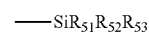

2b

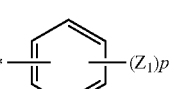

2c

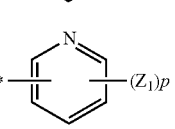

wherein, in Formulae 2a through 2c:

$R_{51}$, $R_{52}$, $R_{53}$, and $Z_1$ are each independently a hydrogen atom, a deuterium atom, a substituted or unsubstituted $C_1$ to $C_{20}$ alkyl group, a substituted or unsubstituted $C_6$ to $C_{20}$ aryl group, a substituted or unsubstituted $C_1$ to $C_{20}$ heteroaryl group, a substituted or unsubstituted $C_6$ to $C_{20}$ condensed polycyclic group, an amino group substituted with a $C_6$ to $C_{20}$ aryl group or a $C_2$ to $C_{20}$ heteroaryl group, a halogen atom, a cyano group, a nitro group, a hydroxyl group, or a carboxyl group;

p in Formula 2b is an integer of 1 to 5, and p in Formula 2c is an integer of 1 to 4; and \* indicates a binding site to Formula 1, 2 or 3.

10. The compound of claim 2, wherein $R_1^{13}$ and $R_1^{16}$ of Formulae 4 and 5 are each independently a hydrogen atom, a deuterium atom, a cyano group, a trihalomethyl group, or any one of Formulae 2a to 2c:

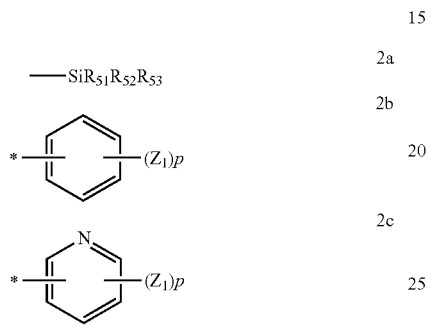

wherein, in Formulae 2a through 2c:

$R_{51}$, $R_{52}$, $R_{53}$, and $Z_1$ are each independently a hydrogen atom, a deuterium atom, a substituted or unsubstituted $C_1$ to $C_{20}$ alkyl group, a substituted or unsubstituted $C_6$ to $C_{20}$ aryl group, a substituted or unsubstituted $C_1$ to $C_{20}$ heteroaryl group, a substituted or unsubstituted $C_6$ to $C_{20}$ condensed polycyclic group, an amino group substituted with a $C_6$ to $C_{20}$ aryl group or a $C_2$ to $C_{20}$ heteroaryl group, a halogen atom, a cyano group, a nitro group, a hydroxyl group, or a carboxyl group;

p in Formula 2b is an integer of 1 to 5, and p in Formula 2c is an integer of 1 to 4; and \* indicates a binding.

11. The compound of claim 3, wherein $R_1^5$ and $R_1^{16}$ of Formulae 6 and 7 are each independently a hydrogen atom, a deuterium atom, a cyano group, a trihalomethyl group, or any one of Formulae 2a through 2c:

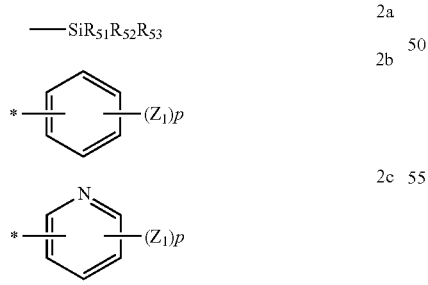

wherein, in Formulae 2a through 2c:

$R_{51}$, $R_{52}$, $R_{53}$, and $Z_1$ are each independently a hydrogen atom, a deuterium atom, a substituted or unsubstituted $C_1$ to $C_{20}$ alkyl group, a substituted or unsubstituted $C_6$ to $C_{20}$ aryl group, a substituted or unsubstituted $C_2$ to $C_{20}$ heteroaryl group, a substituted or unsubstituted $C_6$ to $C_{20}$ condensed polycyclic group, an amino group substituted with a $C_6$ to $C_{20}$ aryl group or a $C_1$ to $C_{20}$ heteroaryl group, a halogen atom, a cyano group, a nitro group, a hydroxyl group, or a carboxyl group;

p in Formula 2b is an integer of 1 to 5, and p in Formula 2c is an integer of 1 to 4; and \* indicates a binding.

12. The compound of claim 4, wherein $R_3^{11}$ and $R_3^{14}$ of Formulae 10 and 11 are each independently a hydrogen atom, a deuterium atom, a cyano group, a trihalomethyl group, or any one of Formulae 2a through 2c:

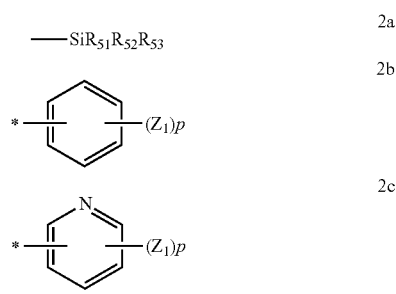

wherein, in Formulae 2a through 2c:

$R_{51}$, $R_{52}$, $R_{53}$, and $Z_1$ are each independently a hydrogen atom, a deuterium atom, a substituted or unsubstituted $C_1$ to $C_{20}$ alkyl group, a substituted or unsubstituted $C_6$ to $C_{20}$ aryl group, a substituted or unsubstituted $C_2$ to $C_{20}$ heteroaryl group, a substituted or unsubstituted $C_6$ to $C_{20}$ condensed polycyclic group, an amino group substituted with a $C_6$ to $C_{20}$ aryl group or a $C_1$ to $C_{20}$ heteroaryl group, a halogen atom, a cyano group, a nitro group, a hydroxyl group, or a carboxyl group;

p in Formula 2b is an integer of 1 to 5, and p in Formula 2c is an integer of 1 to 4; and \* indicates a binding.

13. The compound of claim 1, wherein the compound represented by Formula 1 is one of Compounds 1, 7, 12, 18, 25, 31, 42, 53 and 60:

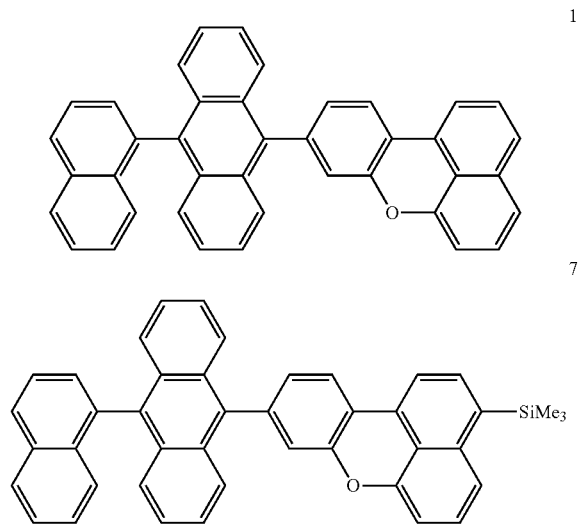

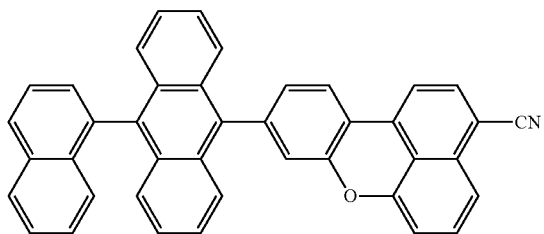
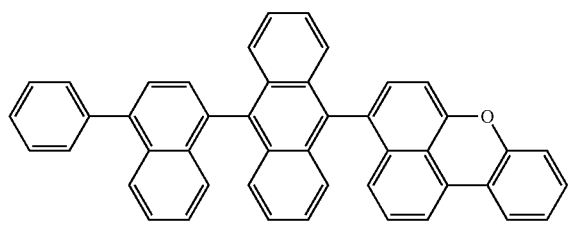
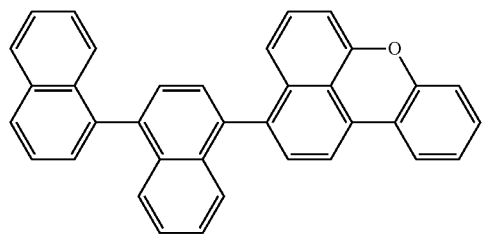
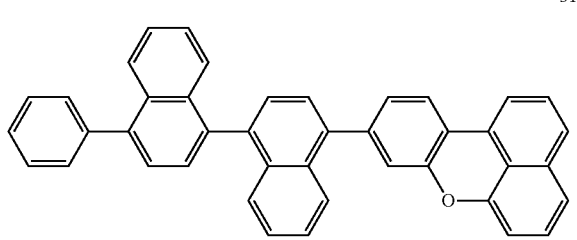
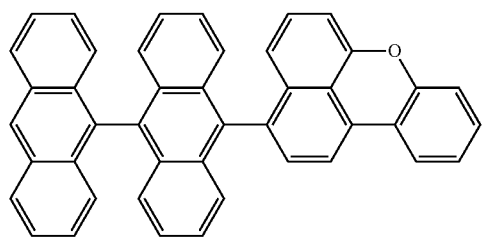
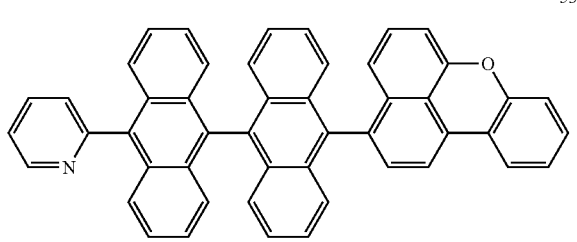
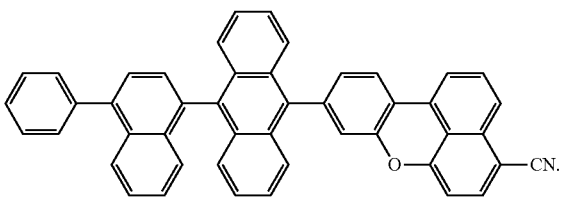

14. An organic light-emitting device comprising:
a first electrode;
a second electrode; and
an organic layer between the first electrode and the second electrode, and comprising the compound of claim 1.

15. The organic light-emitting device of claim 14, wherein the organic layer is an emission layer, an electron injection layer, an electron transport layer, or a functional layer having electron injection capability and electron transportation capability.

16. The organic light-emitting device of claim 14, wherein the organic layer comprises:
an emission layer comprising an anthracene-based compound, an arylamine-based compound; or a styryl-based compound, and
an electron injection layer, an electron transport layer, a functional layer having electron injection capability and electron transportation capability, a hole injection layer, a hole transport layer, or a functional layer having hole injection capability and hole transportation capability.

17. The organic light-emitting device of claim 14, wherein the organic layer comprises:
an emission layer comprising a red layer, a green layer, a blue layer, and a white layer, and one of the red layer, the green layer, the blue layer or the white layer comprises a phosphorescent compound, and
an electron injection layer, an electron transport layer, a functional layer having electron injection capability and electron transportation capability, a hole injection layer, a hole transport layer, or a functional layer having hole injection capability and hole transportation capability.

18. The organic light-emitting device of claim 17, wherein the hole injection layer, the hole transport layer, or the functional layer having hole injection capability and hole transport capability comprises a charge-generation material.

19. The organic light-emitting device of claim 14, wherein the organic layer is formed by a wet process using the compound of claim 1.

20. A flat display apparatus comprising the organic light-emitting device of claim 14, wherein the first electrode of the organic light-emitting device is electrically connected to a source electrode or a drain electrode of a thin film transistor.

* * * * *